US012753208B2

(12) United States Patent
Bernal et al.

(10) Patent No.: US 12,753,208 B2
(45) Date of Patent: Oct. 6, 2026

(54) ANTIVIRAL STRUCTURALLY-STABILIZED EBOLAVIRUS PEPTIDES AND USES THEREOF

(71) Applicants: Dana-Farber Cancer Institute, Inc., Boston, MA (US); The United States of America, as represented by The Secretary, Department of Health and Human Services, Bethesda, MD (US)

(72) Inventors: Federico Bernal, Gaithersburg, MD (US); Amanda L. Whiting, Dallas, TX (US); Loren D. Walensky, Newton, MA (US); Gregory H. Bird, Pelham, NH (US)

(73) Assignees: Dana-Farber Cancer Institute, Inc., Boston, MA (US); The United States of America, as represented by the Secretary, Department of Health and Human Services, Bethesda, MD (US)

(*) Notice: Subject to any disclaimer, the term of this patent is extended or adjusted under 35 U.S.C. 154(b) by 763 days.

(21) Appl. No.: 18/035,427

(22) PCT Filed: Nov. 4, 2021

(86) PCT No.: PCT/US2021/058023
§ 371 (c)(1),
(2) Date: May 4, 2023

(87) PCT Pub. No.: WO2022/098848
PCT Pub. Date: May 12, 2022

(65) Prior Publication Data

US 2024/0002450 A1 Jan. 4, 2024

Related U.S. Application Data

(60) Provisional application No. 63/110,169, filed on Nov. 5, 2020.

(51) Int. Cl.

| | |
|---|---|
| ***A61K 38/16*** | (2006.01) |
| ***A61P 31/14*** | (2006.01) |
| ***C07K 14/08*** | (2006.01) |
| ***C12N 7/00*** | (2006.01) |
| *A61K 38/00* | (2006.01) |

(52) U.S. Cl.
CPC .............. *C07K 14/08* (2013.01); *A61P 31/14* (2018.01); *C12N 7/00* (2013.01); *A61K 38/00* (2013.01); *C12N 2760/14122* (2013.01); *C12N 2760/14133* (2013.01)

(58) Field of Classification Search
None
See application file for complete search history.

(56) References Cited

U.S. PATENT DOCUMENTS

| | | | |
|---|---|---|---|
| 5,446,090 | A | 8/1995 | Harris |
| 6,348,558 | B1 | 2/2002 | Harris et al. |
| 7,723,468 | B2 | 5/2010 | Daffre et al. |
| 8,889,632 | B2 | 11/2014 | Bernal et al. |
| 2005/0250680 | A1 | 11/2005 | Walensky et al. |
| 2010/0286057 | A1 | 11/2010 | Walensky et al. |
| 2012/0172285 | A1 | 7/2012 | Walensky et al. |
| 2017/0247418 | A1 | 8/2017 | Clinton et al. |
| 2025/0288658 | A1 | 9/2025 | Bird et al. |

FOREIGN PATENT DOCUMENTS

| | | |
|---|---|---|
| CN | 105362278 | 3/2016 |
| WO | WO 1999/014259 | 3/1999 |
| WO | WO 1999/034833 | 7/1999 |
| WO | WO 2008/121767 | 10/2008 |
| WO | WO 2009/108261 | 9/2009 |
| WO | WO 2010/060112 | 5/2010 |
| WO | WO 2010/068684 | 6/2010 |
| WO | WO 2010/148335 | 12/2010 |
| WO | WO 2013/102211 | 7/2013 |
| WO | WO 2016/049380 | 3/2016 |
| WO | WO 2016/134146 | 8/2016 |
| WO | WO 2017/015457 | 1/2017 |
| WO | WO 2017/147283 | 8/2017 |
| WO | WO 2023/215784 | 11/2023 |

OTHER PUBLICATIONS

International Preliminary Report on Patentability in International Appln. No. PCT/US2021/058023, mailed on May 19, 2023, 11 pages.
International Preliminary Report on Patentability in International Appln. No. PCT/US2023/066545, mailed on Nov. 14, 2024, 7 pages.
Jamieson, "Emerging peptide science in the United Kingdom," Peptide Science, Jan. 2021, 113(1):e24216, 4 pages.
U.S. Appl. No. 18/862,216, 2025/0288658, filed Nov. 1, 2024, Bird.
Agnandji et al., "Phase 1 Trials of rVSV Ebola Vaccine in Africa and Europe," New England Journal of Medicine, Apr. 28, 2016, 374(17):1647-1660.
Aguilar-Alonso et al., "Biophysical and biological evaluation of optimized stapled peptide inhibitors of the linear ubiquitin chain assembly complex (LUBAC)," Bioorganic & Medicinal Chemistry, Mar. 15, 2018, 26:1179-1188.
Altschul et al., "Gapped BLAST and PSI-BLAST: a new generation of protein database search programs," Nucleic Acids Res., 1997, 25:3389-3402.
Balaram, "Non-standard amino acids in peptide design and protein engineering," Cur. Opin. Struct. Biol., Jan. 1992, 2(6):845-851.
Berge et al., "Pharmaceutical salts," J. Pharm. Sci., Jan. 1977, 66(1):1-9.

(Continued)

*Primary Examiner* — Fred H Reynolds
(74) *Attorney, Agent, or Firm* — Fish & Richardson P.C.

(57) ABSTRACT

This disclosure features structurally-stabilized Ebola virus antiviral peptides. Also disclosed are methods of using such structurally-stabilized peptides in the treatment or prevention of an Ebola virus infection or Ebola virus disease.

20 Claims, 18 Drawing Sheets

Specification includes a Sequence Listing.

(56) References Cited

OTHER PUBLICATIONS

Bernal et al., "A Stapled p53 Helix Overcomes HDMX-Mediated Suppression of p53," Cancer Cell, Nov. 16, 2018, 18(5):411-422.
Bernal et al., "Reactivation of the p53 Tumor Suppressor Pathway by a Stapled p53 Peptide," Journal of the American Chemical Society, Mar. 7, 2007, 129(9):2456-2457.
Bird et al., "Biophysical determinants for cellular uptake of hydrocarbon-stapled peptide helices," Nat. Chem. Biol., Oct. 2016, 12(10):845-852.
Bird et al., "Chemical synthesis of hydrocarbon-stapled peptides for protein interaction research and therapeutic targeting," Current Protocols in Chemical Biology, Sep. 2011, 3(3):99-117.
Bird et al., "Hydrocarbon double-stapling remedies the proteolytic instability of a lengthy peptide therapeutic," Proceedings of the National Academy of Sciences, Aug. 10, 2010, 107(32):14093-14098.
Bird et al., "Hydrocarbon-stitched peptide agonists of glucagon-like peptide-1 receptor," ACS Chem Biol., Apr. 29, 2020, 15(6):1340-1348.
Bird et al., "Mucosal delivery of a double-stapled RSV peptide prevents nasopulmonary infection," The Journal of Clinical Investigation, Apr. 17, 2014, 124(5):2113-2124.
Bird et al., "Stapled HIV-1 peptides recapitulate antigenic structures and engage broadly neutralizing antibodies," Nature Structure & Molecular Biology, Dec. 2014, 21(12):1058-1067.
Bird et al., "Synthesis and Biophysical Characterization of Stabilized α-Helices of BCL-2 Domains," Methods Enzymol., Jan. 2008, 446:369-386.
Blackwell et al., "Highly Efficient Synthesis of Covalently Cross-Linked Peptide Helices by Ring-Closing Metathesis," Chem. Int. Ed., 1994, 37(23):3281-3284.
Blackwell et al., "Ring-Closing Metathesis of Olefinic Peptides: Design, Synthesis, and Structural Characterization of Macrocyclic Helical Peptides," J. Org. Chem., Aug. 10, 2001, 66(16):5291-5302.
Brunel et al., "Synthesis of constrained helical peptides by thioether ligation: application to analogs of gp41," Chemical Communications, 2005, 20:2552-2554.
CDC.gov [online], "Years of Ebola Virus Disease Outbreaks," 2019, via Internet Archive: Wayback Machine URL: <https://web.archive.org/web/20191030185333/https://www.cdc.gov/vhf/ebola/history/chronology.html>, retrieved on May 22, 2024, retrieved from URL: <https://www.cdc.gov/ebola/outbreaks/?CDC_AAref_Val=https://www.cdc.gov/vhf/ebola/history/chronology.html>, 15 pages.
Chapman et al., "A highly stable short α-helix constrained by a main-chain hydrogen-bond surrogate," J. Am. Chem. Soc., Oct. 6, 2004, 126(39):12252-12253.
Chin et al., "Design and Evolution of a Miniature Bcl-2 Binding Protein," Angew. Chem. Int. Ed., 2001, 40(20):3806-3809.
ClinicalTrials.gov [online], "ALRN-6924 In Patients With Advanced Solid Tumors or Lymphomas," NCT02264613, Jul. 14, 2020, retrieved on May 22, 2024, retrieved from URL: <https://clinicaltrials.gov/ct2/show/NCT02264613?term=NCT02264613>, 27 pages.
ClinicalTrials.gov [online], "Investigational Therapeutics for the Treatment of People With Ebola Virus Disease," NCT03719586, Sep. 8, 2021, retrieved on May 22, 2024, retrieved from URL: <https://clinicaltrials.gov/ct2/show/NCT03719586?term=Zmapp&cond-Ebola+Virus+Disease&cntry=CD&rank=1>, 51 pages.
ClinicalTrials.gov [online], "Safety Study of ALRN-6924 in Patients with Acute Myeloid Leukemia or Advanced Myelodysplastic Syndrome," NCT02909972, Nov. 11, 2019, retrieved on May 22, 2024, retrieved from URL: <https://clinicaltrials.gov/ct2/show/NCT02909972?term=ALRN-6924>, 25 pages.
Clinton et al., "Design and characterization of ebolavirus GP prehairpin intermediate mimics as drug targets," Protein Science, Apr. 2015, 24(4):446-463.
Cui et al., "Stapled peptide-based membrane fusion inhibitors of hepatitis C virus," Bioorganic & Medicinal Chemistry, Jun. 15, 2013, 21(12):3547-3554.
Devi et al., "Antibodies to poly [(2-->8)-α-*N*-acetylneuraminic acid] and poly [(2-->9)-α-*N*-acetylneuraminic acid] are elicited by immunization of mice with *Escherichia coli* K92 conjugates: potential vaccines for groups B and C meningococci and *E. coli* K1," Proceedings of the National Academy of Sciences, Aug. 15, 1991, 88(16):7175-7179.
Eichler et al., "Application of pseudotyped virus particles to monitor Ebola virus and SARS-CoV-2 viral entry in human cell lines," STAR Protocols, Dec. 17, 2021, 2(4):100818, 14 pages.
Fattom et al., "Serum Antibody Response in Adult Volunteers Elicited by Injection of *Streptococcus pneumoniae* Type 12F Polysaccharide Alone or Conjugated to Diphtheria Toxoid," Infect. Immun., Jul. 1990, 58(7):2309-2312.
Fields et al., "Synthetic Peptides: A User's Guide," ed. Grant, W. H. Freeman & Co., New York, N.Y., 1992, Chapter 3, 188 pages.
Gaillard et al., "A Short Double-Stapled Peptide Inhibits Respiratory Syncytial Virus Entry and Spreading," Antimicrobial Agents and Chemotherapy, Apr. 2017, 61(4):1-19.
GenBank Accession No. KX000398, "Zaire ebolavirus isolate Ebola virus/*H.sapiens*-tc/GIN/2014/Makona-C05, partial genome," Apr. 6, 2016, 9 pages.
Gregory et al., "Structure and function of the complete internal fusion loop from Ebolavirus glycoprotein 2," Proceedings of the National Academy of Sciences, Jul. 5, 2011, 108(27):11211-11216.
Gunnoo et al., "Bioconjugation—using selective chemistry to enhance the properties of proteins and peptides as therapeutics and carriers," Org. Biomol. Chem., 2016, 14(34):8002-8013.
Haney et al., "Promoting peptide α-helix formation with dynamic covalent oxime side-chain cross-links," Chem. Commun., 2011, 47(39):10915-10917.
Harrison et al., "Designed protein mimics of the Ebola virus glycoprotein GP2 α-helical bundle: Stability and pH effects," Protein Sci., Sep. 2011, 20(9):1587-1596.
Harrison et al., "Role of Electrostatic Repulsion in Controlling pH-Dependent Conformational Changes of Viral Fusion Proteins," Structure, Jul. 22, 2013, 21(7):1085-1096.
Higgins et al., "C-peptide inhibitors of Ebola virus glycoprotein-mediated cell entry: effects of conjugation to cholesterol and side chain-side chain crosslinking," Bioorg Med Chem Lett., Oct. 2013, 23(19):5356-5360.
Hilinski et al., "Stitched α-Helical Peptides via Bis Ring-Closing Metathesis," J Am Chem Soc., Sep. 3, 2014, 136(35):12314-22.
Horne et al., "Sequence-Based Design of α/ß-Peptide Foldamers that Mimic BH3 Domains," Chem., Int. Ed., 2008, 47(15):2853-2856.
International Search Report and Written Opinion in in International Application No. PCT/US2021/058023, mailed on Apr. 25, 2022, 21 pages.
International Search Report and Written Opinion in International Application No. PCT/US2023/066545, mailed on Sep. 4, 2023, 15 pages.
Invitation to Pay Additional Fees and, Where Applicable, Protest Fee in International Application No. PCT/US2021/058023, mailed on Mar. 2, 2022, 16 pages.
Jackson et al., "General Approach to the Synthesis of Short α-Helical Peptides," Am. Chem. Soc., Nov. 1991, 113(24):9391-9392.
Kaletsky et al., "Proteolysis of the Ebola Virus Glycoproteins Enhances Virus Binding and Infectivity," Journal of Virology, Dec. 15, 2007, 81(24):13378-13384.
Katen et al., "Repurposing staples for viruses: applying peptide design to RSV prophylaxis," The Journal of Clinical Investigation, May 2014, 124(5):1889-1891.
Kawamoto et al., "Design of Triazole-Stapled BCL9 α-Helical Peptides to Target the β-Catenin/B-Cell CLL/lymphoma 9 (BCL9) Protein-Protein Interaction," Journal of Medicinal Chemistry, Feb. 2012, 55(3):1137-1146.
Kemp et al., "The Structure and Energetics of Helix Formation by Short Templated Peptides in Aqueous Solution. 2. Characterization of the Helical Structure of Ac-$Hel_1$-$Ala_6$-OH.," Journal of the American Chemical Society, May 8, 1996, 118(18):4240-4248.
Kennedy et al., "Phase 2 Placebo-Controlled Trial of Two Vaccines to Prevent Ebola in Liberia," New England Journal of Medicine, Oct. 12, 2017, 377(15):1438-1447.

(56) References Cited

OTHER PUBLICATIONS

Kim et al., "Introduction of All-Hydrocarbon *i, i*+ 3 Staples into α-Helices via Ring-Closing Olefin Metathesis," Organic Letters, Jul. 2, 2010, 12(13):3046-3049.
Kumita et al., "Photo-control of helix content in a short peptide," Proceedings of the National Academy of Sciences, Apr. 11, 2000, 97(8):3803-3808.
Lau et al., "Functionalised staple linkages for modulating the cellular activity of stapled peptides," Chem. Sci., 2014, 5:1804-1809.
Lau et al., "Peptide stapling techniques based on different macrocyclisation chemistries," Chem. Soc. Rev., 2015, 44:91-102.
Lee et al., "*Ebolavirus* glycoprotein structure and mechanism of entry," Future Virology, Nov. 2009, 4(6):621-635.
Lee et al., "Structure of the Ebola Virus Envelope Protein MPER/TM Domain and its Interaction with the Fusion Loop Explains their Fusion Activity," 402-Pos—Board B167, Biophysical Journal, Feb. 12, 2017, 112(3):78a.
Lee et al., "Structure of the Ebola virus glycoprotein bound to an antibody from a human survivor," Nature, Jul. 10, 2008, 454(7201):177-182.
Li et al., "Current status on the development of pseudoviruses for enveloped viruses," Reviews in Medical Virology, Jan. 2018, 28(1):e1963, 10 pages.
Madden et al., "Facile synthesis of stapled, structurally reinforced peptide helices *via* a photoinduced intramolecular 1,3-dipolar cycloaddition reaction," Chem Communications, Oct. 7, 2009, 37:5588-5590.
Madden et al., "Synthesis of cell-permeable stapled peptide dual inhibitors of the p53-Mdm2/Mdmx interactions via photoinduced cycloaddition," Bioorg. Med. Chem. Lett., Mar. 2011, 21(5):1472-1475.
Malashkevich et al., "Core structure of the envelope glycoprotein GP2 from Ebola virus at 1.9-Å resolution," Proceedings of the National Academy of Sciences, Mar. 1999, 96(6):2662-2667.
Miller et al., "Inhibition of Ebola Virus Entry by a C-peptide Targeted to Endosomes," Journal of Biological Chemistry, May 6, 2011, 286(18):15854-15861.
Netter et al., "Heptad Repeat 2-Based Peptides Inhibit Avian Sarcoma and Leukosis Virus Subgroup A Infection and Identify a Fusion Intermediate," Journal of Virology, Dec. 2004, 78(24):13430-13439.
Nyakatura et al., "Chemical and Structural Aspects of Ebola Virus Entry Inhibitors," Infectious Disease, Jan. 9, 2015, 1(1):42-52.
Orner et al., "Toward Proteomimetics: Terphenyl Derivatives as Structural and Functional Mimics of Extended Regions of α-Helix," J. Am. Chem. Soc., Jun. 6, 2001, 123(22):5382-5383.
Payne et al., "Inhibition of Bacterial Gene Transcription with an RpoN-Based Stapled Peptide," Cell Chemical Biology, Sep. 20, 2018, 25(9):1059-1066.
Pessi et al., "Cholestero-conjugated stapled peptides inhibit Ebola and Marburg viruses in vitro and in vivo," Antiviral Research, Nov. 2019, 171:104592.
Phelan et al., "A General Method for Constraining Short Peptides to an α-Helical Conformation," J. Am. Chem. Soc., Jan. 22, 1997, 119(3):455-460.
RCSB.org [online], "1EBO—Crystal Structure of the Ebola Virus Membrane—Fusion Subunit, GP2, From the Envelope Glycoprotein Ectodomain," Nov. 3, 1998, retrieved on May 22, 2024, retrieved from URL: <https://www.rcsb.org/structure/1EBO>, 4 pages.
RCSB.org [online], "2EBO—Core Structure of GP2 From Ebola Virus," Dec. 24, 1998, retrieved on May 22, 2024, retrieved from URL: <https://www.rcsb.org/structure/2EBO>, 4 pages.
Regules et al., "A Recombinant Vesicular Stomatitis Virus Ebola Vaccine," New England Journal of Medicine, Jan. 26, 2017, 376(4):330-341.
Remington's Pharmaceutical Sciences, 17th Ed., Mack Publishing Company, Easton, PA, 1985, p. 1418.
Rewar et al., "Transmission of Ebola Virus Disease: An Overview," Annals of Global Health, Nov. 2014, 80(6):444-451.
Rijal et al., "Therapeutic Monoclonal Antibodies for Ebola Virus Infection Derived from Vaccinated Humans," Cell Reports, Apr. 2, 2019, 27(1):172-186.
Rognan, "Rational design of protein-protein interaction inhibitors," MedChemComm., Sep. 2014, 6(1):51-60.
Sakagami et al., "Importance of Net Hydrophobicity in the Cellular Uptake of All-Hydrocarbon Stapled Peptides," Molecular Pharmaceutics, Feb. 8, 2018, 15(3):1332-1340.
Schafmeister et al., "An all-hydrocarbon cross-linking system for enhancing the helicity and metabolic stability of peptides.," J. Am Chem. Soc., Jun. 21, 2000, 122(24):5891-5892.
Schneider-Futschik et al., "Contemporary Anti-Ebola Drug Discovery Approaches and Platforms," ACS Infectious Diseases, Dec. 5, 2018, 5(1):35-48.
Shepherd et al., "Single Turn Peptide Alpha Helices with Exceptional Stability in Water," J. Am. Chem. Soc., Mar. 9, 2005, 127(9):2974-2983.
Shim et al., "A New *i, i*+ 3 Peptide Stapling System for α-Helix Stabilization," Chemical Biology & Drug Design, Dec. 2013, 82(6):635-642.
Spokoyny et al., "A Perfluoroaryl-Cysteine $S_NAr$ Chemistry Approach to Unprotected Peptide Stapling, " Journal of the American Chemical Society, 2013, 135(16):5946-5949.
Steeds et al., "Pseudotyping of VSV with Ebola virus glycoprotein is superior to HIV-1 for the assessment of neutralising antibodies," Scientific Reports, Aug. 31, 2020, 10(14289), 10 pages.
Szu et al., "Comparative immunogenicities of Vi polysaccharide-protein conjugates composed of cholera toxin or its B subunit as a carrier bound to high-or lower-molecular-weight Vi," Infection and Immunity, Dec. 1989, 57(12):3823-3827.
Szu et al., "Laboratory and Preliminary Clinical Characterization of Vi Capsular Polysaccharide-Protein Conjugate Vaccines," Infection and Immunity., Oct. 1994, 62(10):4440-4444.
Szu et al., "Relation between Structure and Immunologic Properties of the Vi Capsular Polysaccharide," Infection and Immunology, Dec. 1991, 59(12):4555-4561.
Szu et al., "Vi Capsular Polysaccharide-Protein Conjugates for Prevention of Typhoid Fever," The Journal of Experimental Medicine, Nov. 1987, 166(5):1510-1524.
Walensky et al., "Activation of Apoptosis in Vivo by a Hydrocarbon-Stapled BH3 Helix," Science, Sep. 3, 2004, 305(5689):1466-1470.
Walensky et al., Hydrocarbon-Stapled Peptides: Principles, Practice, and Progress. Journal of Medicinal Chemistry 57, 6275-6288 (2014).
Watanabe et al., "Functional Importance of the Coiled-Coil of the Ebola Virus Glycoprotein," Journal of Virology, Nov. 2000, 74(21):10194-10201.
Weissenhorn et al., "Crystal Structure of the Ebola Virus Membrane Fusion Subunit, GP2, from the Envelope Glycoprotein Ectodomain," Molecular Cell, Nov. 1998, 2(5):605-616.
West et al., "Structural basis of broad ebolavirus neutralization by a human survivor antibody," Nature Structural & Molecular Biology, Mar. 4, 2019, 26:204-212.
Williams et al., "Asymmetric Synthesis of Monosubstituted and α, α-Disubstituted α-amino Acids via Diastereoselective Glycine Enolate Alkylations," J. Am. Chem. Soc., 1991, 113(24):9276-9286.
Williams et al., "Efficient Asymmetric Synthesis of *N-tert*-Butoxycarbonyl α-Aminoacids Using 4-*tert*-Butoxycarbonyl-5, 6-Diphenylmorpholin-2-one:(R)-(N-*tert*-Butoxycarbonyl) Allylglycine: (4-Pentenoic Acid, 2-[[(1, 1-Dimethylethoxy) carbonyl] amino]-,(2 R)-)," Org. Synth., Apr. 28, 2003, 80:31-37.
Yang et al., "Calculation of protein conformation from circular dichroism," Methods Enzymol., Jan. 1986, 130:208-269.
Yang et al., "Essential Role of the Linear Ubiquitin Chain Assembly Complex in Lymphoma Revealed by Rare Germline Polymorphisms," Cancer Discovery, Apr. 2014, 4(4):480-493.
Young and Schultz, "Beyond the canonical 20 amino acids: expanding the genetic lexicon," Journal of Biological Chemistry, Apr. 9, 2010, 285(15):11039-11044.
Yu et al., "An Optimized Immunoaffinity Fluorescent Method for Natural Product Target Elucidation," Journal of Natural Products, Oct. 22, 2010, 73(10):1659-1666.

| Peptide | Sequence | Charge |
|---|---|---|
| WT EboV | HDWTKNITDKIDQIIHDFVDK | -2 SEQ ID NO: 2 |
| SEboV-1 | H*WTKNIT*KINQIIHDFVNK | +2 SEQ ID NO: 39 |
| SEboV-2 | H*WTK*ITDKINQIIHDFVNK | +1 SEQ ID NO: 29 |
| SEboV-3 | HDWTK*ITD*INQIIHDFVNK | -1 SEQ ID NO: 32 |
| SEboV-9 | HNWTK*ITN*INQIIHDFVNK | +1 SEQ ID NO: 33 |

SEboV-9: HNWTK*ITN*INQIIHDFVNK SEQ ID NO: 33

RNF31-WT: SR*LTE*IQRQRLEPFRLRLWDS SEQ ID NO: 68

Pre-incubation of virus: 25uM peptide at 37 deg (6h.p.i)

```
Sudan        GLRQLANETTQALQLFLRATTELRTYTILNRKAIDFLLRRWGGTCRILGPDCCIEPHDWT  60
Zaire        GLRQLANETTQALQLFLRATTELRTFSILNRKAIDFLLQRWGGTCHILGPDCCIEPHDWT  60
Bundibugyo   GLRQLANETTQALQLFLRATTELRTFSILNRKAIDFLLQRWGGTCHILGPDCCIEPHDWT  60
Tai_Forest   GLRQLANETTQALQLFLRATTELRTFSILNRKAIDFLLQRWGGTCHILGPDCCIEPQDWT  60
             *************************::***********:******:**********:***

Sudan        KNITDKINQIIHDF  74
Zaire        KNITDKIDQIIHDF  74
Bundibugyo   KNITDKIDQIIHDF  74
Tai_Forest   KNITDKIDQIIHDF  74
             *******:******
```

FIG. 18

SEQUENCE LISTING

```
<160> NUMBER OF SEQ ID NOS: 75

<210> SEQ ID NO 1
<211> LENGTH: 676
<212> TYPE: PRT
<213> ORGANISM: Zaire ebolavirus

<400> SEQUENCE: 1

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45
```

-continued

```
Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Val Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Gly Pro Lys Asn Ile Ser Gly
305                 310                 315                 320

Gln Ser Pro Ala Arg Thr Ser Ser Asp Pro Glu Thr Asn Thr Thr Asn
                325                 330                 335

Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
    370                 375                 380

Asp Asn Ser Thr His Asn Thr Pro Val Tyr Lys Leu Asp Ile Ser Glu
385                 390                 395                 400

Ala Thr Gln Val Gly Gln His His Arg Arg Ala Asp Asn Asp Ser Thr
                405                 410                 415

Ala Ser Asp Thr Pro Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
        435                 440                 445

Thr Thr Ser Pro Gln Asn Tyr Ser Glu Thr Ala Gly Asn Asn Asn Thr
    450                 455                 460

His His Gln Asp Thr Gly Glu Glu Ser Ala Ser Ser Gly Lys Leu Gly
```

```
465                 470                 475                 480

Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675


<210> SEQ ID NO 2
<211> LENGTH: 21
<212> TYPE: PRT
<213> ORGANISM: Zaire ebolavirus

<400> SEQUENCE: 2

His Asp Trp Thr Lys Asn Ile Thr Asp Lys Ile Asp Gln Ile Ile His
1               5                   10                  15

Asp Phe Val Asp Lys
            20


<210> SEQ ID NO 3
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

His Asp Trp Thr Lys Asn Ile Thr Asp Lys Ile Asp Gln Ile Ile His
1               5                   10                  15

Asp Phe Val Asn Lys
            20


<210> SEQ ID NO 4
<211> LENGTH: 21
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 4

His Asp Trp Thr Lys Asn Ile Thr Asp Lys Ile Asn Gln Ile Ile His
1               5                   10                  15

Asp Phe Val Asn Lys
            20


<210> SEQ ID NO 5
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

His Asn Trp Thr Lys Asn Ile Thr Asp Lys Ile Asn Gln Ile Ile His
1               5                   10                  15

Asp Phe Val Asn Lys
            20


<210> SEQ ID NO 6
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

His Asn Trp Thr Lys Asn Ile Thr Asn Lys Ile Asn Gln Ile Ile His
1               5                   10                  15

Asp Phe Val Asn Lys
            20


<210> SEQ ID NO 7
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: A non-natural amino acid with an olefinic side
      chain
<220> FEATURE:
<221> NAME/KEY: SITE
<222> LOCATION: (1)..(5)
<223> OTHER INFORMATION: /note="May or may not be cross-linked"
<220> FEATURE:
<221> NAME/KEY: MOD_RES
<222> LOCATION: (5)..(5)
<223> OTHER INFORMATION: A non-natural amino acid with an olefinic side
      chain

<400> SEQUENCE: 7

Xaa Asp Trp Thr Xaa Asn Ile Thr Asp Lys Ile Asp Gln Ile Ile His
1               5                   10                  15

Asp Phe Val Asp Lys
            20
```

```
<210> SEQ ID NO 8
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: A non-natural amino acid with an olefinic side
      chain
<220> FEATURE:
<221> NAME/KEY: SITE
<222> LOCATION: (1)..(5)
<223> OTHER INFORMATION: /note="May or may not be cross-linked"
<220> FEATURE:
<221> NAME/KEY: MOD_RES
<222> LOCATION: (5)..(5)
<223> OTHER INFORMATION: A non-natural amino acid with an olefinic side
      chain

<400> SEQUENCE: 8

Xaa Asp Trp Thr Xaa Asn Ile Thr Asp Lys Ile Asn Gln Ile Ile His
1               5                   10                  15

Asp Phe Val Asn Lys
            20


<210> SEQ ID NO 9
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: A non-natural amino acid with an olefinic side
      chain
<220> FEATURE:
<221> NAME/KEY: SITE
<222> LOCATION: (1)..(5)
<223> OTHER INFORMATION: /note="May or may not be cross-linked"
<220> FEATURE:
<221> NAME/KEY: MOD_RES
<222> LOCATION: (5)..(5)
<223> OTHER INFORMATION: A non-natural amino acid with an olefinic side
      chain

<400> SEQUENCE: 9

Xaa Asn Trp Thr Xaa Asn Ile Thr Asp Lys Ile Asn Gln Ile Ile His
1               5                   10                  15

Asp Phe Val Asn Lys
            20


<210> SEQ ID NO 10
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: A non-natural amino acid with an olefinic side
      chain
```

-continued

<220> FEATURE:
<221> NAME/KEY: SITE
<222> LOCATION: (2)..(6)
<223> OTHER INFORMATION: /note="May or may not be cross-linked"
<220> FEATURE:
<221> NAME/KEY: MOD_RES
<222> LOCATION: (6)..(6)
<223> OTHER INFORMATION: A non-natural amino acid with an olefinic side chain

<400> SEQUENCE: 10

His Xaa Trp Thr Lys Xaa Ile Thr Asp Lys Ile Asp Gln Ile Ile His
1 5 10 15

Asp Phe Val Asp Lys
20

<210> SEQ ID NO 11
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: A non-natural amino acid with an olefinic side chain
<220> FEATURE:
<221> NAME/KEY: SITE
<222> LOCATION: (2)..(6)
<223> OTHER INFORMATION: /note="May or may not be cross-linked"
<220> FEATURE:
<221> NAME/KEY: MOD_RES
<222> LOCATION: (6)..(6)
<223> OTHER INFORMATION: A non-natural amino acid with an olefinic side chain

<400> SEQUENCE: 11

His Xaa Trp Thr Lys Xaa Ile Thr Asp Lys Ile Asn Gln Ile Ile His
1 5 10 15

Asp Phe Val Asn Lys
20

<210> SEQ ID NO 12
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (5)..(5)
<223> OTHER INFORMATION: A non-natural amino acid with an olefinic side chain
<220> FEATURE:
<221> NAME/KEY: SITE
<222> LOCATION: (5)..(9)
<223> OTHER INFORMATION: /note="May or may not be cross-linked"
<220> FEATURE:
<221> NAME/KEY: MOD_RES
<222> LOCATION: (9)..(9)
<223> OTHER INFORMATION: A non-natural amino acid with an olefinic side chain

<400> SEQUENCE: 12

His Asn Trp Thr Xaa Asn Ile Thr Xaa Lys Ile Asn Gln Ile Ile His
1 5 10 15

```
Asp Phe Val Asn Lys
            20


<210> SEQ ID NO 13
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: A non-natural amino acid with an olefinic side
      chain
<220> FEATURE:
<221> NAME/KEY: SITE
<222> LOCATION: (5)..(9)
<223> OTHER INFORMATION: /note="May or may not be cross-linked"
<220> FEATURE:
<221> NAME/KEY: MOD_RES
<222> LOCATION: (9)..(9)
<223> OTHER INFORMATION: A non-natural amino acid with an olefinic side
      chain

<400> SEQUENCE: 13

His Asp Trp Thr Xaa Asn Ile Thr Xaa Lys Ile Asn Gln Ile Ile His
1               5                   10                  15

Asp Phe Val Asn Lys
            20


<210> SEQ ID NO 14
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: A non-natural amino acid with an olefinic side
      chain
<220> FEATURE:
<221> NAME/KEY: SITE
<222> LOCATION: (6)..(10)
<223> OTHER INFORMATION: /note="May or may not be cross-linked"
<220> FEATURE:
<221> NAME/KEY: MOD_RES
<222> LOCATION: (10)..(10)
<223> OTHER INFORMATION: A non-natural amino acid with an olefinic side
      chain

<400> SEQUENCE: 14

His Asp Trp Thr Lys Xaa Ile Thr Asp Xaa Ile Asn Gln Ile Ile His
1               5                   10                  15

Asp Phe Val Asn Lys
            20


<210> SEQ ID NO 15
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
```

```
<223> OTHER INFORMATION: A non-natural amino acid with an olefinic side
      chain
<220> FEATURE:
<221> NAME/KEY: SITE
<222> LOCATION: (6)..(10)
<223> OTHER INFORMATION: /note="May or may not be cross-linked"
<220> FEATURE:
<221> NAME/KEY: MOD_RES
<222> LOCATION: (10)..(10)
<223> OTHER INFORMATION: A non-natural amino acid with an olefinic side
      chain

<400> SEQUENCE: 15

His Asn Trp Thr Lys Xaa Ile Thr Asn Xaa Ile Asn Gln Ile Ile His
1               5                   10                  15

Asp Phe Val Asn Lys
            20


<210> SEQ ID NO 16
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: A non-natural amino acid with an olefinic side
      chain
<220> FEATURE:
<221> NAME/KEY: SITE
<222> LOCATION: (9)..(13)
<223> OTHER INFORMATION: /note="May or may not be cross-linked"
<220> FEATURE:
<221> NAME/KEY: MOD_RES
<222> LOCATION: (13)..(13)
<223> OTHER INFORMATION: A non-natural amino acid with an olefinic side
      chain

<400> SEQUENCE: 16

His Asp Trp Thr Lys Asn Ile Thr Xaa Lys Ile Asp Xaa Ile Ile His
1               5                   10                  15

Asp Phe Val Asp Lys
            20


<210> SEQ ID NO 17
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (12)..(12)
<223> OTHER INFORMATION: A non-natural amino acid with an olefinic side
      chain
<220> FEATURE:
<221> NAME/KEY: SITE
<222> LOCATION: (12)..(16)
<223> OTHER INFORMATION: /note="May or may not be cross-linked"
<220> FEATURE:
<221> NAME/KEY: MOD_RES
<222> LOCATION: (16)..(16)
<223> OTHER INFORMATION: A non-natural amino acid with an olefinic side
      chain

<400> SEQUENCE: 17

His Asp Trp Thr Lys Asn Ile Thr Asp Lys Ile Xaa Gln Ile Ile Xaa
```

-continued

```
1               5                   10                  15

Asp Phe Val Asp Lys
            20


<210> SEQ ID NO 18
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (13)..(13)
<223> OTHER INFORMATION: A non-natural amino acid with an olefinic side
      chain
<220> FEATURE:
<221> NAME/KEY: SITE
<222> LOCATION: (13)..(17)
<223> OTHER INFORMATION: /note="May or may not be cross-linked"
<220> FEATURE:
<221> NAME/KEY: MOD_RES
<222> LOCATION: (17)..(17)
<223> OTHER INFORMATION: A non-natural amino acid with an olefinic side
      chain

<400> SEQUENCE: 18

His Asp Trp Thr Lys Asn Ile Thr Asp Lys Ile Asp Xaa Ile Ile His
1               5                   10                  15

Xaa Phe Val Asp Lys
            20


<210> SEQ ID NO 19
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: A non-natural amino acid with an olefinic side
      chain
<220> FEATURE:
<221> NAME/KEY: SITE
<222> LOCATION: (1)..(8)
<223> OTHER INFORMATION: /note="May or may not be cross-linked"
<220> FEATURE:
<221> NAME/KEY: MOD_RES
<222> LOCATION: (8)..(8)
<223> OTHER INFORMATION: A non-natural amino acid with an olefinic side
      chain

<400> SEQUENCE: 19

Xaa Asp Trp Thr Lys Asn Ile Xaa Asp Lys Ile Asp Gln Ile Ile His
1               5                   10                  15

Asp Phe Val Asp Lys
            20


<210> SEQ ID NO 20
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

<221> NAME/KEY: MOD_RES
<222> LOCATION: (2)..(2)
<223> OTHER INFORMATION: A non-natural amino acid with an olefinic side
      chain
<220> FEATURE:
<221> NAME/KEY: SITE
<222> LOCATION: (2)..(9)
<223> OTHER INFORMATION: /note="May or may not be cross-linked"
<220> FEATURE:
<221> NAME/KEY: MOD_RES
<222> LOCATION: (9)..(9)
<223> OTHER INFORMATION: A non-natural amino acid with an olefinic side
      chain

<400> SEQUENCE: 20

His Xaa Trp Thr Lys Asn Ile Thr Xaa Lys Ile Asp Gln Ile Ile His
1               5                   10                  15

Asp Phe Val Asn Lys
            20

<210> SEQ ID NO 21
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: A non-natural amino acid with an olefinic side
      chain
<220> FEATURE:
<221> NAME/KEY: SITE
<222> LOCATION: (2)..(9)
<223> OTHER INFORMATION: /note="May or may not be cross-linked"
<220> FEATURE:
<221> NAME/KEY: MOD_RES
<222> LOCATION: (9)..(9)
<223> OTHER INFORMATION: A non-natural amino acid with an olefinic side
      chain

<400> SEQUENCE: 21

His Xaa Trp Thr Lys Asn Ile Thr Xaa Lys Ile Asn Gln Ile Ile His
1               5                   10                  15

Asp Phe Val Asn Lys
            20

<210> SEQ ID NO 22
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: A non-natural amino acid with an olefinic side
      chain
<220> FEATURE:
<221> NAME/KEY: SITE
<222> LOCATION: (6)..(13)
<223> OTHER INFORMATION: /note="May or may not be cross-linked"
<220> FEATURE:
<221> NAME/KEY: MOD_RES
<222> LOCATION: (13)..(13)
<223> OTHER INFORMATION: A non-natural amino acid with an olefinic side
      chain

<400> SEQUENCE: 22

His Asp Trp Thr Lys Xaa Ile Thr Asp Lys Ile Asp Xaa Ile Ile His
1 5 10 15

Asp Phe Val Asp Lys
20

<210> SEQ ID NO 23
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (9)..(9)
<223> OTHER INFORMATION: A non-natural amino acid with an olefinic side chain
<220> FEATURE:
<221> NAME/KEY: SITE
<222> LOCATION: (9)..(16)
<223> OTHER INFORMATION: /note="May or may not be cross-linked"
<220> FEATURE:
<221> NAME/KEY: MOD_RES
<222> LOCATION: (16)..(16)
<223> OTHER INFORMATION: A non-natural amino acid with an olefinic side chain

<400> SEQUENCE: 23

His Asp Trp Thr Lys Asn Ile Thr Xaa Lys Ile Asp Gln Ile Ile Xaa
1 5 10 15

Asp Phe Val Asp Lys
20

<210> SEQ ID NO 24
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (5)..(5)
<223> OTHER INFORMATION: A non-natural amino acid with an olefinic side chain
<220> FEATURE:
<221> NAME/KEY: SITE
<222> LOCATION: (5)..(8)
<223> OTHER INFORMATION: /note="May or may not be cross-linked"
<220> FEATURE:
<221> NAME/KEY: MOD_RES
<222> LOCATION: (8)..(8)
<223> OTHER INFORMATION: A non-natural amino acid with an olefinic side chain
<220> FEATURE:
<221> NAME/KEY: SITE
<222> LOCATION: (8)..(12)
<223> OTHER INFORMATION: /note="May or may not be cross-linked"
<220> FEATURE:
<221> NAME/KEY: MOD_RES
<222> LOCATION: (12)..(12)
<223> OTHER INFORMATION: A non-natural amino acid with an olefinic side chain

<400> SEQUENCE: 24

His Asp Trp Thr Xaa Asn Ile Xaa Asp Lys Ile Xaa Gln Ile Ile His
1 5 10 15

Asp Phe Val Asp Lys
20

```
<210> SEQ ID NO 25
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)-2-(4'-pentenyl)Alanine
<220> FEATURE:
<221> NAME/KEY: MOD_RES
<222> LOCATION: (5)..(5)
<223> OTHER INFORMATION: (S)-2-(4'-pentenyl)Alanine

<400> SEQUENCE: 25

Xaa Asp Trp Thr Xaa Asn Ile Thr Asp Lys Ile Asp Gln Ile Ile His
1               5                   10                  15

Asp Phe Val Asp Lys
            20


<210> SEQ ID NO 26
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)-2-(4'-pentenyl)Alanine
<220> FEATURE:
<221> NAME/KEY: MOD_RES
<222> LOCATION: (5)..(5)
<223> OTHER INFORMATION: (S)-2-(4'-pentenyl)Alanine

<400> SEQUENCE: 26

Xaa Asp Trp Thr Xaa Asn Ile Thr Asp Lys Ile Asn Gln Ile Ile His
1               5                   10                  15

Asp Phe Val Asn Lys
            20


<210> SEQ ID NO 27
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)-2-(4'-pentenyl)Alanine
<220> FEATURE:
<221> NAME/KEY: MOD_RES
<222> LOCATION: (5)..(5)
<223> OTHER INFORMATION: (S)-2-(4'-pentenyl)Alanine

<400> SEQUENCE: 27

Xaa Asn Trp Thr Xaa Asn Ile Thr Asp Lys Ile Asn Gln Ile Ile His
1               5                   10                  15

Asp Phe Val Asn Lys
            20
```

<210> SEQ ID NO 28
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (2)..(2)
<223> OTHER INFORMATION: (S)-2-(4'-pentenyl)Alanine
<220> FEATURE:
<221> NAME/KEY: MOD_RES
<222> LOCATION: (6)..(6)
<223> OTHER INFORMATION: (S)-2-(4'-pentenyl)Alanine

<400> SEQUENCE: 28

```
His Xaa Trp Thr Lys Xaa Ile Thr Asp Lys Ile Asp Gln Ile Ile His
1               5                   10                  15

Asp Phe Val Asp Lys
            20
```

<210> SEQ ID NO 29
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (2)..(2)
<223> OTHER INFORMATION: (S)-2-(4'-pentenyl)Alanine
<220> FEATURE:
<221> NAME/KEY: MOD_RES
<222> LOCATION: (6)..(6)
<223> OTHER INFORMATION: (S)-2-(4'-pentenyl)Alanine

<400> SEQUENCE: 29

```
His Xaa Trp Thr Lys Xaa Ile Thr Asp Lys Ile Asn Gln Ile Ile His
1               5                   10                  15

Asp Phe Val Asn Lys
            20
```

<210> SEQ ID NO 30
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (5)..(5)
<223> OTHER INFORMATION: (S)-2-(4'-pentenyl)Alanine
<220> FEATURE:
<221> NAME/KEY: MOD_RES
<222> LOCATION: (9)..(9)
<223> OTHER INFORMATION: (S)-2-(4'-pentenyl)Alanine

<400> SEQUENCE: 30

```
His Asn Trp Thr Xaa Asn Ile Thr Xaa Lys Ile Asn Gln Ile Ile His
1               5                   10                  15

Asp Phe Val Asn Lys
            20
```

```
<210> SEQ ID NO 31
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: (S)-2-(4'-pentenyl)Alanine
<220> FEATURE:
<221> NAME/KEY: MOD_RES
<222> LOCATION: (9)..(9)
<223> OTHER INFORMATION: (S)-2-(4'-pentenyl)Alanine

<400> SEQUENCE: 31

His Asp Trp Thr Xaa Asn Ile Thr Xaa Lys Ile Asn Gln Ile Ile His
1               5                   10                  15

Asp Phe Val Asn Lys
            20


<210> SEQ ID NO 32
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (S)-2-(4'-pentenyl)Alanine
<220> FEATURE:
<221> NAME/KEY: MOD_RES
<222> LOCATION: (10)..(10)
<223> OTHER INFORMATION: (S)-2-(4'-pentenyl)Alanine

<400> SEQUENCE: 32

His Asp Trp Thr Lys Xaa Ile Thr Asp Xaa Ile Asn Gln Ile Ile His
1               5                   10                  15

Asp Phe Val Asn Lys
            20


<210> SEQ ID NO 33
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (S)-2-(4'-pentenyl)Alanine
<220> FEATURE:
<221> NAME/KEY: MOD_RES
<222> LOCATION: (10)..(10)
<223> OTHER INFORMATION: (S)-2-(4'-pentenyl)Alanine

<400> SEQUENCE: 33

His Asn Trp Thr Lys Xaa Ile Thr Asn Xaa Ile Asn Gln Ile Ile His
1               5                   10                  15

Asp Phe Val Asn Lys
            20


<210> SEQ ID NO 34
```

<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: (S)-2-(4'-pentenyl)Alanine
<220> FEATURE:
<221> NAME/KEY: MOD_RES
<222> LOCATION: (13)..(13)
<223> OTHER INFORMATION: (S)-2-(4'-pentenyl)Alanine

<400> SEQUENCE: 34

His Asp Trp Thr Lys Asn Ile Thr Xaa Lys Ile Asp Xaa Ile Ile His
1               5                   10                  15

Asp Phe Val Asp Lys
            20

<210> SEQ ID NO 35
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (12)..(12)
<223> OTHER INFORMATION: (S)-2-(4'-pentenyl)Alanine
<220> FEATURE:
<221> NAME/KEY: MOD_RES
<222> LOCATION: (16)..(16)
<223> OTHER INFORMATION: (S)-2-(4'-pentenyl)Alanine

<400> SEQUENCE: 35

His Asp Trp Thr Lys Asn Ile Thr Asp Lys Ile Xaa Gln Ile Ile Xaa
1               5                   10                  15

Asp Phe Val Asp Lys
            20

<210> SEQ ID NO 36
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (13)..(13)
<223> OTHER INFORMATION: (S)-2-(4'-pentenyl)Alanine
<220> FEATURE:
<221> NAME/KEY: MOD_RES
<222> LOCATION: (17)..(17)
<223> OTHER INFORMATION: (S)-2-(4'-pentenyl)Alanine

<400> SEQUENCE: 36

His Asp Trp Thr Lys Asn Ile Thr Asp Lys Ile Asp Xaa Ile Ile His
1               5                   10                  15

Xaa Phe Val Asp Lys
            20

<210> SEQ ID NO 37
<211> LENGTH: 21

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (R)-2-(7'-octenyl)Alanine
<220> FEATURE:
<221> NAME/KEY: MOD_RES
<222> LOCATION: (8)..(8)
<223> OTHER INFORMATION: (S)-2-(4'-pentenyl)Alanine

<400> SEQUENCE: 37

Xaa Asp Trp Thr Lys Asn Ile Xaa Asp Lys Ile Asp Gln Ile Ile His
1               5                   10                  15

Asp Phe Val Asp Lys
            20


<210> SEQ ID NO 38
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (R)-2-(7'-octenyl)Alanine
<220> FEATURE:
<221> NAME/KEY: MOD_RES
<222> LOCATION: (9)..(9)
<223> OTHER INFORMATION: (S)-2-(4'-pentenyl)Alanine

<400> SEQUENCE: 38

His Xaa Trp Thr Lys Asn Ile Thr Xaa Lys Ile Asp Gln Ile Ile His
1               5                   10                  15

Asp Phe Val Asn Lys
            20


<210> SEQ ID NO 39
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (R)-2-(7'-octenyl)Alanine
<220> FEATURE:
<221> NAME/KEY: MOD_RES
<222> LOCATION: (9)..(9)
<223> OTHER INFORMATION: (S)-2-(4'-pentenyl)Alanine

<400> SEQUENCE: 39

His Xaa Trp Thr Lys Asn Ile Thr Xaa Lys Ile Asn Gln Ile Ile His
1               5                   10                  15

Asp Phe Val Asn Lys
            20


<210> SEQ ID NO 40
<211> LENGTH: 21
<212> TYPE: PRT
```

<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (6)..(6)
<223> OTHER INFORMATION: (R)-2-(7'-octenyl)Alanine
<220> FEATURE:
<221> NAME/KEY: MOD_RES
<222> LOCATION: (13)..(13)
<223> OTHER INFORMATION: (S)-2-(4'-pentenyl)Alanine

<400> SEQUENCE: 40

```
His Asp Trp Thr Lys Xaa Ile Thr Asp Lys Ile Asp Xaa Ile Ile His
1               5                   10                  15

Asp Phe Val Asp Lys
            20
```

<210> SEQ ID NO 41
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (9)..(9)
<223> OTHER INFORMATION: (R)-2-(7'-octenyl)Alanine
<220> FEATURE:
<221> NAME/KEY: MOD_RES
<222> LOCATION: (16)..(16)
<223> OTHER INFORMATION: (S)-2-(4'-pentenyl)Alanine

<400> SEQUENCE: 41

```
His Asp Trp Thr Lys Asn Ile Thr Xaa Lys Ile Asp Gln Ile Ile Xaa
1               5                   10                  15

Asp Phe Val Asp Lys
            20
```

<210> SEQ ID NO 42
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (5)..(5)
<223> OTHER INFORMATION: (S)-2-(4'-pentenyl)Alanine
<220> FEATURE:
<221> NAME/KEY: MOD_RES
<222> LOCATION: (8)..(8)
<223> OTHER INFORMATION: 2,2-bis(4-pentenyl)Glycine
<220> FEATURE:
<221> NAME/KEY: MOD_RES
<222> LOCATION: (12)..(12)
<223> OTHER INFORMATION: (S)-2-(4'-pentenyl)Alanine

<400> SEQUENCE: 42

```
His Asp Trp Thr Xaa Asn Ile Xaa Asp Lys Ile Xaa Gln Ile Ile His
1               5                   10                  15

Asp Phe Val Asp Lys
            20
```

-continued

<210> SEQ ID NO 43
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 43

Asn Ile Thr Asp Lys Ile Asp Gln Ile Ile His Asp Phe Val Asp Lys
1 5 10 15

<210> SEQ ID NO 44
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 44

Asn Ile Thr Asp Lys Ile Asn Gln Ile Ile His Asp Phe Val Asn Lys
1 5 10 15

<210> SEQ ID NO 45
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 45

Ile Thr Asp Lys Ile Asp Gln Ile Ile His Asp Phe Val Asp Lys
1 5 10 15

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 46

Ile Thr Asp Lys Ile Asn Gln Ile Ile His Asp Phe Val Asn Lys
1 5 10 15

<210> SEQ ID NO 47
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 47

His Asn Trp Thr
1

<210> SEQ ID NO 48
<211> LENGTH: 12
<212> TYPE: PRT
<213> ORGANISM: Artificial Sequence -continued
<220> FEATURE:
<221> NAME/KEY: source
<223> OTHER INFORMATION: /note="Description of Artificial Sequence:
      Synthetic peptide"

<400> SEQUENCE: 48

Lys Ile Asn Gln Ile Ile His Asp Phe Val Asn Lys
1               5                   10

<210> SEQ ID NO 49
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

His Asp Trp Thr
1

<210> SEQ ID NO 50
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

His Asp Trp Thr Lys
1               5

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ile Asn Gln Ile Ile His Asp Phe Val Asn Lys
1               5                   10

<210> SEQ ID NO 52
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

His Asn Trp Thr Lys
1               5

<210> SEQ ID NO 53
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

His Asp Trp Thr Lys Asn Ile Thr
1               5

<210> SEQ ID NO 54
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 54

Ile Ile His Asp Phe Val Asp Lys
1               5

<210> SEQ ID NO 55
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 55

His Asp Trp Thr Lys Asn Ile Thr Asp Lys Ile
1               5                   10

<210> SEQ ID NO 56
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 56

Asp Phe Val Asp Lys
1               5

<210> SEQ ID NO 57
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 57

His Asp Trp Thr Lys Asn Ile Thr Asp Lys Ile Asp
1               5                   10

<210> SEQ ID NO 58
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 58

Phe Val Asp Lys

1

<210> SEQ ID NO 59
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 59

Asp Trp Thr Lys Asn Ile
1 5

<210> SEQ ID NO 60
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 60

Asp Lys Ile Asp Gln Ile Ile His Asp Phe Val Asp Lys
1 5 10

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 61

Trp Thr Lys Asn Ile Thr
1 5

<210> SEQ ID NO 62
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 62

Lys Ile Asp Gln Ile Ile His Asp Phe Val Asn Lys
1 5 10

<210> SEQ ID NO 63
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 63

His Asp Trp Thr Lys
1 5

<210> SEQ ID NO 64

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ile Thr Asp Lys Ile Asp
1               5


<210> SEQ ID NO 65
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ile Ile His Asp Phe Val Asp Lys
1               5


<210> SEQ ID NO 66
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Lys Ile Asp Gln Ile Ile
1               5


<210> SEQ ID NO 67
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Gln Ile Ile His Asp Phe Val Asp Lys
1               5


<210> SEQ ID NO 68
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: (S)-2-(4'-pentenyl)Alanine
<220> FEATURE:
<221> NAME/KEY: MOD_RES
<222> LOCATION: (7)..(7)
<223> OTHER INFORMATION: (S)-2-(4'-pentenyl)Alanine

<400> SEQUENCE: 68

Ser Arg Xaa Leu Thr Glu Xaa Ile Gln Arg Gln Arg Leu Glu Pro Phe
```

```
1               5                   10                  15

Arg Leu Arg Leu Trp Asp Ser
            20


<210> SEQ ID NO 69
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Gly Leu Arg Gln Leu Ala Asn Glu Thr Thr Gln Ala Leu Gln Leu Phe
1               5                   10                  15

Leu Arg Ala Thr Thr Glu Leu Arg Thr Tyr Thr Ile Leu Asn Arg Lys
            20                  25                  30

Ala Ile Asp Phe Leu Leu Arg Arg Trp Gly Gly Thr Cys Arg Ile Leu
        35                  40                  45

Gly Pro Asp Cys Cys Ile Glu Pro His Asp Trp Thr Lys Asn Ile Thr
    50                  55                  60

Asp Lys Ile Asn Gln Ile Ile His Asp Phe
65                  70


<210> SEQ ID NO 70
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Gly Leu Arg Gln Leu Ala Asn Glu Thr Thr Gln Ala Leu Gln Leu Phe
1               5                   10                  15

Leu Arg Ala Thr Thr Glu Leu Arg Thr Phe Ser Ile Leu Asn Arg Lys
            20                  25                  30

Ala Ile Asp Phe Leu Leu Gln Arg Trp Gly Gly Thr Cys His Ile Leu
        35                  40                  45

Gly Pro Asp Cys Cys Ile Glu Pro His Asp Trp Thr Lys Asn Ile Thr
    50                  55                  60

Asp Lys Ile Asp Gln Ile Ile His Asp Phe
65                  70


<210> SEQ ID NO 71
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Gly Leu Arg Gln Leu Ala Asn Glu Thr Thr Gln Ala Leu Gln Leu Phe
1               5                   10                  15

Leu Arg Ala Thr Thr Glu Leu Arg Thr Phe Ser Ile Leu Asn Arg Lys
            20                  25                  30

Ala Ile Asp Phe Leu Leu Gln Arg Trp Gly Gly Thr Cys His Ile Leu
        35                  40                  45
```

```
Gly Pro Asp Cys Cys Ile Glu Pro His Asp Trp Thr Lys Asn Ile Thr
    50                  55                  60

Asp Lys Ile Asp Gln Ile Ile His Asp Phe
65                  70


<210> SEQ ID NO 72
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Gly Leu Arg Gln Leu Ala Asn Glu Thr Thr Gln Ala Leu Gln Leu Phe
1               5                   10                  15

Leu Arg Ala Thr Thr Glu Leu Arg Thr Phe Ser Ile Leu Asn Arg Lys
            20                  25                  30

Ala Ile Asp Phe Leu Leu Gln Arg Trp Gly Gly Thr Cys His Ile Leu
        35                  40                  45

Gly Pro Asp Cys Cys Ile Glu Pro Gln Asp Trp Thr Lys Asn Ile Thr
    50                  55                  60

Asp Lys Ile Asp Gln Ile Ile His Asp Phe
65                  70


<210> SEQ ID NO 73
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

His Asp Trp Thr Lys Asn Ile Thr Asp Lys Ile Asp Gln Ile Ile His
1               5                   10                  15

Asp Phe


<210> SEQ ID NO 74
<211> LENGTH: 206
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Met Gly Leu Arg Gln Leu Ala Asn Glu Thr Thr Gln Ala Leu Gln Leu
1               5                   10                  15

Phe Leu Arg Ala Thr Thr Glu Leu Arg Thr Phe Ser Ile Leu Asn Arg
            20                  25                  30

Lys Ala Ile Asp Phe Leu Leu Gln Arg Trp Gly Gly Thr Cys His Ile
        35                  40                  45

Leu Gly Pro Asp Cys Ala Ile Glu Pro His Asp Trp Thr Lys Asn Ile
    50                  55                  60

Thr Asp Lys Ile Asp Gln Ile Ile His Asp Phe Gly Ser Ser Gly Gly
65                  70                  75                  80

Leu Arg Gln Leu Ala Asn Glu Thr Thr Gln Ala Leu Gln Leu Phe Leu
```

-continued

```
                85                  90                  95

Arg Ala Thr Thr Glu Leu Arg Thr Phe Ser Ile Leu Asn Arg Lys Ala
            100                 105                 110

Ile Asp Phe Leu Leu Gln Arg Trp Gly Gly Thr Cys His Ile Leu Gly
        115                 120                 125

Pro Asp Cys Ala Ile Glu Pro His Asp Trp Thr Lys Asn Ile Thr Asp
    130                 135                 140

Lys Ile Asp Gln Ile Ile His Asp Phe Gly Ser Ser Gly Gly Leu Arg
145                 150                 155                 160

Gln Leu Ala Asn Glu Thr Thr Gln Ala Leu Gln Leu Phe Leu Arg Ala
                165                 170                 175

Thr Thr Glu Leu Arg Thr Phe Ser Ile Leu Asn Arg Lys Ala Ile Asp
            180                 185                 190

Phe Leu Leu Gln Arg Trp Gly Gly His His His His His His
        195                 200                 205


<210> SEQ ID NO 75
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 75

His His His His His His
1               5
```

ANTIVIRAL STRUCTURALLY-STABILIZED EBOLAVIRUS PEPTIDES AND USES THEREOF

CROSS-REFERENCE TO RELATED APPLICATION

This application is a U.S. national stage application of international application no. PCT/US2021/058023, filed Nov. 4, 2021, which claims the priority benefit of U.S. provisional application No. 63/110,169, filed Nov. 5, 2020, each of which is hereby incorporated by reference herein in its entirety.

SEQUENCE LISTING

The instant application contains a Sequence Listing which has been submitted electronically in ASCII format and is hereby incorporated by reference in its entirety. Said ASCII copy, created on Oct. 29, 2021, is named 00530-0373WO1_SL.txt and is 41,134 bytes in size.

TECHNICAL FIELD

This disclosure relates to structurally-stabilized Ebolavirus GP2 antiviral peptides and methods for using such peptides in the prevention and treatment of an Ebola virus infection.

BACKGROUND

Ebolaviruses (EBOV) are membrane-enveloped, negative-stranded RNA viruses of the filoviridae family. Within this genus, there are four species that are known to infect humans: Zaire ebolavirus, Bundibugyo ebolavirus, Sudan ebolavirus, and Tai Forest ebolavirus.

EBOV requires fusion of the host and virus membranes to allow for delivery of viral genetic material into the host cell. Membrane fusion in Ebola occurs in host endosomal compartments rather than on the cell surface. Upon engagement of the viral surface glycoprotein ($GP_{1,2}$) with the cell, the EBOV particle is endocytosed, and its GP is enzymatically cleaved, removing the majority of the $GP_1$ subunit and exposing the transmembrane-anchored subunit GP2. GP2 contains an N-terminal and a C-terminal helical heptad repeat (NHR and CHR, respectively). At its N-terminus, GP2 contains a fusion loop, which, upon a conformational transition, can embed into the host endosomal membrane, leading to a transient intermediate known as the “prehairpin” intermediate in which NHR and CHR are exposed and link the viral and host membranes. Upon pH-mediated maturation of the endosome, GP2 collapses into a highly stable six-helix bundle that brings the host and viral membranes into proximity, providing the driving force for membrane fusion, pore formation, and subsequent infection. The six-helix bundle contains a long, central NHR core with three shorter CHR segments packed alongside in an anti-parallel configuration, together forming a trimeric coiled-coil. An additional intramolecular disulfide bond stabilizes a helix-turn-helix motif between the NHR and CHR and is important for overall bundle stability.

EBOV infections result in severe and often fatal disease (Ebola virus Disease, EVD) in humans. Since its discovery in 1976, the virus has caused several epidemics including in Western Africa (2013-2016) and more recently in the Democratic Republic of Congo (2017-2019). Transmission occurs readily upon direct contact of mucus membranes or non-intact skin with infected body fluids or tissues. EVD is characterized by systemic dissemination of the virus, immune suppression, immune overactivation (cytokine storm), coagulation abnormalities, and tissue damage leading to organ failure and death. In EVD survivors, persistent infection in immune-privileged sites (e.g., central nervous system, eyes, male reproductive tract) occurred. Sexual transmission, male-to-female, has been reported. A number of randomized controlled trials testing preventative vaccines have been completed; however, no approved drugs are currently available for the treatment of Ebola infection. A randomized controlled trial is also underway to test several experimental therapies in addition to supportive care. These experimental therapies or other therapeutic agents are needed to treat the acute disease or RNA persistence following recovery that are easy to administer in an outbreak setting.

Accordingly, there is a need for new inhibitors of Ebola virus for both prevention and treatment.

SUMMARY

This disclosure provides structurally stabilized (e.g., stapled) alpha-helical peptides mimicking the CHR, or a portion thereof, of the EBOV GP2. These stabilized (e.g., stapled) EBOV peptides can act as direct inhibitors of EBOV, such as by blocking the virus fusion event. In certain aspects, the structurally stabilized (e.g., stapled) EBOV peptides bind to the EBOV GP2 fusion complex. Without being bound by any theory, the stabilized EBOV peptides provided herein inhibit the formation of the GP2 six-helix bundle, thereby inhibiting the EBOV fusion process. This disclosure also features methods for using such stabilized peptides alone or in combination with other therapeutic agents in the prevention of EBOV infection and in the treatment or prevention of EVD.

Provided herein is a peptide comprising an amino acid sequence: (a) HNWTK$X_1$ITN$X_2$INQIIHDFVNK, wherein each of $X_1$ and $X_2$ is independently a stapling amino acid (SEQ ID NO:15); (b) HDWTK$X_1$ITD$X_2$INQIIHDFVNK, wherein each of $X_1$ and $X_2$ is independently a stapling amino acid (SEQ ID NO:14); (c) $X_1$DWT$X_2$NITDKIDQIIHDFVDK, wherein each of $X_1$ and $X_2$ is independently a stapling amino acid (SEQ ID NO:7); (d) $X_1$DWT$X_2$NITDKINQIIHDFVNK, wherein each of $X_1$ and $X_2$ is independently a stapling amino acid (SEQ ID NO:8); (e) $X_1$NWT$X_2$NITDKINQIIHDFVNK, wherein each of $X_1$ and $X_2$ is independently a stapling amino acid (SEQ ID NO:9); (f) H$X_1$WTK$X_2$ITDKIDQIIHDFVDK, wherein each of $X_1$ and $X_2$ is independently a stapling amino acid (SEQ ID NO:10); (g) H$X_1$WTK$X_2$ITDKINQIIHDFVNK, wherein each of $X_1$ and $X_2$ is independently a stapling amino acid (SEQ ID NO:11); (h) HNWT$X_1$NIT$X_2$KINQIIHDFVNK, wherein each of $X_1$ and $X_2$ is independently a stapling amino acid (SEQ ID NO:12); (i) HDWT$X_1$NIT$X_2$KINQIIHDFVNK, wherein each of $X_1$ and $X_2$ is independently a stapling amino acid (SEQ ID NO:13); (j) HDWTKNIT$X_1$KID$X_2$IIHDFVDK, wherein each of $X_1$ and $X_2$ is independently a stapling amino acid (SEQ ID NO:16); (k) HDWTKNITDKI$X_1$QII$X_2$DFVDK, wherein each of $X_1$ and $X_2$ is independently a stapling amino acid (SEQ ID NO:17); (l) HDWTKNITDKID$X_1$IIH$X_2$FVDK, wherein each of $X_1$ and $X_2$ is independently a stapling amino acid (SEQ ID NO:18); (m) $X_1$DWTKNI$X_2$DKIDQIIHDFVDK, wherein each of $X_1$ and $X_2$ is independently a stapling amino acid (SEQ ID NO:19); (n) H$X_1$WTKNIT$X_2$KIDQIIHDFVNK, wherein each of $X_1$ and $X_2$ is independently a stapling amino acid (SEQ ID NO:20); (o) $HX_1WTKNITX_2KINQIIHDFVNK$, wherein each of $X_1$ and $X_2$ is independently a stapling amino acid (SEQ ID NO:21); (p) $HDWTKX_1ITDKIDX_2IIHDFVDK$, wherein each of $X_1$ and $X_2$ is independently a stapling amino acid (SEQ ID NO:22); (q) $HDWTKNITX_1KIDQIIX_2DFVDK$, wherein each of $X_1$ and $X_2$ is independently a stapling amino acid (SEQ ID NO:23); or (r) $HDWTX_1NIX_2DKIX_3QIIHDFVDK$, wherein each of $X_1$, $X_2$, and $X_3$ is independently a stitching amino acid (SEQ ID NO:24); and wherein the peptide binds a 5 helix bundle or fusion bundle intermediate of EBOV GP2. In some instances, the peptide further prevents or blocks fusion of an Ebola virus membrane and a host membrane. In some instances, the peptide is 21 to 50 amino acids in length. The amino acid sequence of any one of SEQ ID NOs:7-23 can be trimmed down at the N and/or C-terminus by 1, 2, 3, 4, 5, 6, or 7 amino acids (e.g., 1, 2, 3, 4, 5, 6, or 7 amino acids can be removed from the N- and/or C-terminus of the amino acid sequence of any one of SEQ ID NOs:7-23) while still permitting the resulting peptide to bind a 5 helix bundle or fusion bundle intermediate of EBOV GP2 and prevent or block fusion of an Ebola virus membrane and a host membrane.

Also provided herein is a structurally stabilized peptide comprising an amino acid sequence: (a) $HNWTKX_1ITNX_2INQIIHDFVNK$, wherein each of $X_1$ and $X_2$ is independently a stapling amino acid (SEQ ID NO:15); (b) $HDWTKX_1ITDX_2INQIIHDFVNK$, wherein each of $X_1$ and $X_2$ is independently a stapling amino acid (SEQ ID NO:14); (c) $X_1DWTX_2NITDKIDQIIHDFVDK$, wherein each of $X_1$ and $X_2$ is independently a stapling amino acid (SEQ ID NO:7); (d) $X_1DWTX_2NITDKINQIIHDFVNK$, wherein each of $X_1$ and $X_2$ is independently a stapling amino acid (SEQ ID NO:8); (e) $X_1NWTX_2NITDKINQIIHDFVNK$, wherein each of $X_1$ and $X_2$ is independently a stapling amino acid (SEQ ID NO:9); (f) $HX_1WTKX_2ITDKIDQIIHDFVDK$, wherein each of $X_1$ and $X_2$ is independently a stapling amino acid (SEQ ID NO:10); (g) $HX_1WTKX_2ITDKINQIIHDFVNK$, wherein each of $X_1$ and $X_2$ is independently a stapling amino acid (SEQ ID NO:11); (h) $HNWTX_1NITX_2KINQIIHDFVNK$, wherein each of $X_1$ and $X_2$ is independently a stapling amino acid (SEQ ID NO:12); (i) $HDWTX_1NITX_2KINQIIHDFVNK$, wherein each of $X_1$ and $X_2$ is independently a stapling amino acid (SEQ ID NO:13); (j) $HDWTKNITX_1KIDX_2IIHDFVDK$, wherein each of $X_1$ and $X_2$ is independently a stapling amino acid (SEQ ID NO:16); (k) $HDWTKNITDKIX_1QIIX_2DFVDK$, wherein each of $X_1$ and $X_2$ is independently a stapling amino acid (SEQ ID NO:17); (1) $HDWTKNITDKIDX_1IIHX_2FVDK$, wherein each of $X_1$ and $X_2$ is independently a stapling amino acid (SEQ ID NO:18); (m) $X_1DWTKNIX_2DKIDQIIHDFVDK$, wherein each of $X_1$ and $X_2$ is independently a stapling amino acid (SEQ ID NO:19); (n) $HX_1WTKNITX_2KIDQIIHDFVNK$, wherein each of $X_1$ and $X_2$ is independently a stapling amino acid (SEQ ID NO:20); (o) $HX_1WTKNITX_2KINQIIHDFVNK$, wherein each of $X_1$ and $X_2$ is independently a stapling amino acid (SEQ ID NO:21); (p) $HDWTKX_1ITDKIDX_2IIHDFVDK$, wherein each of $X_1$ and $X_2$ is independently a stapling amino acid (SEQ ID NO:22); (q) $HDWTKNITX_1KIDQIIX_2DFVDK$, wherein each of $X_1$ and $X_2$ is independently a stapling amino acid (SEQ ID NO:23); or (r) $HDWTX_1NIX_2DKIX_3QIIHDFVDK$, wherein each of $X_1$, $X_2$, and $X_3$ is independently a stitching amino acid (SEQ ID NO:24); wherein the structurally stabilized peptide is stapled or stitched; and wherein the peptide binds a 5 helix bundle or fusion bundle intermediate of EBOV GP2. In some instances, the peptide further prevents or blocks fusion of an Ebola virus membrane and a host membrane. In some instances, the structurally stabilized peptide is 21-50 amino acids in length. The amino acid sequence of any one of SEQ ID NOs:7-23 can be trimmed down at the N and/or C-terminus by 1, 2, 3, 4, 5, 6, or 7 amino acids (e.g., 1, 2, 3, 4, 5, 6, or 7 amino acids can be removed from the N- and/or C-terminus of the amino acid sequence of any one of SEQ ID NOs:7-23) while still permitting the resulting structurally stabilized peptide to bind a 5 helix bundle or fusion bundle intermediate of EBOV GP2 and prevent or block fusion of an Ebola virus membrane and a host membrane.

In some instances, the structurally stabilized peptide comprises the amino acid sequence: (a) $HNWTKX_1ITNX_2INQIIHDFVNK$, wherein each of $X_1$ and $X_2$ is independently a stapling amino acid (SEQ ID NO:15), and wherein the sidechains of $X_1$ and $X_2$ are cross-linked to each other; (b) $HDWTKX_1ITDX_2INQIIHDFVNK$, wherein each of $X_1$ and $X_2$ is independently a stapling amino acid (SEQ ID NO:14), and wherein the sidechains of $X_1$ and $X_2$ are cross-linked to each other; (c) $X_1DWTX_2NITDKIDQIIHDFVDK$, wherein each of $X_1$ and $X_2$ is independently a stapling amino acid (SEQ ID NO:7), and wherein the sidechains of X1 and X2 are cross-linked to each other; (d) $X_1DWTX_2NITDKINQIIHDFVNK$, wherein each of $X_1$ and $X_2$ is independently a stapling amino acid (SEQ ID NO:8), and wherein the sidechains of X1 and X2 are cross-linked to each other; (e) $X_1NWTX_2NITDKINQIIHDFVNK$, wherein each of $X_1$ and $X_2$ is independently a stapling amino acid (SEQ ID NO:9), and wherein the sidechains of X1 and X2 are cross-linked to each other; (f) $HX_1WTKX_2ITDKIDQIIHDFVDK$, wherein each of $X_1$ and $X_2$ is independently a stapling amino acid (SEQ ID NO:10), and wherein the sidechains of X1 and X2 are cross-linked to each other; (g) $HX_1WTKX_2ITDKINQIIHDFVNK$, wherein each of $X_1$ and $X_2$ is independently a stapling amino acid (SEQ ID NO:11), and wherein the sidechains of X1 and X2 are cross-linked to each other; (h) $HNWTX_1NITX_2KINQIIHDFVNK$, wherein each of $X_1$ and $X_2$ is independently a stapling amino acid (SEQ ID NO:12), and wherein the sidechains of X1 and X2 are cross-linked to each other; (i) $HDWTX_1NITX_2KINQIIHDFVNK$, wherein each of $X_1$ and $X_2$ is independently a stapling amino acid (SEQ ID NO:13), and wherein the sidechains of X1 and X2 are cross-linked to each other; (j) $HDWTKNITX_1KIDX_2IIHDFVDK$, wherein each of $X_1$ and $X_2$ is independently a stapling amino acid (SEQ ID NO:16), and wherein the sidechains of X1 and X2 are cross-linked to each other; (k) $HDWTKNITDKIX_1QIIX_2DFVDK$, wherein each of $X_1$ and $X_2$ is independently a stapling amino acid (SEQ ID NO:17), and wherein the sidechains of X1 and X2 are cross-linked to each other; (1) $HDWTKNITDKIDX_1IIHX_2FVDK$, wherein each of $X_1$ and $X_2$ is independently a stapling amino acid (SEQ ID NO:18), and wherein the sidechains of X1 and X2 are cross-linked to each other; (m) $X_1DWTKNIX_2DKIDQIIHDFVDK$, wherein each of $X_1$ and $X_2$ is independently a stapling amino acid (SEQ ID NO:19), and wherein the sidechains of X1 and X2 are cross-linked to each other; (n) $HX_1WTKNITX_2KIDQIIHDFVNK$, wherein each of $X_1$ and $X_2$ is independently a stapling amino acid (SEQ ID NO:20), and wherein the sidechains of X1 and X2 are cross-linked to each other; (o) $HX_1WTKNITX_2KINQIIHDFVNK$, wherein each of $X_1$ and $X_2$ is independently a stapling amino acid (SEQ ID NO:21), and wherein the sidechains of X1 and X2 are cross-linked to each other; (p) HDWTK$X_1$ITDKID$X_2$IIHDFVDK, wherein each of $X_1$ and $X_2$ is independently a stapling amino acid (SEQ ID NO:22), and wherein the sidechains of X1 and X2 are cross-linked to each other; (q) HDWTKNIT$X_1$KIDQII$X_2$DFVDK, wherein each of $X_1$ and $X_2$ is independently a stapling amino acid (SEQ ID NO:23), and wherein the sidechains of X1 and X2 are cross-linked to each other; or (r) HDWT$X_1$NI$X_2$DKI$X_3$QIIHDFVDK, wherein each of $X_1$, $X_2$, and $X_3$ is independently a stitching amino acid (SEQ ID NO:24), and wherein the sidechains of $X_1$ and $X_2$ are cross-linked to each other and the sidechains of $X_2$ and $X_3$ are cross-linked to each other. In some instances, the structurally stabilized peptide is 21-50 amino acids in length. The amino acid sequence of any one of SEQ ID NOs:7-23 can be trimmed down at the N and/or C-terminus by 1, 2, 3, 4, 5, 6, or 7 amino acids (e.g., 1, 2, 3, 4, 5, 6, or 7 amino acids can be removed from the N- and/or C-terminus of the amino acid sequence of any one of SEQ ID NOs:7-23) while still permitting the resulting structurally stabilized peptide to bind a 5 helix bundle or fusion bundle intermediate of EBOV GP2 and prevent or block fusion of an Ebola virus membrane and a host membrane.

Also provided herein is a structurally stabilized peptide comprising the Formula:

Formula (I)

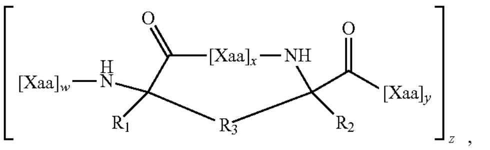

or a pharmaceutically acceptable salt thereof, wherein: each $R_1$ and $R_2$ is H or a $C_1$ to $C_{10}$ alkyl, alkenyl, alkynyl, arylalkyl, cycloalkylalkyl, heteroarylalkyl, or heterocyclylalkyl, any of which is substituted or unsubstituted; each $R_3$ is independently alkylene, alkenylene, or alkynylene, any of which is substituted or unsubstituted; z is 1, 2, 3, 4, 5, 6, 7, 8, 9, or 10; and (a) each $[Xaa]_w$ is HDWTK (SEQ ID NO:50), each $[Xaa]_x$ is ITD, and each $[Xaa]_y$ is INQIIHDFVNK (SEQ ID NO:51); (b) each $[Xaa]_w$ is HDWT (SEQ ID NO:49), each $[Xaa]_x$ is NIT, and each $[Xaa]_y$ is KINQIIHDFVNK (SEQ ID NO:48); (c) each $[Xaa]_w$ is absent, each $[Xaa]_x$ is DWT, and each $[Xaa]_y$ is NITDKIDQIIHDFVDK (SEQ ID NO:43); (d) each $[Xaa]_w$ is absent, each $[Xaa]_x$ is DWT, and each $[Xaa]_y$ is NITDKINQIIHDFVNK (SEQ ID NO:44); (e) each $[Xaa]_w$ is absent, each $[Xaa]_x$ is NWT, and each $[Xaa]_y$ is NITDKINQIIHDFVNK (SEQ ID NO:44); (f) each $[Xaa]_w$ is H, each $[Xaa]_x$ is WTK, and each $[Xaa]_y$ is ITDKIDQIIHDFVDK (SEQ ID NO:45); (g) each $[Xaa]_w$ is H, each $[Xaa]_x$ is WTK, and each $[Xaa]_y$ is ITDKINQIIHDFVNK (SEQ ID NO:46); (h) each $[Xaa]_w$ is HNWT (SEQ ID NO:47), each $[Xaa]_x$ is NIT, and each $[Xaa]_y$ is KINQIIHDFVNK (SEQ ID NO:48); (i) each $[Xaa]_w$ is HNWTK (SEQ ID NO:52), each $[Xaa]_x$ is ITN, and each $[Xaa]_y$ is INQIIHDFVNK (SEQ ID NO:51); (j) each $[Xaa]_w$ is HDWTKNIT (SEQ ID NO:53), each $[Xaa]_x$ is KID, and each $[Xaa]_y$ is IIHDFVDK (SEQ ID NO:54); (k) each $[Xaa]_w$ is HDWTKNITDKI (SEQ ID NO:55), each $[Xaa]_x$ is QII, and each $[Xaa]_y$ is DFVDK (SEQ ID NO:56); (l) each $[Xaa]_w$ is HDWTKNITDKID (SEQ ID NO:57), each $[Xaa]_x$ is IIH, and each $[Xaa]_y$ is FVDK (SEQ ID NO:58); (m) each $[Xaa]_w$ is absent, each $[Xaa]_x$ is DWTKNI (SEQ ID NO:59), and each $[Xaa]_y$ is DKIDQIIHDFVDK (SEQ ID NO:60); (n) each $[Xaa]_w$ is H, each $[Xaa]_x$ is WTKNIT (SEQ ID NO:61), and each $[Xaa]_y$ is KIDQIIHDFVNK (SEQ ID NO:62); (o) each $[Xaa]_w$ is H, each $[Xaa]_x$ is WTKNIT (SEQ ID NO:61), and each $[Xaa]_y$ is KINQIIHDFVNK (SEQ ID NO:48); (p) each $[Xaa]_w$ is HDWTK (SEQ ID NO:63), each $[Xaa]_x$ is ITDKID (SEQ ID NO:64), and each $[Xaa]_y$ is IIHDFVDK (SEQ ID NO:65); or (q) each $[Xaa]_w$ is HDWTKNIT (SEQ ID NO:53), each $[Xaa]_x$ is KIDQII (SEQ ID NO:66), and each $[Xaa]_y$ is DFVDK (SEQ ID NO:56); wherein the peptide binds a 5 helix bundle or fusion bundle intermediate of EBOV GP2. In some instances, the peptide further prevents or blocks fusion of an Ebola virus membrane and a host membrane. In some instances, wherein $R_1$ is an alkyl. In some instances, $R_1$ is a methyl group. In some instances, $R_2$ is an alkyl. In some instances, $R_2$ is a methyl group. In some instances, $R_3$ is an alkenyl. In some instances, $R_3$ is 4-octenyl. In some instances, $R_1$ is a methyl group, $R_3$ is 4-octenyl, and $R_2$ is a methyl group. In some instances, the structurally stabilized peptide or pharmaceutically acceptance salt thereof is 21 to 50 amino acids in length. The peptide of Formula (I) can be trimmed down at the N and/or C-terminus by 1, 2, 3, 4, 5, 6, or 7 amino acids (e.g., 1, 2, 3, 4, 5, 6, or 7 amino acids can be removed from the N- and/or C-terminus of the amino acid sequence of any one of SEQ ID NOs:7-23) while still permitting the resulting peptide to bind a 5 helix bundle or fusion bundle intermediate of EBOV GP2 and prevent or block fusion of an Ebola virus membrane and a host membrane. In some instances, the pharmaceutically acceptable salt is an acetate, a sulfate, or a chloride.

Also provided herein is a structurally stabilized peptide comprising the Formula:

Formula (II)

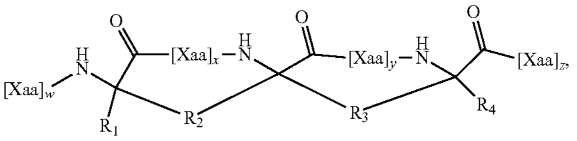

or a pharmaceutically acceptable salt thereof, wherein: $[Xaa]_w$ is HDWT (SEQ ID NO:49); $[Xaa]_x$ is NI; $[Xaa]_y$ is DKI; and $[Xaa]_z$ is QIIHDFVDK (SEQ ID NO:67); each $R_1$ and $R_4$ is independently H, alkyl, alkenyl, alkynyl, arylalkyl, cycloalkylalkyl, heteroarylalkyl, or heterocyclylalkyl, any of which is substituted or unsubstituted; each $R_2$ and $R_3$ is independently alkylene, alkenylene, or alkynylene, any of which is substituted or unsubstituted; and wherein the structurally stabilized peptide binds to a 5 helix bundle of EBOV GP2 or fusion bundle intermediate of EBOV GP2. In some instances, the structurally stabilized peptide further prevents or blocks fusion of an Ebola virus membrane and a host membrane. In some instances, $R_1$ is an alkyl. In some instances, $R_1$ is a methyl group. In some instances, $R_4$ is an alkyl. In some instances, $R_4$ is a methyl group. In some instances, $R_2$ is an alkenyl. In some instances, $R_2$ is 4-octenyl. In some instances, $R_3$ is an alkenyl. In some instances, $R_3$ is 4-octenyl. In some instances, $R_1$ is a methyl group, $R_2$ is 4-octenyl, $R_3$ is 4-octenyl, and $R_4$ is a methyl group. In some instances, the structurally stabilized peptide or pharmaceutically acceptable salt thereof is 21 to 50 amino acids in length. The peptide of Formula (II) can be trimmed down at the N and/or C-terminus by 1, 2, 3, 4, 5, 6, or 7 amino acids (e.g., 1, 2, 3, 4, 5, 6, or 7 amino acids can be removed from the N- and/or C-terminus of the amino acid sequence of any one of SEQ ID NOs:7-23) while still permitting the resulting peptide to bind a 5 helix bundle or fusion bundle intermediate of EBOV GP2 and prevent or block fusion of an Ebola virus membrane and a host membrane. In some instances, the pharmaceutically acceptable salt is an acetate, a sulfate, or a chloride.

Also provided herein is a structurally stabilized peptide comprising an amino acid sequence set forth in SEQ ID NO:2 with 2 to 12 amino acid substitutions and 0 to 5 amino acid deletions from the N- and/or C-terminus of the amino acid sequence set forth in SEQ ID NO:2, wherein at least two amino acids separated by 2, 3, or 6 amino acids are substituted with non-natural amino acids with olefinic side chains, and at least one aspartic acid in SEQ ID NO:2 is substituted by asparagine, wherein the peptide binds to a 5 helix bundle or fusion bundle intermediate of EBOV GP2. In some instances, the structural stabilization comprises a hydrocarbon staple. In some instances, the peptide further prevents or blocks fusion of an Ebola virus membrane 10 and a host membrane. In some instances, the 2 to 12 amino acid substitutions are at one or more positions selected from the group consisting of position 2, 5, 6, 8, 9, 10 12, 17, and 20 (numbering with respect to SEQ ID NO:2). In some instances, the amino acids at one of these sets of positions (relative to SEQ ID NO:2) are replaced by non-natural amino acids with olefinic side chains: (i) 2 and 6; (ii) 2 and 9; (iii) 6 and 10; (iv) 1 and 8; (v) 5, 8, and 12; or (vi) 12 and 16. In some instances, the amino acids at one or more of positions 2, 9, 12, 17 or 20 are replaced by asparagine. In some instances, the amino acids at one or more of positions 2, 9, 12, or 20 are replaced by asparagine.

Also provided herein is an internally cross-linked peptide comprising a cross-linked form of the aforementioned peptide. In some instances, the internally cross-linked peptide has one or more of the following properties: (i) alpha-helical; (ii) retains alpha-helical propensity at pH 4.6; (iii) interferes with assembly of the six-helix-bundle post-fusion complex; (iv) is cell permeable in eukaryotic cells (e.g., is taken up by endosomes); (v) is positively charged; (vi) localizes with late endosomes; and/or (vii) displays antiviral activity against EBOV.

Also provided herein is a structurally stabilized peptide of a polypeptide, the structurally stabilized peptide comprising the Formula:

Formula (I)

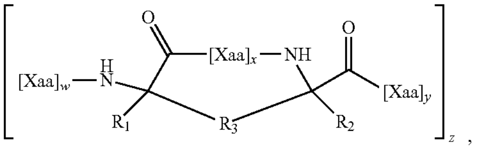

or a pharmaceutically acceptable salt thereof, wherein: the polypeptide comprises the amino acid sequence set forth in SEQ ID NO:2 with 2 to 12 amino acid substitutions and 0 to 5 amino acid deletions from the N- and/or C-terminus of the amino acid sequence set forth in SEQ ID NO:2, wherein at least two amino acids separated by 2, 3, or 6 amino acids are replaced by non-natural amino acids with olefinic side chains; each $R_1$ and $R_2$ is H or a $C_1$ to $C_{10}$ alkyl, alkenyl, alkynyl, arylalkyl, cycloalkylalkyl, heteroarylalkyl, or heterocyclylalkyl, any of which is substituted or unsubstituted; each $R_3$ is independently alkylene, alkenylene, or alkynylene, any of which is substituted or unsubstituted; z is 1, 2, or 3; and w+y is 12, 13, 14, 15, 16, 17, 18, 19, or 20; and the structurally stabilized peptide binds to a 5 helix bundle or fusion bundle intermediate of EBOV GP2 and has one or more of the following properties: (i) alpha-helical; (ii) retains alpha-helical propensity at pH 4.6; (iii) interferes with assembly of the six-helix-bundle post-fusion complex; (iv) is cell permeable in eukaryotic cells (e.g., is taken up by endosomes); (v) is positively charged; (vi) localizes with late endosomes; (vii) displays antiviral activity against EBOV; and/or (viii) prevents or blocks fusion of an Ebola virus membrane and a host membrane. In some instances, $[Xaa]_x$ is DWTKNI (SEQ ID NO: 59), WTKNIT (SEQ ID NO: 61), WTK, ITD, ITN, or QII, with 0 to 3 amino acid substitutions. In some instances, the pharmaceutically acceptable salt is an acetate, a sulfate, or a chloride.

Also provided herein is a structurally stabilized peptide of a polypeptide, the structurally stabilized peptide comprising the Formula:

Formula (II)

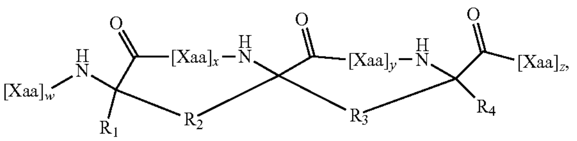

or a pharmaceutically acceptable salt thereof, wherein: the polypeptide comprises the amino acid sequence set forth in SEQ ID NO:2 with 3 to 12 amino acid substitutions and 0 to 5 amino acid deletions from the N- and/or C-terminus of the amino acid sequence set forth in SEQ ID NO:2, wherein at least three amino acids are replaced by non-natural amino acids with olefinic side chains; each $R_1$ and $R_4$ is independently H, alkyl, alkenyl, alkynyl, arylalkyl, cycloalkylalkyl, heteroarylalkyl, or heterocyclylalkyl, any of which is substituted or unsubstituted; each $R_2$ and $R_3$ is independently alkylene, alkenylene, or alkynylene, any of which is substituted or unsubstituted; x and y are 2, 3, or 6; w+z is 8, 9, 10, 11, 12, 13, 14, or 15; and wherein the structurally stabilized peptide binds to a 5 helix bundle or fusion bundle intermediate of EBOV GP2 and has one or more of the following properties: (i) alpha-helical; (ii) retains alpha-helical propensity at pH 4.6; (iii) interferes with assembly of the six-helix-bundle post-fusion complex; (iv) is cell permeable in eukaryotic cells (e.g., is taken up by endosomes); (v) is positively charged; (vi) localizes with late endosomes; (vii) displays antiviral activity against EBOV; and/or (viii) prevents or blocks fusion of an Ebola virus membrane and a host membrane. In some instances, $[Xaa]_w$ is HDWT (SEQ ID NO:49) with 0 to 1 amino acid substitution; $[Xaa]_x$ is NI; $[Xaa]_y$ is DKI with 0 to 1 amino acid substitution; and $[Xaa]_z$ is QIIHDFVDK (SEQ ID NO:67) with 0 to 3 amino acid substitutions. In some instances, the pharmaceutically acceptable salt is an acetate, a sulfate, or a chloride.

Also provided herein is a structurally stabilized (e.g., stapled or stitched) peptide comprising an amino acid sequence set forth in any one of SEQ ID NOs:2-6 except with 2 to 13 amino acid substitutions and 0 to 5 deletions from the N- and/or C-terminus of the amino acid sequence set forth in any one of SEQ ID NOs:2-6, wherein at least 2 of the 2 to 13 amino acid substitutions are separated by 2, 3, or 6 amino acids and are substituted with non-natural amino acids with olefinic side chains, wherein the at least 2 non-natural amino acids with olefinic side chains are cross-linked to each other, wherein the structurally stabilized peptide does not comprise the amino acids corresponding to positions 610-612 of SEQ ID NO:1, and wherein the peptide binds to a 5 helix bundle or fusion bundle intermediate of EBOV GP2. In some instances, the structurally stabilized peptide is 21 to 50 amino acids in length. In some instances, the structurally stabilized peptide is 21 amino acids in length. In some instances, the structurally stabilized peptide prevents or blocks fusion of an Ebola virus membrane and a host membrane. In some instances, the 2 to 13 amino acid substitutions are at one or more positions selected from the group consisting of position 2, 5, 6, 8, 9, 10 12, 17, and 20 of any one of SEQ ID NOs:2-6. In some instances, the at least 2 non-natural amino acids with olefinic side chains are at positions (relative to any one of SEQ ID NOs:2-6): (i) 2 and 6; (ii) 2 and 9; (iii) 6 and 10; (iv) 1 and 8; (v) (vi) 5, 8, and 12; or (vii) 12 and 16. In some instances, the structurally stabilized peptide has one or more of the following properties: (i) is alpha-helical; (ii) retains alpha-helical propensity at pH 4.6; (iii) interferes with assembly of the six-helix-bundle post-fusion complex; (iv) is cell permeable in eukaryotic cells; (v) is positively charged; (vi) localizes with late endosomes; and/or (vii) displays antiviral activity against EBOV.

In some instances, the aforementioned peptide or structurally stabilized peptide does not comprise one or more (e.g., 1, 2, 3, or 4) of the amino acids corresponding to positions 615, 616, 630, and 631 of the amino acid sequence set forth in SEQ ID NO:1. For example, in some instances, the aforementioned peptide or structurally stabilized peptide does not comprise the amino acids corresponding to positions 615, 616, 630, and 631 of the amino acid sequence set forth in SEQ ID NO:1. As another example, in some instances, the aforementioned peptide or structurally stabilized peptide does not comprise the amino acids corresponding to positions 615 and 616 of the amino acid sequence set forth in SEQ ID NO:1. As another example, in some instances, the aforementioned peptide or structurally stabilized peptide does not comprise the amino acids corresponding to positions 630 and 631 of the amino acid sequence set forth in SEQ ID NO:1. In some instances, the aforementioned peptide or structurally stabilized peptide does not contain the amino acid sequence IEP (corresponding to positions 610-612 of SEQ ID NO:1). In some instances, the aforementioned peptide or structurally stabilized peptide does not contain the amino acid sequence IGI at the N-terminus. In some instances, the aforementioned peptide or structurally stabilized peptide does not contain the amino acid sequence TLPD (corresponding to positions 634-637 of SEQ ID NO:1). In some instances, the aforementioned peptide or structurally stabilized peptide does not contain the amino acid sequence TLPDQG (corresponding to positions 634-639 of SEQ ID NO:1).

In some instances, the aforementioned peptide or structurally stabilized peptide comprises one or more (e.g., 1, 2, 3, 4, 5, 6, 7, 8, 9, 10, 11, or 12) of the amino acids corresponding to amino acids W615, T616, N618, I619, K622, I623, Q625, I626, I627, D629, F630, and V631 (numbered according to SEQ ID NO:1), or conservative amino acid substitutions thereof.

In some instances, the aforementioned peptide or structurally stabilized peptide comprises a conservative amino acid substitution at one or more (e.g., 1, 2, 3, 4, or 5) amino acids corresponding to amino acids K617, T620, D621, D624, and H628 (numbered according to SEQ ID NO:1). In some instances, the aforementioned peptide or structurally stabilized peptide comprises a non-conservative amino acid substitution at one or more (e.g., 1, 2, 3, 4, or 5) amino acids corresponding to amino acids K617, T620, D621, D624, and H628 (numbered according to SEQ ID NO:1).

Also provided herein is a pharmaceutical composition comprising an aforementioned peptide and a pharmaceutically acceptable carrier.

Also provided herein is a pharmaceutical composition comprising an aforementioned structurally stabilized peptide and a pharmaceutically acceptable carrier.

Also provided herein is a method of treating an Ebolavirus infection in a subject in need thereof, the method comprising administering to the subject a therapeutically-effective amount of an aforementioned structurally stabilized peptide. In some instances, the Ebolavirus infection is an infection with a Zaire ebolavirus, a Tai Forest ebolavirus, a Sudan ebolavirus or a Bundibugyo ebolavirus. In some instances, the subject is a human. In some instances the subject is a non-human primate. In some instances, the subject is a fruit bat.

Also provided herein is a method of preventing an Ebolavirus infection in a subject in need thereof, the method comprising administering to the subject a therapeutically-effective amount of an aforementioned structurally stabilized peptide. In some instances, the Ebolavirus infection is an infection with a Zaire ebolavirus, a Tai Forest ebolavirus, a Sudan ebolavirus or a Bundibugyo ebolavirus. In some instances, the subject is a human. In some instances the subject is a non-human primate. In some instances, the subject is a fruit bat.

Also provided herein is a method of treating an Ebolavirus disease in a subject in need thereof, the method comprising administering to the subject a therapeutically-effective amount of an aforementioned structurally stabilized peptide. In some instances, the Ebolavirus disease is caused by an infection with a Zaire ebolavirus, a Tai Forest ebolavirus, a Sudan ebolavirus or a Bundibugyo ebolavirus. In some instances, the subject is a human. In some instances the subject is a non-human primate. In some instances, the subject is a fruit bat.

Also provided herein is a method of preventing an Ebolavirus disease in a subject in need thereof, the method comprising administering to the subject a therapeutically-effective amount of an aforementioned structurally stabilized peptide. In some instances, the Ebolavirus disease is caused by an infection with a Zaire ebolavirus, a Tai Forest ebolavirus, a Sudan ebolavirus or a Bundibugyo ebolavirus. In some instances, the subject is a human. In some instances the subject is anon-human primate. In some instances, the subject is a fruit bat.

Also provided herein is a method of preventing transmission of an Ebolavirus infection from a first subject to a second subject, the method comprising administering to the first subject a therapeutically-effective amount of an aforementioned structurally stabilized peptide, wherein the first subject is a human or a non-human primate or a fruit bat. In some instances, the second subject is a human.

Also provided herein is a method of making a structurally stabilized peptide, the method comprising: (a) providing a peptide having the sequence set forth in any one of SEQ ID NOs:7-42, or an aforementioned peptide, and (b) cross-linking the peptide to make a structurally stabilized peptide; and optionally, further comprising formulating the structurally stabilized peptide into a pharmaceutical composition.

BRIEF DESCRIPTION OF THE DRAWINGS

FIG. 18 shows an alignment of exemplary amino acid sequences for the HR1 (NHR) and HR2 (CHR) separated by a GG linker for the Zaire ebolavirus, Tai Forest ebolavirus, Bundibugyo ebolavirus, and Sudan ebolavirus species. SEQ ID NOs: 69-72 (from top to bottom, respectively)

DETAILED DESCRIPTION

Figure 1:
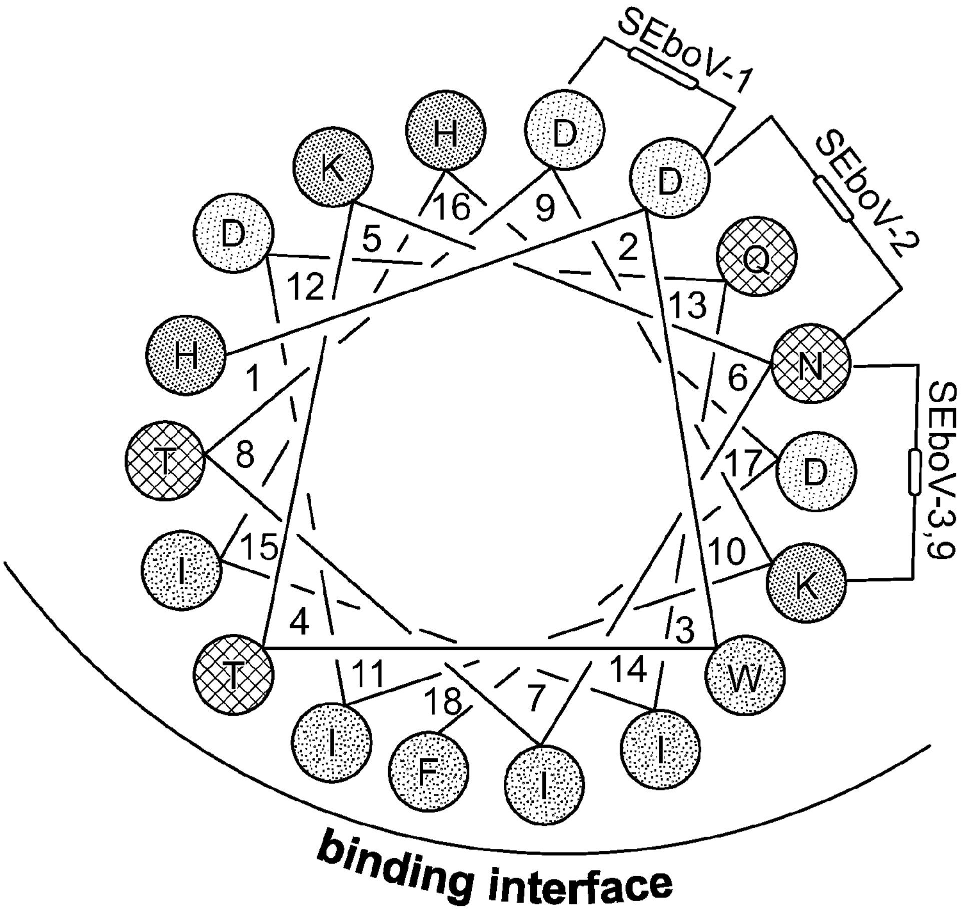
FIG. 1 depicts a helical wheel of residues 613-630 contained within the synthesized peptides containing amino acids 613-633 of EBOV GP2 (SEQ ID NO: 1).

Fusion of the host and EBOV membranes is required for delivery of EBOV genetic material into the host cell. Membrane fusion in Ebola occurs in host endosomal compartments rather than on the cell surface. Upon engagement of the viral surface glycoprotein (GP1,2) with the cell, the EBOV particle is endocytosed, and its GP is enzymatically cleaved, removing the majority of the GPT subunit and exposing the transmembrane-anchored subunit GP2. GP2 contains an N-terminal and a C-terminal helical heptad repeat (NHR and CHR, respectively). At its N-terminus, GP2 contains a fusion loop, which, upon a conformational transition, can embed into the host endosomal membrane, leading to a transient intermediate known as the "prehairpin" intermediate in which NHR and CHR are exposed and link the viral and host membranes. Upon pH-mediated maturation of the endosome, GP2 collapses into a highly stable six-helix bundle that brings the host and viral membranes into proximity, providing the driving force for membrane fusion, pore formation, and subsequent infection. The six-helix bundle contains a long, central NHR core with three shorter CHR segments packed alongside in an anti-parallel configuration, together forming a trimeric coiled-coil. An additional intramolecular disulfide bond stabilizes a helix-turn-helix motif between the NHR and CHR and is important for overall bundle stability.

This disclosure provides structurally stabilized (e.g., stapled) alpha-helical peptides mimicking the CHR, or a portion thereof, of the EBOV GP2. These stabilized (e.g., stapled) EBOV peptides can act as direct inhibitors of EBOV, such as by blocking the virus fusion event. In certain aspects, the structurally stabilized (e.g., stapled) EBOV peptides bind to the EBOV GP2 fusion complex. Without being bound by any theory, the stabilized EBOV peptides provided herein inhibit the formation of the GP2 six-helix bundle, thereby inhibiting the EBOV fusion process. This disclosure also features methods for using such stabilized peptides alone or in combination with other therapeutic agents in the prevention of EBOV infection and in the treatment or prevention of EVD.

Ebola Virus GP2 Peptides

The amino acid sequence of an exemplary Ebola virus GP2 protein of the Zaire species is provided below (GenBank Accession No. AK184258):

(SEQ ID NO: 1)
```
  1 MGVTGILQLP RDRFKRTSFF LWVIILFQRT FSIPLGVIHN STLQVSDVDK LVCRDKLSST

 61 NQLRSVGLNL EGNGVATDVP SVTKRWGFRS GVPPKVVNYE AGEWAENCYN LEIKKPDGSE

121 CLPAAPDGIR GFPRCRYVHK VSGTGPCAGD FAFHKEGAFF LYDRLASTVI YRGTTFAEGV

181 VAFLILPQAK KDFFSSHPLR EPVNATEDPS SGYYSTTIRY QATGFGTNET EYLFEVDNLT

241 YVQLESRFTP QFLLQLNETI YASGKRSNTT GKLIWKVNPE IDTTIGEWAF WETKKNLTRK

301 IRSEELSFTA VSNGPKNISG QSPARTSSDP ETNTTNEDHK IMASENSSAM VQVHSQGRKA

361 AVSHLTTLAT ISTSPQPPTT KTGPDNSTHN TPVYKLDISE ATQVGQHHRR ADNDSTASDT

421 PPATTAAGPL KAENTNTSKS ADSLDLATTT SPQNYSETAG NNNTHHQDTG EESASSGKLG

481 LITNTIAGVA GLITGGRRTR REVIVNAQPK CNPNLHYWTT QDEGAAIGLA WIPYFGPAAE

541 GIYIEGLMHN QDGLICGLRQ LANETTQALQ LFLRATTELR TFSILNRKAI DFLLQRWGGT

601 CHILGPDCCI EPHDWTKNIT DKIDQIIHDF VDKTLPDQGD NDNWWTGWRQ WIPAGIGVTG

661 VIIAVIALFC ICKFVF.
```

GP2 contains an N-terminal helical heptad repeat and a C-terminal helical heptad repeat (NHR and CHR, respectively), separated by a turn/linker. In some instances, the EBOV GP2 NHR comprises amino acid residues 557-597 of the amino acid sequence set forth in SEQ ID NO:1. In some instances, the EBOV GP2 NHR comprises amino acid residues 554-595 of the amino acid sequence set forth in SEQ ID NO:1. In some instances, the turn/linker separating the EBOV GP2 NHR and EBOV GP2 CHR comprises amino acids 598-612 of the amino acid sequence set forth in SEQ ID NO:1. In some instances, the turn/linker separating the EBOV GP2 NHR and EBOV GP2 CHR comprises amino acids 596-614 of the amino acid sequence set forth in SEQ ID NO:1. In some instances, the EBOV CHR comprises amino acids 613-633 of the amino acid sequence set forth in SEQ ID NO:1. In some instances, the EBOV GP2 CHR comprises amino acids 615-631 of the amino acid sequence set forth in SEQ ID NO:1. In some instances, an EBOV GP2 CHR peptide comprises the amino acid sequence HDWTKNITDKIDQIIHDFVDK (SEQ ID NO:2). In some instances, an EBOV GP2 CHR peptide consists of the amino acid sequence HDWTKNITDKIDQIIHDFVDK (SEQ ID NO:2). In some instances, an EBOV GP2 CHR peptide comprises the amino acid sequence HDWTKNIT DKIDQIIHDF (SEQ ID NO:73). In some instances, an EBOV GP2 CHR peptide consists of the amino acid sequence HDWTKNIT DKIDQIIHDF (SEQ ID NO:73). At its N-terminus, GP2 contains a fusion loop, which, upon a conformational transition, can embed into the host endosomal membrane, leading to a transient intermediate known as the "prehairpin" intermediate in which NHR and CHR are exposed and link the viral and host membranes. Upon pH-mediated maturation of the endosome, GP2 collapses into a highly stable six-helix bundle that brings the host and viral membranes into proximity, providing the driving force for membrane fusion, pore formation, and subsequent infection. The six-helix bundle contains a long, central NHR core with three shorter CHR segments packed alongside in an anti-parallel configuration, together forming a trimeric coiled-coil. An additional intramolecular disulfide bond stabilizes a helix-turn-helix motif between the NHR and CHR and is important for overall bundle stability.

The GP2 proteins among the different Ebolavirus species have high homology. See FIG. 18 for an alignment of exemplary amino acid sequences for the HR1 (NHR) and HR2 (CHR) separated by a GG linker for the Zaire ebolavirus, Tai Forest ebolavirus, Bundibugyo ebolavirus, and Sudan ebolavirus species. The amino acid sequence of an exemplary heptad repeat 1 (HR1, forming part of the NHR) and heptad repeat 2 (HR2, forming part of the CHR) separated by a GG linker for Zaire ebolavirus species is provided below:

(SEQ ID NO: 70)
```
GLRQLANETTQALQLFLRATTELRTFSILNRKAIDFLLQRWGGTCHILGP

DCCIEPHDWTKNITDKIDQIIHDF.
```

The amino acid sequence of an exemplary HR1 (NHR) and HR2 (CHR) separated by a GG linker for Tai Forest ebolavirus species is provided below:

(SEQ ID NO: 72)
```
GLRQLANETTQALQLFLRATTELRTFSILNRKAIDFLLQRWGGTCHILGP

DCCIEPQDWTKNITDKIDQIIHDF.
```

The amino acid sequence of an exemplary HR1 (NHR) and HR2 (CHR) separated by a GG linker for Bundibugyo ebolavirus species is provided below:

(SEQ ID NO: 71)
```
GLRQLANETTQALQLFLRATTELRTFSILNRKAIDFLLQRWGGTCHILGP

DCCIEPHDWTKNITDKIDQIIHDF.
```

The amino acid sequence of an exemplary HR1 (NHR) and HR2 (CHR) separated by a GG linker for Sudan ebolavirus species is provided below:

(SEQ ID NO: 69)
```
GLRQLANETTQALQLFLRATTELRTYTILNRKAIDFLLRRWGGTCRILGP

DCCIEPHDWTKNITDKINQIIHDF.
```

In some instances, an EBOV GP2 CHR peptide comprises the amino acid sequence of SEQ ID NO:73, except that it contains a Q at position 1 of SEQ ID NO:73. In some instances, an EBOV GP2 CHR peptide comprises the amino acid sequence of SEQ ID NO:73, except that it contains an N at position 11 of SEQ ID NO:73.

The EBOV GP2 CHR contains multiple hydrophobic residues at its binding interface with the EBOV GP2 NHR (see FIG. 1). Without being bound by any particular theory, these residues are predicted to provide the driving force for the cooperative formation of the six-helix bundle required for EBOV fusion with the host cell. Amino acids corresponding to Trp615, Thr616, Ile619, Ile623, Ile626, Ile627, and Phe630 of SEQ ID NO:1 (i.e., positions 3, 4, 7, 11, 14, 15, and 18 of SEQ ID NO:2) are predicted to interact with EBOV GP2 NHR and are thus referred to herein as "NHR-interacting residues". Amino acids corresponding to His613, Asp614, Lys617, Asn618, Thr620, Asp621, Lys622, Asp624, Gln625, His628, Asp629, Val631, Asp632, and Lys633 (i.e., positions 1, 2, 5, 6, 8-10, 12, 13, 16, 17, 19, 20, and 21 of SEQ ID NO:2) are predicted to not interact with EBOV GP2 NHR and thus are referred to as "non-NHR-interacting residues".

An overall positive charge in solution may modulate or enhance the cell permeability of stapled peptides (e.g., the ability to be taken up by endosomes). The EBOV GP2 CHR peptide having the amino acid sequence set forth in SEQ ID NO:2 has a charge of −2 at physiological pH. To engineer EBOV GP2 CHR peptides having a positive charge, one or more aspartic acid residues in the EBOV GP2 CHR peptide can be replaced with a positively charged or neutral amino acid, such as, e.g., arginine, histidine, or lysine. In some instances, one, two, three, four, or all five of the aspartic acid residues in an EBOV GP2 CHR peptide (e.g., in a peptide comprising or consisting of the amino acid sequence of SEQ ID NO:2) are replaced with a positively charged amino acid. In some instances, one, two, three, four, or all five of the aspartic acid residues in an EBOV GP2 CHR peptide (e.g., in a peptide comprising or consisting of the amino acid sequence of SEQ ID NO:2) are replaced with aspartic acid's isosteric counterpart, asparagine. In some instances, one or more (e.g., 1, 2, 3, 4, 5, 6, 7) of the NHR-interacting residues in an EBOV GP2 CHR peptide are replaced with an arginine, histidine, or lysine. In some instances, one, two, three, four, five, six, seven, eight, nine, 10, 11, 12, 13, or 14 of the non-NHR-interacting residues in an EBOV GP2 CHR peptide are replaced with an arginine, histidine, or a lysine. In some instances, the overall charge of an EBOV GP2 CHR peptide is −3 to +3. In some instances, the overall charge of an EBOV GP2 CHR peptide is −2 to +2. In some instances, the overall charge of an EBOV GP2 CHR peptide is −1 to +3. In some instances, the overall charge of an EBOV GP2 CHR peptide is 0 to +3. In some instances, the overall charge of an EBOV GP2 CHR peptide is 0 to +2.

In certain instances, also provided herein are peptides comprising a modified amino acid sequence of an EBOV GP2 CHR peptide described herein. In some cases, the peptides are modified to introduce moieties (e.g., non-natural amino acids with olefinic side chains) that permit structural stabilization to the peptide (e.g., to maintain alpha-helicity of the peptide). The structural stabilization may be by, e.g., "stapling" or "stitching" the peptide. In some cases, the staple or stitch is a hydrocarbon staple or stitch. The modification(s) to introduce structural stabilization (e.g., internal cross-linking, e.g., stapling, stitching) into the EBOV GP2 CHR peptides described herein may be positioned on the face of the EBOV GP2 CHR peptide that does not interact with EBOV GP2 NHR (i.e., the face of the EBOV GP2 CHR peptide that does not comprise one or more NHR-interacting residues). Alternatively, the modification(s) to introduce stabilization (e.g., internal cross-linking, e.g., stapling or stitching) into the EBOV GP2 CHR peptides described herein may be positioned on the face of the EBOV GP2 CHR peptide that does interact with EBOV GP2 NHR (i.e., the face of the EBOV GP2 CHR peptide that comprises one or more NHR-interacting residues). In some cases, an EBOV GP2 CHR peptide is stabilized by introducing a staple or stitch (e.g., a hydrocarbon staple or stitch) at the interface of the NHR-interacting and NHR-non-interacting faces of the EBOV GP2 CHR (i.e., on a face of the EBOV GP2 CHR peptide comprising one or more NHR-interacting residues and one or more non-NHR-interacting residues). In some instances, the modifications to introduce structural stabilization (e.g., internal cross-linking, e.g., stapling or stitching) into the EBOV GP2 CHR peptides described herein—e.g., substitution of two or more amino acids with non-natural amino acids with olefinic side chains—are positioned at the amino acid positions in the EBOV GP2 peptide corresponding to residues:

(i) 1 and 5 of SEQ ID NO:2;
(ii) 2 and 6 of SEQ ID NO:2;
(iii) 5 and 9 of SEQ ID NO:2;
(iv) 6 and 10 of SEQ ID NO: 2;
(v) 9 and 13 of SEQ ID NO:2;
(vi) 12 and 16 of SEQ ID NO: 2;
(vii) 13 and 17 of SEQ ID NO: 2;
(viii) 1 and 8 of SEQ ID NO: 2;
(ix) 2 and 9 of SEQ ID NO:2;
(x) 6 and 13 of SEQ ID NO:2;
(xi) 9 and 16 of SEQ ID NO:2; or
(xii) 5, 8, and 12 of SEQ ID NO: 2.

In certain instances, the EBOV GP2 CHR peptides described herein may also contain one or more (e.g., 1, 2, 3, 4, 5, 6, 7) additional amino acid substitutions (relative to the wild type EBOV GP2 CHR peptide sequence (e.g., SEQ ID NO:2)), e.g., one or more (e.g., 1, 2, 3, 4, 5, 6, 7) conservative and/or non-conservative amino acid substitutions. In certain instances, these additional substitution(s) are of amino acids that directly interact with the EBOV GP2 NHR (e.g., any one or more of amino acids corresponding to Trp3, Thr4, Ile7, Ile11, Ile14, Ile15, and Phe18 of SEQ ID NO:2). In certain instances, these additional substitution(s) are of amino acids that do not directly interact with the EBOV GP2 NHR (e.g., are not any one or more of amino acids corresponding to Trp3, Thr4, Ile7, Ile11, Ile14, Ile15, and Phe18 of SEQ ID NO:2 or are any one of amino acids corresponding to His1, Asp2, Lys5, Asn6, Thr8, Asp9, Lys10, Asp12, Gln13, His16, Asp17, Val19, Asp20, and Lys21 of SEQ ID NO:2). In certain instances, these additional substitution(s) are of aspartic acid residues. In certain instances, these additional substitutions are one or more (e.g., 1, 2, 3, 4, 5) of amino acids corresponding to Asp2, Asp9, Asp12, Asp17, and Asp20 of SEQ ID NO:2. In certain instances, the additional substitution(s) comprise substitution(s) with Asn (N) at one or more of amino acids corresponding to Asp2, Asp9, Asp12, Asp17, and Asp20 of SEQ ID NO:2 (i.e., one or more of the following substitutions: D2N, D9N, D12N, D17N, and D20N, numbered according to SEQ ID NO:2). In certain instances, the additional substitution comprises substitution with Asn (N) at an amino acid corresponding to Asp20 of SEQ ID NO:2 (i.e., the following substitution: D20N, numbered according to SEQ ID NO:2). In certain instances, the additional substitutions comprise substitutions with Asn (N) at amino acids corresponding to Asp12 and Asp20 of SEQ ID NO:2 (i.e., the following substitutions: D12N and D20N, numbered according to SEQ ID NO:2). In certain instances, the additional substitutions comprise substitutions with Asn (N) at amino acids corresponding to Asp2, Asp12, and Asp20 of SEQ ID NO:2 (i.e., the following substitutions: D2N, D12N, and D20N, numbered according to SEQ ID NO:2). In certain instances, the additional substitutions comprise substitutions with Asn (N) at amino acids corresponding to Asp2, Asp9, Asp12, and Asp20 of SEQ ID NO:2 (i.e., the following substitutions: D2N, D9N, D12N, and D20N, numbered according to SEQ ID NO:2). In certain instances, these additional substitutions are of both amino acids that directly interact with EBOV GP2 NHR and amino acids that do not directly interact with EBOV GP2 NHR. In certain instances, the EBOV GP2 CHR peptides described herein may also contain one or more (e.g., 1, 2, 3, 4, 5, 6, 7, 8, 9, 10) deletions from the N- and/or C-terminus of the EBOV GP2 CHR. For example, the EBOV GP2 CHR peptides may be 5 or more (e.g., 5, 6, 7, 8, 9, 10, 11, 12, 13, 14 15, 16, 17, 18, 19, 20, or 21) amino acids in length. In certain instances, the EBOV GP2 CHR peptides are 5-21 (i.e., 5, 6, 7, 8, 9, 10, 11, 12, 13, 14, 15, 16, 17, 18, 19, 20, or 21) amino acids in length. In certain instances, the EBOV GP2 CHR peptides are 10-21 (i.e., 10, 11, 12, 13, 14, 15, 16, 17, 18, 19, 20, or 21) amino acids in length. In certain instances, EBOV GP2 CHR peptides are 15-21 (i.e., 15, 16, 17, 18, 19, 20, or 21) amino acids in length. In certain instances, the EBOV GP2 CHR peptides are 5-30 (i.e., 5, 6, 7, 8, 9, 10, 11, 12, 13, 14, 15, 16, 17, 18, 19, 20, 21, 22, 23, 24, 25, 26, 27, 28, 29, or 30) amino acids in length. In certain instances, the EBOV GP2 CHR peptides are 10-30 (i.e., 10, 11, 12, 13, 14, 15, 16, 17, 18, 19, 20, 21, 22, 23, 24, 25, 26, 27, 28, 29, or 30) amino acids in length. In certain instances, EBOV GP2 CHR peptides are 15-30 (i.e., 15, 16, 17, 18, 19, 20, 21, 22, 23, 24, 25, 26, 27, 28, 29, or 30) amino acids in length. In certain instances, EBOV GP2 CHR peptides are 13 amino acids in length. In certain instances, the EBOV GP2 CHR peptides are 21 amino acids in length. In certain instances, the EBOV GP2 CHR peptides do not contain the amino acid sequence IEP (corresponding to positions 610-612 of SEQ ID NO:1). In certain instances, the EBOV GP2 CHR peptides do not contain the amino acid sequence IGI at the N-terminus. In certain instances, the EBOV GP2 CHR peptides do not contain the amino acid sequence TLPD (corresponding to positions 634-637 of SEQ ID NO:1). In certain instances, the EBOV GP2 CHR peptides do not contain the amino acid sequence TLPDQG (corresponding to positions 634-639 of SEQ ID NO:1).

In certain instances, the EBOV GP2 CHR peptides of this disclosure can have 1, 2, 3, 4, 5, 6, 7, 8, 9, 10, 11, 12, or 13 amino acid substitutions in any one of SEQ ID NOs:2-6 (e.g., 1, 2, 3, 4, 5, 6, 7, 8, 9, 10, 11, 12, or 13 amino acids are conservatively or non-conservatively substituted). For example, in certain instances, the EBOV GP2 CHR peptide of this disclosure comprises a modified amino acid sequence of the sequence set forth in SEQ ID NO:2, wherein the modified amino acid sequence comprises SEQ ID NO:2 having 1, 2, 3, 4, 5, 6, 7, 8, 9, 10, 11, 12, or 13 amino acid substitutions in the SEQ ID NO:2 sequence (e.g., the modified amino acid sequence comprises SEQ ID NO:2, except that 1, 2, 3, 4, 5, 6, 7, 8, 9, 10, 11, 12, or 13 amino acids of SEQ ID NO:2 are conservatively or non-conservatively substituted). In another example, in certain instances, the EBOV GP2 CHR peptide of this disclosure comprises a modified amino acid sequence of the sequence set forth in SEQ ID NO:3, wherein the modified amino acid sequence comprises SEQ ID NO:3 having 1, 2, 3, 4, 5, 6, 7, 8, 9, 10, 11, 12, or 13 amino acid substitutions in the SEQ ID NO:3 sequence (e.g., the modified amino acid sequence comprises SEQ ID NO:3, except that 1, 2, 3, 4, 5, 6, 7, 8, 9, 10, 11, 12, or 13 amino acids of SEQ ID NO:3 are conservatively or non-conservatively substituted). In another example, in certain instances, the EBOV GP2 CHR peptide of this disclosure comprises a modified amino acid sequence of the sequence set forth in SEQ ID NO:4, wherein the modified amino acid sequence comprises SEQ ID NO:4 having 1, 2, 3, 4, 5, 6, 7, 8, 9, 10, 11, 12, or 13 amino acid substitutions in the SEQ ID NO:4 sequence (e.g., the modified amino acid sequence comprises SEQ ID NO:4, except that 1, 2, 3, 4, 5, 6, 7, 8, 9, 10, 11, 12, or 13 amino acids of SEQ ID NO:4 are conservatively or non-conservatively substituted). In yet another example, in certain instances, the EBOV GP2 CHR peptide of this disclosure comprises a modified amino acid sequence of the sequence set forth in SEQ ID NO:5, wherein the modified amino acid sequence comprises SEQ ID NO:5 having 1, 2, 3, 4, 5, 6, 7, 8, 9, 10, 11, 12, or 13 amino acid substitutions in the SEQ ID NO:5 sequence (e.g., the modified amino acid sequence comprises SEQ ID NO:5, except that 1, 2, 3, 4, 5, 6, 7, 8, 9, 10, 11, 12, or 13 amino acids of SEQ ID NO:5 are conservatively or non-conservatively substituted). In yet another example, in certain instances, the EBOV GP2 CHR peptide of this disclosure comprises a modified amino acid sequence of the sequence set forth in SEQ ID NO:6, wherein the modified amino acid sequence comprises SEQ ID NO:6 having 1, 2, 3, 4, 5, 6, 7, 8, 9, 10, 11, 12, or 13 amino acid substitutions in the SEQ ID NO:6 sequence (e.g., the modified amino acid sequence comprises SEQ ID NO:6, except that 1, 2, 3, 4, 5, 6, 7, 8, 9, 10, 11, 12, or 13 amino acids of SEQ ID NO:6 are conservatively or non-conservatively substituted). A "conservative amino acid substitution" means that the substitution replaces one amino acid with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), aromatic side chains (e.g., tyrosine, phenylalanine, tryptophan, histidine), and acidic side chains and their amides (e.g., aspartic acid, glutamic acid, asparagine, glutamine). In some instances, one to three amino acids of any one of SEQ ID NOs:2-6 are substituted. The amino acid substitutions in any one of SEQ ID NOs:2-6 can be of amino acids that NHR-interacting residues or non-NHR-interacting residues. Much greater variability is permitted in the EBOV GP2 CHR amino acids that do not engage in direct interaction with EBOV GP2 NHR (i.e., non-NHR-interacting residues). In fact, just about every one of the non-NHR-interacting residues can be substituted (e.g., conservative or non-conservative amino acid substitutions or substitution with alanine). In certain instances, one, two, or three NHR-interacting residues are substituted with another amino acid. In some instances, the substitution(s) is/are a conservative amino acid substitution. In other instances, the substitution(s) is/are a non-conservative amino acid substitution. In some instances, where there are more than one amino acid substitutions, the substitutions are both conservative and non-conservative amino acid substitutions. In some instances, where there are more than one amino acid substitutions, each of the substitutions are conservative amino acid substitutions. In some cases, where one to three amino acids (e.g., 1, 2, or 3) of any one of SEQ ID NOs:2-6 are substituted, the substitutions are all of non-NHR-interacting residues. In some cases, where one to three amino acids (e.g., 1, 2, or 3) of any one of SEQ ID NOs:2-6 are substituted, the substitutions are all of NHR-interacting residues. In some cases, where one to three amino acids (e.g., 1, 2, or 3) of any one of SEQ ID NOs:2-6 are substituted, the substitutions are of both non-NHR-interacting residues and NHR-interacting residues. In certain instances, the substituted amino acid(s) are selected from the group consisting of L-Ala, D-Ala, Aib, Sar, Ser, a substituted alanine, or a substituted glycine derivative.

In some instances, the EBOV GP2 CHR peptides of this disclosure comprise one or more (e.g., 1, 2, 3, 4, 5, 6, 7, 8, 9, 10, 11, or 12) of the amino acids corresponding to amino acids W615, T616, N618, I619, K622, I623, Q625, I626, I627, D629, F630, and V631 (numbered according to SEQ ID NO:1), or conservative amino acid substitutions thereof.

In some instances, the EBOV GP2 CHR peptides of this disclosure comprise a conservative amino acid substitution at one or more (e.g., 1, 2, 3, 4, or 5) amino acids corresponding to amino acids K617, T620, D621, D624, and H628 (numbered according to SEQ ID NO:1). In some instances, the EBOV GP2 CHR peptides of this disclosure comprise a non-conservative amino acid substitution at one or more (e.g., 1, 2, 3, 4, or 5) amino acids corresponding to amino acids K617, T620, D621, D624, and H628 (numbered according to SEQ ID NO:1).

In some instances, the EBOV GP2 CHR peptides of this disclosure do not comprise one or more (e.g., 1, 2, 3, or 4) of the amino acids corresponding to positions 615, 616, 630, and 631 of the amino acid sequence set forth in SEQ ID NO:1. For example, in some instances, the EBOV GP2 CHR peptides of this disclosure do not comprise the amino acids corresponding to positions 615, 616, 630, and 631 of the amino acid sequence set forth in SEQ ID NO:1. As another example, in some instances, the EBOV GP2 CHR peptides of this disclosure do not comprise the amino acids corresponding to positions 615 and 616 of the amino acid sequence set forth in SEQ ID NO:1. As another example, in some instances, the EBOV GP2 CHR peptides of this disclosure do not comprise the amino acids corresponding to positions 630 and 631 of the amino acid sequence set forth in SEQ ID NO:1. In certain instances, the EBOV GP2 CHR peptides of this disclosure can have 1, 2, 3, 4, or 5, amino acids removed/deleted from the C-terminus of the sequence set forth in any one of SEQ ID NOs:2-6. In certain instances, the EBOV GP2 CHR peptides of this disclosure can have 1, 2, 3, 4, or 5, amino acid removed/deleted from the N-terminus of the sequence set forth in any one of SEQ ID NOs:2-6. In certain instances, these removed amino acids can be replaced with 1-6 (e.g., 1, 2, 3, 4, 5, or 6) amino acids selected from the group consisting of L-Ala, D-Ala, Aib, Sar, Ser, a substituted alanine, or a substituted glycine derivative.

The disclosure also encompasses EBOV GP2 CHR peptides that are at least 14% (e.g., at least 14 to 50%, at least 14 to 45%, at least 14 to 40%, at least 14 to 35%, at least 14 to 30%, at least 14 to 25%, at least 14 to 20%, at least 20% to 50%, at least 20% to 45%, at least 20% to 40%, at least 20% to 35%, at least 20% to 30%, at least 20% to 25%, at least 15%, at least 20%, at least 27%, at least 34%, at least 40% at least 45%, at least 50%, at least 55%, at least 60%, at least 65%, at least 70%, at least 75%, at least 80%, at least 85%, at least 90%, at least 95%, at least 98%, at least 99%, or 100%) identical to any one of SEQ ID NOs:2-6. In some instances, the at least 14% identity is at the binding interface as shown in FIG. 1. The variability in amino acid sequence of any one of SEQ ID NOs:2-6 can be on one or both the NHR-interacting side and non-NHR-interacting side of the alpha helix. Just about every one of the non-NHR-interacting residues can be varied. The NHR-interacting residues can also be varied. In specific instances, the EBOV GP2 CHR peptide comprises an amino acid sequence that is at least 90% identical to any one of SEQ ID NOs:2-6. In specific instances, the EBOV GP2 CHR peptide comprises an amino acid sequence that is at least 95%, at least 96%, at least 97%, at least 98%, at least 99% identical to any one of SEQ ID NOs:2-6. In specific instances, the EBOV GP2 CHR peptide consists of the amino acid sequence of any one of SEQ ID NOs:2-6. Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred instance, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

In certain instances, the EBOV GP2 CHR peptide is a variant having an amino acid sequence set forth in Table 1 below. In certain instances, the EBOV GP2 CHR peptide is a variant having an amino acid sequence set forth in Table 1 below, except that it lacks the three C-terminal amino acids in the sequences in Table 1 below.

TABLE 1

Exemplary EBOV GP2 CHR peptide variants with mutations relative to SEQ ID NO: 2 shown in bold.

| SEQ ID NO | Description | Sequence |
|---|---|---|
| 2 | EBOV GP2 CHR | HDWTKNITDKIDQIIHDFVDK |
| 3 | EBOV GP2 CHR (D20N) | HDWTKNITDKIDQIIHDFV**N**K |
| 4 | EBOV GP2 CHR (D12N, D20N) | HDWTKNITDKI**N**QIIHDFV**N**K |
| 5 | EBOV GP2 CHR (D2N, D12N, D20N) | H**N**WTKNITDKI**N**QIIHDFV**N**K |
| 6 | EBOV GP2 CHR (D2N, D9N, D12N, D20N) | H**N**WTKNIT**N**KI**N**QIIHDFV**N**K |

The EBOV GP2 CHR peptides described herein can be optimized for therapeutic use. For example, if any of the above-described EBOV GP2 CHR peptides cause membrane disruption (cell lysis), the peptides can be optimized by lowering the overall peptide hydrophobicity. This can for example be achieved by substituting especially hydrophobic residues with an amino acid with lower hydrophobicity (e.g., alanine). Membrane disruption can also be lowered by reducing the overall positive charge of the peptide. This can be accomplished by substituting basic residues with uncharged or acidic residues. In certain instances, both the overall peptide hydrophobicity and the overall positive charge of the peptide are lowered. In some instances, the overall charge of an EBOV GP2 CHR peptide is −3 to +3. In some instances, the overall charge of an EBOV GP2 CHR peptide is −2 to +2. In some instances, the overall charge of an EBOV GP2 CHR peptide is −1 to +3. In some instances, the overall charge of an EBOV GP2 CHR peptide is 0 to +3. In some instances, the overall charge of an EBOV GP2 CHR peptide is 0 to +2.

In certain instances, each of the EBOV GP2 CHR peptides described above binds to a 5 helix bundle of EBOV GP2 or fusion bundle intermediate of EBOV GP2. In certain instances, each of the EBOV GP2 CHR peptides described above binds to a 5 helix bundle of EBOV GP2 or fusion bundle intermediate of EBOV GP2 and prevents or blocks fusion of an Ebola virus membrane and a host membrane.

Methods of determining whether a peptide (e.g., a structurally stabilized peptide described herein) binds to a 5 helix bundle or a fusion bundle intermediate of EBOV GP2 are known in the art, such as, high resolution clear native electrophoresis (hrCNE). See, e.g., the working Examples section below and Harrison et al., Protein Science, 2011, 20:1587-1596, which is incorporated by reference herein in its entirety. For instance, a tagged (e.g., hexa-histidine (SEQ ID NO:75) tagged) EBOV GP2 ectodomain construct that lacks one of the CHR helices in the post-fusion complex (e.g., a construct having the amino acid sequence MGLRQLANETTQALQLFLRATTELRTFSILNRKAID-FLLQRWGGTCHILGPDC AIEPHDWTKNITD-KIDQIIHDFGSSGGLRQLANETTQALQLFLRAT-TELRTFSIL NRKAIDFLLQRWGGTCHILGPDCAIEPHDWTKNITD-KIDQIIHDFGSSGGLRQL ANETTQALQLFLRAT-TELRTFSILNRKAIDFLLQRWGGHHHHHH (SEQ ID NO:74)) is expressed and incubated with a labeled (e.g., FITC-labeled) control peptide (e.g., a peptide comprising the amino acid sequence of SEQ ID NO:2) or a labeled (e.g., FITC-labeled) test peptide (e.g., a structurally-stabilized peptide described herein) at 37° C. for, e.g., 30 minutes. After incubation, the mixture is analyzed by native PAGE electrophoresis and the native PAGE gel is imaged in a fluorescence scanner to detect the migration of the labeled species and immunoblotted to reveal the location of the tagged EBOV GP2 ectodomain construct. Co-migration of the labeled test peptide and the tagged EBOV GP2 ectodomain construct indicates binding of the test peptide to a 5 helix bundle or a fusion bundle intermediate of EBOV GP2. In some instances, the control peptide is an unstapled version of the test peptide. For example, the control peptide may have the amino acid sequence of the test peptide except that the control peptide contains the corresponding wild type amino acids at the positions of the staple(s) or stitch(es) in the test peptide.

Methods of determining whether a peptide (e.g., a structurally stabilized peptide described herein) prevents or blocks fusion of an Ebola virus membrane and a host membrane are known in the art, such as, e.g., cytotoxicity and immunofluorescence. In some instances, a peptide prevents or blocks fusion of an Ebola virus membrane and a host membrane if less than 1%, less than 5%, less than 10%, less than 15% less than 20%, less than 30%, less than 40%, or less than 50% of cells are infected with Ebola virus at a multiplicity of infection of 0.1, 0.5, 1, or 10 in the presence the peptide. In some instances, a peptide prevents or blocks fusion of an Ebola virus membrane and a host membrane if less than 1%, less than 5%, less than 10%, less than 15% less than 20%, less than 30%, less than 40%, or less than 50% of cells exhibit fusion of the Ebola virus membrane and the host membrane after infection with Ebola virus at a multiplicity of infection of 0.1, 0.5, 1, or 10 in the presence the peptide.

Structurally Stabilized EBOV GP2 CHR Peptides and Variants

This disclosure also features stabilized versions (e.g., internally cross-linked, e.g., stapled or stitched) of the above-described EBOV GP2 CHR peptides.

A peptide helix is an important mediator of key protein-protein interactions that regulate many important biological processes such as apoptosis; however, when such a helix is taken out of its context within a protein and prepared in isolation, it usually adopts a random coil conformation, leading to a drastic reduction in biological activity and thus diminished therapeutic potential. The present disclosure provides structurally stabilized EBOV GP2 CHR peptides. The present disclosure includes structurally stabilized EBOV GP2 CHR peptides (such as structurally stabilized versions of the EBOV GP2 CHR peptides described above) comprising at least two modified amino acids joined by an internal (intramolecular) cross-link (a staple or stitch). Stabilized peptides as described herein include stapled peptides and stitched peptides as well as peptides containing multiple stitches, multiple staples or a mix of staples and stitches, or other chemical strategies for structural reinforcement (see. e.g., Balaram P. Cur. Opin. Struct. Biol. 1992; 2:845; Kemp D S, et al., *J. Am. Chem. Soc.* 1996; 118:4240; Omer B P, et al., *J Am. Chem. Soc.* 2001; 123:5382; Chin J W, et al., *Int. Ed.* 2001; 40:3806; Chapman R N, et al., *J Am. Chem. Soc.* 2004; 126:12252; Home W S, et al., *Chem., Int. Ed.* 2008; 47:2853; Madden et al., *Chem Commun* (Camb). 2009 Oct. 7; (37): 5588-5590; Lau et al., *Chem. Soc. Rev.,* 2015, 44:91-102; and Gunnoo et al., *Org. Biomol. Chem.,* 2016, 14:8002-8013; all of which are incorporated by reference herein in its entirety).

In certain instances, one or more of the EBOV GP2 CHR peptides described herein can be structurally stabilized by peptide stapling (see, e.g., Walensky, *J. Med. Chem.,* 57:6275-6288 (2014), the contents of which are incorporated by reference herein in its entirety). A peptide is "structurally stabilized" in that it maintains its native secondary structure. For example, stapling allows a peptide, predisposed to have an α-helical secondary structure, to maintain its native α-helical conformation. This secondary structure increases resistance of the peptide to proteolytic cleavage and heat, and also may increase target binding affinity, hydrophobicity, and cell permeability (e.g., the ability to be taken up by endosomes). Accordingly, the stapled (cross-linked) peptides described herein have improved biological activity relative to a corresponding non-stapled (un-cross-linked) peptide.

"Peptide stapling" is a term coined from a synthetic methodology wherein two olefin-containing side-chains (e.g., cross-linkable side chains) present in a peptide chain are covalently joined (e.g., "stapled together") using a ring-closing metathesis (RCM) reaction to form a cross-linked ring (see, e.g., Blackwell et al., *J Org. Chem.,* 66: 5291-5302, 2001; Angew et al., *Chem. Int. Ed.* 37:3281, 1994). As used herein, the term "peptide stapling" includes the joining of two (e.g., at least one pair of) double bond-containing side-chains, triple bond-containing side-chains, or double bond-containing and triple bond-containing side chain, which may be present in a peptide chain, using any number of reaction conditions and/or catalysts to facilitate such a reaction, to provide a singly "stapled" peptide. The term "multiply stapled" peptides refers to those peptides containing more than one individual staple, and may contain two, three, or more independent staples of various spacing. Additionally, the term "peptide stitching," as used herein, refers to multiple and tandem "stapling" events in a single peptide chain to provide a "stitched" (e.g., tandem or multiply stapled) peptide, in which two staples, for example, are linked to a common residue. Peptide stitching is disclosed, e.g., in WO 2008/121767 and WO 2010/068684, which are both hereby incorporated by reference in their entirety. In some instances, staples, as used herein, can retain the unsaturated bond or can be reduced.

In certain instances, one or more of the EBOV GP2 CHR peptides described herein can be structurally stabilized. In some instances, the EBOV GP2 CHR peptides of this disclosure are structurally stabilized by a hydrocarbon staple or stitch, a lactam staple or stitch; a UV-cycloaddition staple or stitch; an oxime staple or stitch; a thioether staple or stitch; a double-click staple or stitch; a bis-lactam staple or stitch; a bis-arylation staple or stitch; or a combination of any two or more thereof. In some instances, the EBOV GP2 CHR peptides of this disclosure are structurally stabilized by a hydrocarbon staple. In some instances, the EBOV GP2 CHR peptides of this disclosure are structurally stabilized by a hydrocarbon stitch.

In some instances, the structurally stabilized (e.g., stapled or stitched) peptide is a cross-linked version of a peptide comprising or consisting of any one of the amino acids sequences of SEQ ID NOs:2-6, as listed in Table 1. In some instances, the stapled peptide is a hydrocarbon stapled version of a peptide comprising or consisting of any one of the amino acids sequences of SEQ ID NOs:2-6, as listed in Table 1.

In some instances, the stapled peptide is a peptide comprising or consisting of any one of the amino acids sequences of SEQ ID NOs:2-6, except that at least two (e.g., 2, 3, 4) amino acids of SEQ ID NOs:2-6 are replaced with a non-natural amino acid capable of forming a staple or stitch (e.g., non-natural amino acids with olefinic side chains, e.g., (S)-2-(4'-pentenyl)Alanine, (R)-2-(7'-octenyl) Alanine). In some instances, the stapled peptide is a peptide comprising or consisting of any one of the amino acids sequences of SEQ ID NOs:2-6 or comprising 1 to 13 (i.e., 1, 2, 3, 4, 5, 6, 7, 8, 9, 10, 11, 12, or 13) amino acid substitutions, deletions and/or insertions therein. In certain instances, the stapled peptide includes at least two (e.g., 2, 3, 4, 5, 6) amino acid substitutions, wherein the substituted amino acids are separated by two, three, or six amino acids, and wherein the substituted amino acids are non-natural amino acids with olefinic side chains (e.g., (S)-2-(4'-pentenyl)Alanine or (R)-2-(7'-octenyl)Alanine). There are many known non-natural amino acids that may be used as stapling amino acids or stitching amino acids, any of which may be included in the peptides of the present invention. Some examples of non-natural amino acids that may be used as stapling amino acids or stitching amino acids are: (R)-2-(7'-octenyl)Alanine, (S)-2-(7'-octenyl)Alanine, (S)-2-(4'-pentenyl)Alanine, (R)-2-(4'-pentenyl)Alanine, 2,2-bis(4-pentenyl)glycine, 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with $—C(=O)C_6H_5$; $—CF_3$; —CN; -halo; $—NO_2$; $CH_3$), disubstituted phenylalanines, substituted tyrosines (e.g., further substituted with $—C=O)C_6H_5$; $—CF_3$; —CN; -halo; $—NO_2$; $CH_3$), and statine. Additionally, amino acids can be derivatized to include amino acid residues that are hydroxylated, phosphorylated, sulfonated, acylated, or glycosylated. In some instances, the amino acids forming the staple or stitch (also referred to as the "stapling amino acids" or the "stitching amino acids", respectively) are (S)-2-(4'-pentenyl)Alanine at each of positions i and i+4 of the staple. In some instances, the amino acids forming the staple or stitch are (R)-2-(4'-pentenyl)Alanine at each of positions i and i+4 of the staple. In some instances, the amino acids forming the staple or stitch are (R)-2-(7'-octenyl)Alanine and (S)-2-(4'-pentenyl)Alanine at positions i and i+7, respectively, of the staple. In some instances, the amino acids forming the staple or stitch are (S)-2-(4'-pentenyl)Alanine, 2,2-bis(4-pentenyl) glycine, and (S)-α-(7'-octenyl)alanine at positions i, i+4, and i+11, respectively, of the stitch. In some instances, the amino acids forming the staple or stitch are (R)-α-(4'-pentenyl) alanine, 2,2-bis(4-pentenyl)glycine, and (R)-α-(7'-octenyl) alanine at positions i, i+4, and i+11, respectively, of the stitch. In some instances, the amino acids forming the staple or stitch are (R)-2-(4'-pentenyl)Alanine, 2,2-bis(4-pentenyl) glycine, and (R)-2-(4'-pentenyl)alanine at positions i, i+3, and i+7, respectively, of the stitch. In some instances, the amino acids forming the staple or stitch are (S)-2-(4'-pentenyl)alanine, 2,2-bis(4-pentenyl)glycine, and (S)-2-(4'-pentenyl)alanine at positions i, i+3, and i+7, respectively, of the stitch. In some instances, the amino acids forming the staple or stitch are (R)-α-(propenyl)alanine, 2,2-bis(4-pentenyl)glycine, and (R)-2-(4'-pentenyl)alanine at positions i, i+3, and i+7, respectively, of the stitch. In some instances, the amino acids forming the staple or stitch are (R)-2-(4'-pentenyl)Alanine, 2,2-bis(4-pentenyl)glycine, and (S)-2-(4'-pentenyl)Alanine at positions i, i+4, and i+8, respectively, of the stitch.

Hydrocarbon stapled peptides include one or more tethers (linkages) between two non-natural amino acids, which tether significantly enhances the α-helical secondary structure of the peptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful hydrocarbon stapled forms of that peptide, as are cross-links between X2 and X5, or between X2 and X6, or between X2 and X9, etc. (i.e., forming an "[i, i+3] staple", an "[i, i+4] staple", or an "[i, i+7] staple", respectively). The use of multiple cross-links (e.g., 2, 3, 4, or more) is also contemplated. The use of multiple cross-links is very effective at stabilizing and optimizing the peptide, especially with increasing peptide length. Thus, the disclosure encompasses the incorporation of more than one cross-link within the peptide sequence to either further stabilize the sequence or facilitate the structural stabilization, proteolytic resistance, acid stability, thermal stability, cellular permeability, and/or biological activity enhancement of longer peptide stretches. Additional description regarding making and use of hydrocarbon stapled peptides can be found, e.g., in U.S. Patent Publication Nos. 2012/0172285, 2010/0286057, and 2005/0250680, the contents of all of which are incorporated by reference herein in their entireties.

In certain instances when a staple is at the i and i+3 residues, (R)-2-(2-propenyl)alanine and (S)-2-(4'-pentenyl) Alanine; or (R)-2-(4-pentenyl)alanine and (S)-2-(4'-pentenyl)Alanine are substituted for the amino acids at those positions. In certain instances when a staple is at the i and i+4 residues, (S)-2-(4'-pentenyl)Alanine is substituted for the amino acids at i and i+4. In certain instances when a staple is at the i and i+7 residues, (S)-2-(4'-pentenyl)Alanine and (R)-2-(7'-octenyl)Alanine are substituted for the amino acids at i and i+7. In some instances, when the peptide is stitched, the amino acids of the peptide to be involved in the "stitch" are substituted with: (i) 2,2-bis(4-pentenyl)glycine, (S)-2-(4'-pentenyl)Alanine, and (S)-2-(7'-octenyl)Alanine; or (ii) 2,2-bis(4-pentenyl)glycine, (R)-2-(4'-pentenyl)Alanine, and (R)-2-(7'-octenyl)Alanine; or (iii) 2,2-bis(4-pentenyl)glycine, (R)-2-(7'-octenyl)Alanine, and (R)-2-(7'-octenyl)Alanine; or (iv) 2,2-bis(4-pentenyl)glycine, (S)-2-(7'-octenyl)Alanine, and (S)-2-(7'-octenyl)Alanine; (v) 2,2-bis (4-pentenyl)glycine, (S)-2-(4'-pentenyl)Alanine, (R)-2-(4'-pentenyl)Alanine; or (vi) 2,2-bis(4-pentenyl)glycine, (S)-2-(4'-pentenyl)Alanine, (S)-2-(4'-pentenyl)Alanine; or (vii) 2,2-bis(4-pentenyl)glycine, (R)-2-(propenyl)Alanine, (R)-2-(4'-pentenyl)Alanine; and other such combinations (see, e.g., Bird et al., ACS Chemical Biology, 2020, 15:1340-1348; Bird et al., PNAS, 2010, 107(32):14093-14098; Hilinski et al., JACS, 2014, 136:12314-12322; Bird et al., Nature Structure & Molecular Biology, 2014, 21(12):1058-1067; Kim et al., Organic Letters, 2010, 12(13):3046-3049; Schafmeister et al., J. Am Chem. Soc., 2000, 122:5891-5892; Shim et al., 2013, Chem Biol Drug Des, 2013, 82:635-642; each of which is incorporated by reference herein in its entirety).

In a peptide to be stapled, amino acids that interfere with (e.g., inhibit or reduce the efficiency of) the stapling reaction should be substituted with amino acids that do not interfere with (e.g., do not inhibit or do not substantially reduce the efficiency of) the stapling reaction. For example, methionine (Met, M) may interfere with the stapling reaction; thus, in certain instances, the methionine(s) in a peptide to be stapled is replaced with, e.g., norleucine(s).

In some instances, the staple is located at the amino acid positions in a EBOV GP2 CHR peptide corresponding to positions 1 and 5 of SEQ ID NO:2. In some instances, the staple is located at the amino acid positions in a EBOV GP2 CHR peptide corresponding to positions 2 and 6 of SEQ ID NO:2. In some instances, the staple is located at the amino acid positions in a EBOV GP2 CHR peptide corresponding to positions 5 and 9 of SEQ ID NO:2. In some instances, the staple is located at the amino acid positions in a EBOV GP2 CHR peptide corresponding to positions 6 and 10 of SEQ ID NO:2. In some instances, the staple is located at the amino acid positions in a EBOV GP2 CHR peptide corresponding to positions 9 and 13 of SEQ ID NO:2. In some instances, the staple is located at the amino acid positions in a EBOV GP2 CHR peptide corresponding to positions 12 and 16 of SEQ ID NO:2. In some instances, the staple is located at the amino acid positions in a EBOV GP2 CHR peptide corresponding to positions 13 and 17 of SEQ ID NO:2. In some instances, the staple is located at the amino acid positions in a EBOV GP2 CHR peptide corresponding to positions 1 and 8 of SEQ ID NO:2. In some instances, the staple is located at the amino acid positions in a EBOV GP2 CHR peptide corresponding to positions 2 and 9 of SEQ ID NO:2. In some instances, the staple is located at the amino acid positions in a EBOV GP2 CHR peptide corresponding to positions 6 and 13 of SEQ ID NO:2. In some instances, the staple is located at the amino acid positions in a EBOV GP2 CHR peptide corresponding to positions 9 and 16 of SEQ ID NO:2. In some instances, the stitch is located at the amino acid positions in a EBOV GP2 CHR peptide corresponding to positions 5, 8, and 12 of SEQ ID NO:2.

In some instances in which the EBOV GP2 CHR peptide comprises or consists of the amino acid sequence of SEQ ID NO:4, the stitch is located at amino acid positions 1 and 5 of SEQ ID NO:4 (i.e., positions 1 and 5 of SEQ ID NO:2). In some instances in which the EBOV GP2 CHR peptide comprises or consists of the amino acid sequence of SEQ ID NO:5, the stitch is located at amino acid positions 1 and 5 of SEQ ID NO:5 (i.e., positions 1 and 5 of SEQ ID NO:2). In some instances in which the EBOV GP2 CHR peptide comprises or consists of the amino acid sequence of SEQ ID NO:4, the stitch is located at amino acid positions 2 and 6 of SEQ ID NO:4 (i.e., positions 2 and 6 of SEQ ID NO:2). In some instances in which the EBOV GP2 CHR peptide comprises or consists of the amino acid sequence of SEQ ID NO:4, the stitch is located at amino acid positions 5 and 9 of SEQ ID NO:4 (i.e., positions 5 and 9 of SEQ ID NO:2). In some instances in which the EBOV GP2 CHR peptide comprises or consists of the amino acid sequence of SEQ ID NO:5, the stitch is located at amino acid positions 5 and 9 of SEQ ID NO:5 (i.e., positions 5 and 9 of SEQ ID NO:2). In some instances in which the EBOV GP2 CHR peptide comprises or consists of the amino acid sequence of SEQ ID NO:4, the stitch is located at amino acid positions 6 and 10 of SEQ ID NO:4 (i.e., positions 6 and 10 of SEQ ID NO:2). In some instances in which the EBOV GP2 CHR peptide comprises or consists of the amino acid sequence of SEQ ID NO:6, the stitch is located at amino acid positions 6 and 10 of SEQ ID NO:6 (i.e., positions 6 and 10 of SEQ ID NO:2). In some instances in which the EBOV GP2 CHR peptide comprises or consists of the amino acid sequence of SEQ ID NO:3, the stitch is located at amino acid positions 2 and 9 of SEQ ID NO:3 (i.e., positions 2 and 9 of SEQ ID NO:2). In some instances in which the EBOV GP2 CHR peptide comprises or consists of the amino acid sequence of SEQ ID NO:4, the stitch is located at amino acid positions 2 and 9 of SEQ ID NO:4 (i.e., positions 2 and 9 of SEQ ID NO:2).

In some instances, the stabilized EBOV GP2 CHR peptide comprises a stapled or stitched form of a peptide described in Table 2 (i.e., the stapled or stitched peptide is the product of one or more ring-closing metathesis reaction(s) on a peptide of Table 2).

TABLE 2

Exemplary stapled or stitched EBOV GP2 CHR peptides.

| SEQ ID NO | DESCRIPTION | SEQUENCE |
|---|---|---|
| 7 | EBOV GP2 CHR [1, 5] | **X**$_1$DWT**X**$_2$NITDKIDQIIHDFVDK, wherein each of $X_1$ and $X_2$ is independently a stapling amino acid |
| 8 | EBOV GP2 CHR [1, 5] (D12N, D20N) | **X**$_1$DWT**X**$_2$NITDKI**N**QIIHDFV**N**K, wherein each of $X_1$ and $X_2$ is independently a stapling amino acid |
| 9 | EBOV GP2 CHR [1, 5] (D2N, D12N, D20N) | **X**$_1$**N**WT**X**$_2$NITDKI**N**QIIHDFV**N**K, wherein each of $X_1$ and $X_2$ is independently a stapling amino acid |
| 10 | EBOV GP2 CHR [2, 6] | H**X**$_1$WTK**X**$_2$ITDKIDQIIHDFVDK, wherein each of $X_1$ and $X_2$ is independently a stapling amino acid |
| 11 | EBOV GP2 CHR [2, 6] (D12N, D20N) | H**X**$_1$WTK**X**$_2$ITDKI**N**QIIHDFV**N**K, wherein each of $X_1$ and $X_2$ is independently a stapling amino acid |
| 12 | EBOV GP2 CHR [5, 9] (D2N, D12N, D20N) | H**N**WT**X**$_1$NIT**X**$_2$KI**N**QIIHDFV**N**K, wherein each of $X_1$ and $X_2$ is independently a stapling amino acid |
| 13 | EBOV GP2 CHR [5, 9] (D12N, D20N) | HDWT**X**$_1$NIT**X**$_2$KI**N**QIIHDFV**N**K, wherein each of X1 and X2 is independently a stapling amino acid |
| 14 | EBOV GP2 CHR [6, 10] (D12N, D20N) | HDWTK**X**$_1$ITD**X**$_2$I**N**QIIHDFV**N**K, wherein each of $X_1$ and $X_2$ is independently a stapling amino acid |
| 15 | EBOV GP2 CHR [6, 10] (D2N, D9N, D12N, D20N) | H**N**WTK**X**$_1$IT**N**X$_2$I**N**QIIHDFV**N**K, wherein each of $X_1$ and $X_2$ is independently a stapling amino acid |
| 16 | EBOV GP2 CHR [9, 13] | HDWTKNIT**X**$_1$KID**X**$_2$IIHDFVDK, wherein each of $X_1$ and $X_2$ is independently a stapling amino acid |
| 17 | EBOV GP2 CHR [12, 16] | HDWTKNITDKI**X**$_1$QII**X**$_2$DFVDK, wherein each of $X_1$ and $X_2$ is independently a stapling amino acid |
| 18 | EBOV GP2 CHR [13, 17] | HDWTKNITDKID**X**$_1$IIH**X**$_2$FVDK, wherein each of $X_1$ and $X_2$ is independently a stapling amino acid |
| 19 | EBOV GP2 CHR [1, 8] | **X**$_1$DWTKNI**X**$_2$DKIDQIIHDFVDK, wherein each of $X_1$ and $X_2$ is independently a stapling amino acid |
| 20 | EBOV GP2 CHR [2, 9] (D20N) | H**X**$_1$WTKNIT**X**$_2$KIDQIIHDFV**N**K, wherein each of $X_1$ and $X_2$ is independently a stapling amino acid |
| 21 | EBOV GP2 CHR [2, 9] (D12N, D20N) | H**X**$_1$WTKNIT**X**$_2$KI**N**QIIHDFV**N**K, wherein each of $X_1$ and $X_2$ is independently a stapling amino acid |
| 22 | EBOV GP2 CHR [6, 13] | HDWTK**X**$_1$ITDKID**X**$_2$IIHDFVDK, wherein each of $X_1$ and $X_2$ is independently a stapling amino acid |
| 23 | EBOV GP2 CHR [9, 16] | HDWTKNIT**X**$_1$KIDQII**X**$_2$DFVDK, wherein each of $X_1$ and $X_2$ is independently a stapling amino acid |
| 24 | EBOV GP2 CHR [5, 8, 12] | HDWT**X**$_1$NI**X**$_2$DKI**X**$_3$QIIHDFVDK, wherein each of $X_1$, $X_2$, and $X_3$ is independently a stitching amino acid |
| 25 | EBOV GP2 CHR [1, 5] | **X**$_1$DWT**X**$_2$NITDKIDQIIHDFVDK, wherein each of $X_1$ and $X_2$ is (S)-2-(4'-pentenyl)Alanine |
| 26 | EBOV GP2 CHR [1, 5] (D12N, D20N) | **X**$_1$DWT**X**$_2$NITDKI**N**QIIHDFV**N**K, wherein each of $X_1$ and $X_2$ is (S)-2-(4'-pentenyl)Alanine |
| 27 | EBOV GP2 CHR [1, 5] (D2N, D12N, D20N) | **X**$_1$**N**WT**X**$_2$NITDKI**N**QIIHDFV**N**K, wherein each of $X_1$ and $X_2$ is (S)-2-(4'-pentenyl)Alanine |

TABLE 2-continued

Exemplary stapled or stitched EBOV GP2 CHR peptides.

| SEQ ID NO | DESCRIPTION | SEQUENCE |
|---|---|---|
| 28 | EBOV GP2 CHR [2, 6] | H$X_1$WTK$X_2$ITDKIDQIIHDFVDK, wherein each of $X_1$ and $X_2$ is (S)-2-(4'-pentenyl)Alanine |
| 29 | EBOV GP2 CHR [2, 6] (D12N, D20N) | H$X_1$WTK$X_2$ITDKINQIIHDFVNK, wherein each of $X_1$ and $X_2$ is (S)-2-(4'-pentenyl)Alanine |
| 30 | EBOV GP2 CHR [5, 9] (D2N, D12N, D20N) | HNWT$X_1$NIT$X_2$KINQIIHDFVNK, wherein each of $X_1$ and $X_2$ is (S)-2-(4'-pentenyl)Alanine |
| 31 | EBOV GP2 CHR [5, 9] (D12N, D20N) | HDWT$X_1$NIT$X_2$KINQIIHDFVNK, wherein each of $X_1$ and $X_2$ is (S)-2-(4'-pentenyl)Alanine |
| 32 | EBOV GP2 CHR [6, 10] (D12N, D20N) | HDWTK$X_1$ITD$X_2$INQIIHDFVNK, wherein each of $X_1$ and $X_2$ is (S)-2-(4'-pentenyl)Alanine |
| 33 | EBOV GP2 CHR [6, 10] (D2N, D9N, D12N, D20N) | HNWTK$X_1$ITN$X_2$INQIIHDFVNK, wherein each of $X_1$ and $X_2$ is (S)-2-(4'-pentenyl)Alanine |
| 34 | EBOV GP2 CHR [9, 13] | HDWTKNIT$X_1$KID$X_2$IIHDFVDK, wherein each of $X_1$ and $X_2$ is (S)-2-(4'-pentenyl)Alanine |
| 35 | EBOV GP2 CHR [12, 16] | HDWTKNITDKI$X_1$QII$X_2$DFVDK, wherein each of $X_1$ and $X_2$ is (S)-2-(4'-pentenyl)Alanine |
| 36 | EBOV GP2 CHR [13, 17] | HDWTKNITDKID$X_1$IIH$X_2$FVDK, wherein each of $X_1$ and $X_2$ is (S)-2-(4'-pentenyl)Alanine |
| 37 | EBOV GP2 CHR [1, 8] | $X_1$DWTKNI$X_2$DKIDQIIHDFVDK, wherein $X_1$ is (R)-2-(7'-octenyl) alanine and $X_2$ is (S)-2-(4'-pentenyl)Alanine |
| 38 | EBOV GP2 CHR [2, 9] (D20N) | H$X_1$WTKNIT$X_2$KIDQIIHDFVNK, wherein $X_1$ is (R)-2-(7'-octenyl) alanine and $X_2$ is (S)-2-(4'-pentenyl)Alanine |
| 39 | EBOV GP2 CHR [2, 9] (D12N, D20N) | H$X_1$WTKNIT$X_2$KINQIIHDFVNK, wherein $X_1$ is (R)-2-(7'-octenyl) alanine and $X_2$ is (S)-2-(4'-pentenyl)Alanine |
| 40 | EBOV GP2 CHR [6, 13] | HDWTK$X_1$ITDKID$X_2$IIHDFVDK, wherein $X_1$ is (R)-2-(7'-octenyl) alanine and $X_2$ is (S)-2-(4'-pentenyl)Alanine |
| 41 | EBOV GP2 CHR [9, 16] | HDWTKNIT$X_1$KIDQII$X_2$DFVDK, wherein $X_1$ is (R)-2-(7'-octenyl) alanine and $X_2$ is (S)-2-(4'-pentenyl)Alanine |
| 42 | EBOV GP2 CHR [5, 8, 12] | HDWT$X_1$NI$X_2$DKI$X_3$QIIHDFVDK, wherein $X_1$ is (S)-2-(4'-pentenyl)Alanine, $X_2$ is 2,2-bis(4-pentenyl)glycine, and $X_3$ is (S)-2-(4'-pentenyl)Alanine |

This disclosure also encompasses peptides or stabilized peptides that are identical to those listed in Table 2 but which have 1, 2, 3, 4, or 5 of the aspartic residues therein replaced by asparagine. In some instances, D2, D12, D20, D2 and D12, D2 and D20, D12 and D20, and D2, D12, and D20 (the numbering corresponding to SEQ ID NO:2) are substituted by asparagine.

In some instances, the disclosure features structurally stabilized (e.g., stapled or stitched) peptides comprising or consisting of the amino acid sequence of any one of SEQ ID NOs:7-9 and 25-27 (or a modified version thereof), wherein the sidechains of the stapling amino acid at positions 1 and 5 of the amino acid sequence of any one of SEQ ID NOs:7-9 and 25-27 are cross-linked (stapled) to each other. In some instances, the disclosure features internally cross-linked (e.g., stapled or stitched) peptides comprising or consisting of the amino acid sequence of any one of SEQ ID NOs:10, 11, 28, and 29 (or a modified version thereof), wherein the sidechains of the stapling amino acid at positions 2 and 6 of the amino acid sequence of any one of SEQ ID NOs:10, 11, 28, and 29 are cross-linked (stapled) to each other. In some instances, the disclosure features internally cross-linked (e.g., stapled or stitched) peptides comprising or consisting of the amino acid sequence of any one of SEQ ID NOs:12, 13, 30, and 31 (or a modified version thereof), wherein the sidechains of the stapling amino acid at positions 5 and 9 of the amino acid sequence of any one of SEQ ID NOs:12, 13, 30, and 31 are cross-linked (stapled) to each other. In some instances, the disclosure features internally cross-linked (e.g., stapled or stitched) peptides comprising or consisting of the amino acid sequence of any one of SEQ ID NOs:14, 15, 32, and 33 (or a modified version thereof), wherein the sidechains of the stapling amino acid at positions 6 and 10 of the amino acid sequence of any one of SEQ ID NOs:14, 15, 32, and 33 are cross-linked (stapled) to each other. In some instances, the disclosure features internally cross-linked (e.g., stapled or stitched) peptides comprising or consisting of the amino acid sequence of SEQ ID NO:16 or 34 (or a modified version thereof), wherein the sidechains of the stapling amino acid at positions 9 and 13 of the amino acid sequence of SEQ ID NO:16 or 34 are cross-linked (stapled) to each other. In some instances, the disclosure features internally cross-linked (e.g., stapled or stitched) peptides comprising or consisting of the amino acid sequence of SEQ ID NO:17 or 35 (or a modified version thereof), wherein the sidechains of the stapling amino acid at positions 12 and 16 of the amino acid sequence of SEQ ID NO:17 or 35 are cross-linked (stapled) to each other. In some instances, the disclosure features internally cross-linked (e.g., stapled or stitched) peptides comprising or consisting of the amino acid sequence of SEQ ID NO:18 or 36 (or a modified version thereof), wherein the sidechains of the stapling amino acid at positions 13 and 17 of the amino acid sequence of SEQ ID NO:18 or 36 are cross-linked (stapled) to each other. In some instances, the disclosure features internally cross-linked (e.g., stapled or stitched) peptides comprising or consisting of the amino acid sequence of SEQ ID NO:19 or 37 (or a modified version thereof), wherein the sidechains of the stapling amino acid at positions 1 and 8 of the amino acid sequence of SEQ ID NO:19 or 37 are cross-linked (stapled) to each other. In some instances, the disclosure features internally cross-linked (e.g., stapled or stitched) peptides comprising or consisting of the amino acid sequence of any one of SEQ ID NOs:20, 21, 38, and 39 (or a modified version thereof), wherein the sidechains of the stapling amino acid at positions 2 or 9 of the amino acid sequence of any one of SEQ ID NOs:20, 21, 38, and 39 are cross-linked (stapled) to each other. In some instances, the disclosure features internally cross-linked (e.g., stapled or stitched) peptides comprising or consisting of the amino acid sequence of SEQ ID NO:22 or 40 (or a modified version thereof), wherein the sidechains of the stapling amino acid at positions 6 and 13 of the amino acid sequence of SEQ ID NO:22 or 40 are cross-linked (stapled) to each other. In some instances, the disclosure features internally cross-linked (e.g., stapled or stitched) peptides comprising or consisting of the amino acid sequence of SEQ ID NO:23 or 41 (or a modified version thereof), wherein the sidechains of the stapling amino acid at positions 9 and 16 of the amino acid sequence of SEQ ID NO:23 or 41 are cross-linked (stapled) to each other. In some instances, the disclosure feature an internally cross-linked (e.g., stitched) peptide comprising the amino acid sequence of SEQ ID NO:24 or 42 (or a modified version thereof), wherein the sidechains of the stapling amino acid at positions 5 and 8 of SEQ ID NO:24 or 42 are cross-linked ("stitched") to each other and the side chains of positions 8 and 12 of SEQ ID NO:24 or 42 are cross-linked to each other, thereby forming a stitch between positions 5, 8, and 12 of SEQ ID NO:24 or 42.

Figure 14:
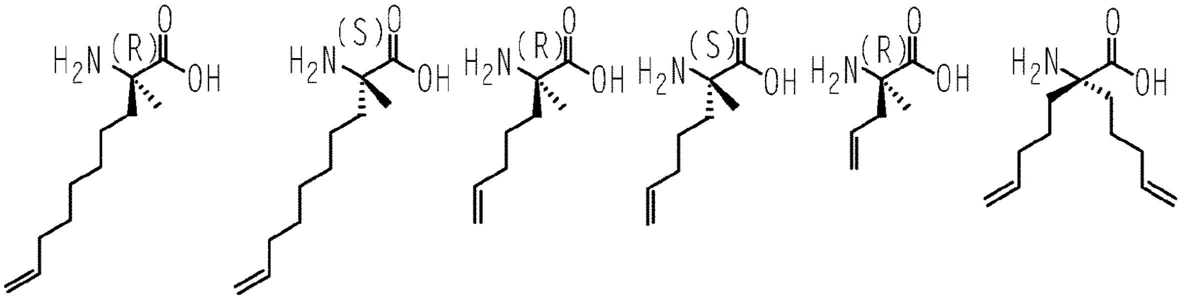
FIG. 14 shows the chemical structures of exemplary stapling/stitching amino acids used to generate various kinds of staples (top). The stapling/stitching amino acids from left to right are: (R)-2-(7-octenyl)alanine ($R_8$), (S)-2-(7-octenyl) alanine (S8), (R)-2-(4-pentenyl)alanine ($R_5$), (S)-2-(4-pentenyl)alanine (S5), (R)-2-(2-propenyl)alanine ($R_3$), and 2,2-bis(4-pentenyl)glycine (top panel). The middle panel illustrates peptides with staples of various lengths. The bottom panel illustrates a staple walk along a peptide sequence.
Figure 14:
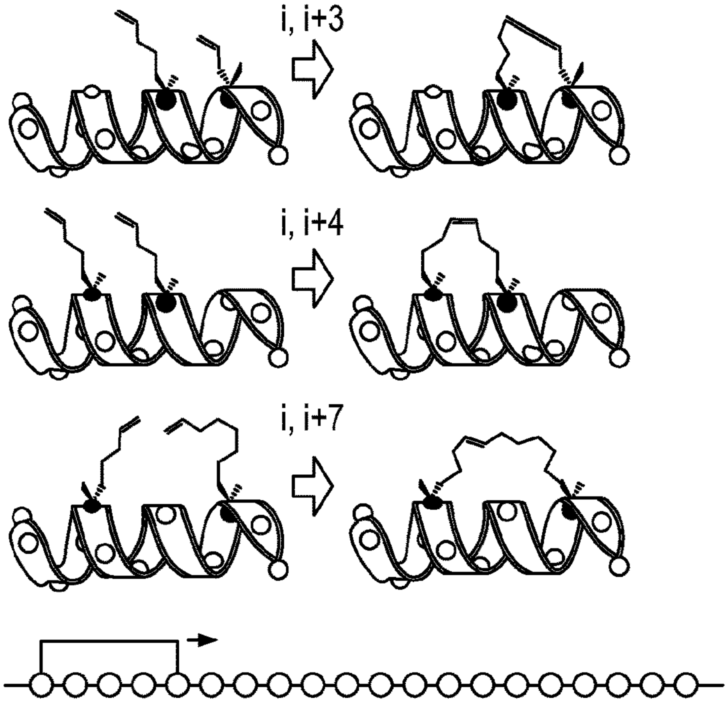
Figure 15:
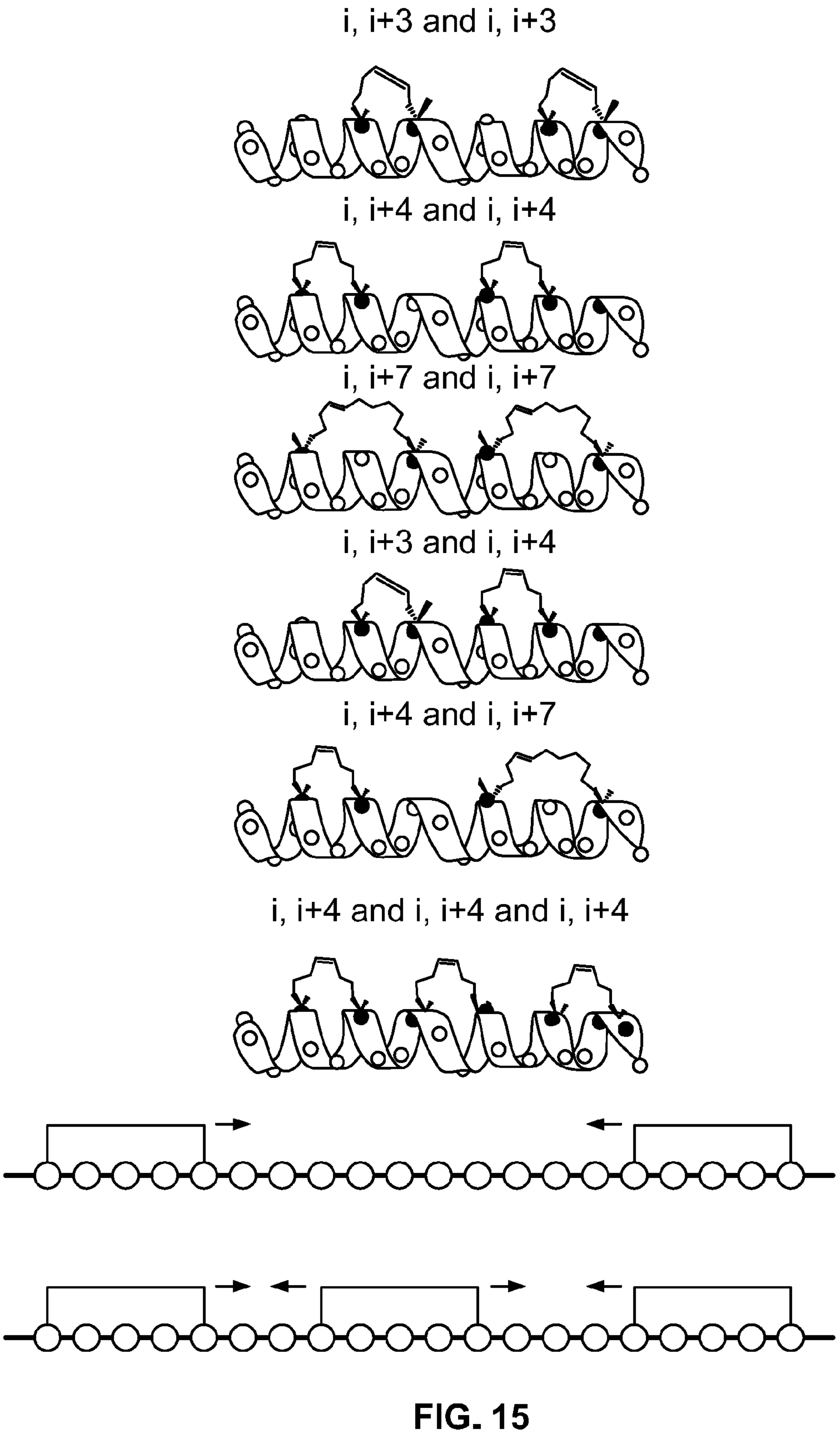
FIG. 15 is a schematic showing representations of various kinds of double and triple stapling strategies along with exemplary staple walks.
Figure 16:
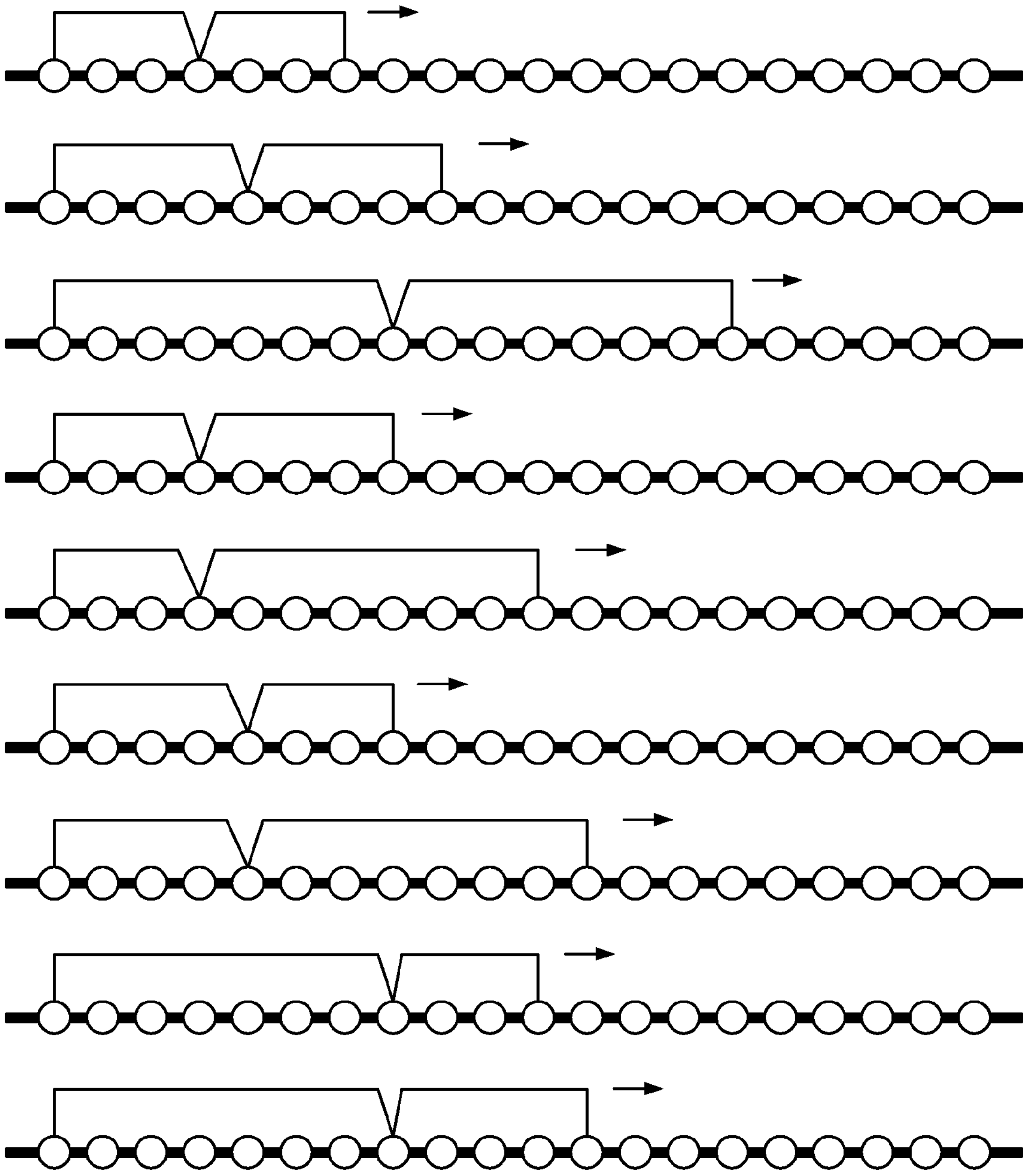
FIG. 16 is a schematic showing exemplary staple walks using various lengths of branched double staple or "stitched" moieties.
Figure 17:
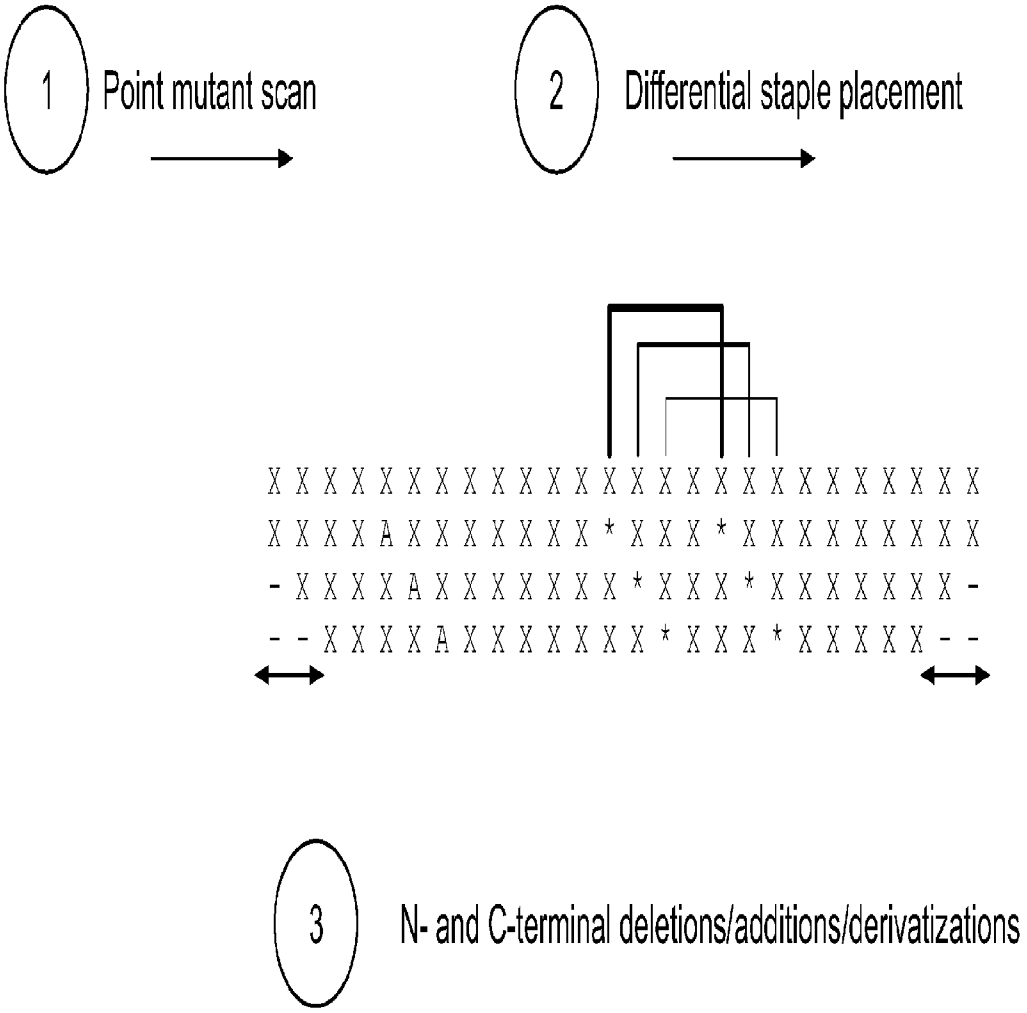
FIG. 17 is a schematic showing exemplary chemical alterations that are employed to generate stapled peptide derivatives.

FIG. 14 top panel shows exemplary chemical structures of non-natural amino acids that can be used to generate various cross-linked compounds (i.e., "stapling amino acids" or "stitching amino acids"). FIG. 14 middle panel illustrates peptides with hydrocarbon cross-links between positions i and i+3; i and i+4; and i and i+7 residues. FIG. 14 bottom panel illustrates a staple walk along a peptide sequence. FIG. 15 shows various peptide sequences with double and triple stapling strategies, and exemplary staple walks. FIG. 16 illustrates exemplary staple walks using various lengths of branched stitched moieties. FIG. 17 illustrates peptide variants based on point mutant and staple scans, and N- and C-terminal deletions, additions, and/or derivatizations.

In one aspect, the structurally stabilized EBOV GP2 CHR peptide comprises Formula (I), Formula (I)

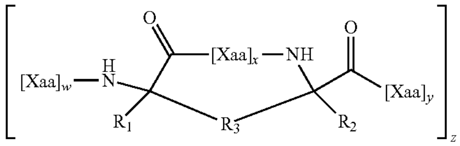

or a pharmaceutically acceptable salt thereof, wherein:

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]n$; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

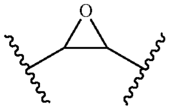;

$R_6$ is H, alkyl, or a therapeutic agent;

n is an integer from 1-4;

x is an integer from 2-10;

each y is independently an integer from 0-100;

z is an integer from 1-10 (e.g., 1, 2, 3, 4, 5, 6, 7, 8, 9, 10);

and each Xaa is independently an amino acid; and wherein the structurally stabilized peptide binds to a polypeptide comprising the amino acid sequence set forth in SEQ ID NO:1. In some instances, each of the $[Xaa]w$ of Formula (I), the $[Xaa]_x$ of Formula (I), and the $[Xaa]_y$ of Formula (I) is as described for any one of constructs 1-17 of Table 3. For example, for a stabilized peptide comprising the $[Xaa]_w$, the $[Xaa]_x$, and the $[Xaa]_y$ of construct 9 of Table 3, the $[Xaa]_w$, the $[Xaa]_x$, and the $[Xaa]_y$ is: HNWTK (SEQ ID NO:52), ITN, and INQIIHDFVNK (SEQ ID NO:51), respectively. As another example, for a stabilized peptide comprising the $[Xaa]_w$, the $[Xaa]_x$, and the $[Xaa]_y$ of construct 8 of Table 3, the $[Xaa]_w$, the $[Xaa]_x$, and the $[Xaa]_y$ is: HDWTK (SEQ ID NO:50), ITD, and INQIIHDFVNK (SEQ ID NO:51), respectively.

TABLE 3

$[Xaa]_w$, $[Xaa]_x$, and $[Xaa]_y$ sequences for Formula (I) constructs 1-17.

| Construct | $[Xaa]_w$ | $[Xaa]_x$ | $[Xaa]_y$ |
|---|---|---|---|
| 1 | [Absent] | DWT | NITDKIDQIIHDFVDK (SEQ ID NO: 43) |
| 2 | [Absent] | DWT | NITDKINQIIHDFVNK (SEQ ID NO: 44) |

TABLE 3-continued

[Xaa]$_w$, [Xaa]$_x$, and [Xaa]$_y$ sequences for Formula (I) constructs 1-17.

| Construct | [Xaa]$_w$ | [Xaa]$_x$ | [Xaa]$_y$ |
|---|---|---|---|
| 3 | [Absent] | NWT | NITDKINQIIHDFVNK (SEQ ID NO: 44) |
| 4 | H | WTK | ITDKIDQIIHDFVDK (SEQ ID NO: 45) |
| 5 | H | WTK | ITDKINQIIHDFVNK (SEQ ID NO: 46) |
| 6 | HNWT (SEQ ID NO: 47) | NIT | KINQIIHDFVNK (SEQ ID NO: 48) |
| 7 | HDWT (SEQ ID NO: 49) | NIT | KINQIIHDFVNK (SEQ ID NO: 48) |
| 8 | HDWTK (SEQ ID NO: 50) | ITD | INQIIHDFVNK (SEQ ID NO: 51) |
| 9 | HNWTK (SEQ ID NO: 52) | ITN | INQIIHDFVNK (SEQ ID NO: 51) |
| 10 | HDWTKNIT (SEQ ID NO: 53) | KID | IIHDFVDK (SEQ ID NO: 54) |
| 11 | HDWTKNITDKI (SEQ ID NO: 55) | QII | DFVDK (SEQ ID NO: 56) |
| 12 | HDWTKNITDKID (SEQ ID NO: 57) | IIH | FVDK (SEQ ID NO: 58) |
| 13 | [Absent] | DWTKNI (SEQ ID NO: 59) | DKIDQIIHDFVDK (SEQ ID NO: 60) |
| 14 | H | WTKNIT (SEQ ID NO: 61) | KIDQIIHDFVNK (SEQ ID NO: 62) |
| 15 | H | WTKNIT (SEQ ID NO: 61) | KINQIIHDFVNK (SEQ ID NO: 48) |
| 16 | HDWTK (SEQ ID NO: 63) | ITDKID (SEQ ID NO: 64) | IIHDFVDK (SEQ ID NO: 65) |
| 17 | HDWTKNIT (SEQ ID NO: 53) | KIDQII (SEQ ID NO: 66) | DFVDK (SEQ ID NO: 56) |

In certain instances, the sequences set forth above in Table 3 can have at least one (e.g., 1, 2, 3, 4, 5, 6) amino acid substitution or deletion. The EBOV GP2 CHR peptides can include any amino acid sequence described herein.

The tether of Formula (I) can include an alkyl, alkenyl, or alkynyl moiety (e.g., $C_5$, $C_8$, $C_{11}$, or $C_{12}$ alkyl, a $C_5$, $C_8$, or $C_{11}$ alkenyl, or $C_5$, $C_8$, $C_{11}$, or $C_{12}$ alkynyl). The tethered amino acid can be alpha disubstituted (e.g., $C_1$-$C_3$ or methyl).

In some instances of Formula (I), x is 2, 3, or 6. In some instances of Formula (I), each y is independently an integer between 0 and 15, or 3 and 15. In some instances of Formula (I), $R_1$ and $R_2$ are each independently H or $C_1$-$C_6$ alkyl. In some instances of Formula (I), $R_1$ and $R_2$ are each independently $C_1$-$C_3$ alkyl. In some instances or Formula (I), at least one of $R_1$ and $R_2$ are methyl. For example, $R_1$ and $R_2$ can both be methyl. In some instances of Formula (I), $R_3$ is alkyl (e.g., $C_8$ alkyl) and x is 3. In some instances of Formula (I), $R_3$ is $C_{11}$ alkyl and x is 6. In some instances of Formula (I), $R_3$ is alkenyl (e.g., $C_8$ alkenyl) and x is 3. In some instances of Formula (I), x is 6 and $R_3$ is $C_{11}$ alkenyl. In some instances, $R_3$ is a straight chain alkyl, alkenyl, or alkynyl. In some instances, $R_3$ is $-CH_2-CH_2-CH_2-CH{=}CH-CH_2-CH_2-CH_2-$.

In one aspect, a structurally stabilized EBOV GP2 CHR peptide comprises Formula (I), or a pharmaceutically acceptable salt thereof, wherein:

each $R_1$ and $R_2$ is H or a $C_1$ to $C_{10}$ alkyl, alkenyl, alkynyl, arylalkyl, cycloalkylalkyl, heteroarylalkyl, or heterocyclylalkyl, any of which is substituted or unsubstituted;

each $R_3$ is independently alkylene, alkenylene, or alkynylene, any of which is substituted or unsubstituted;

z is 1, 2, 3, 4, 5, 6, 7, 8, 9, or 10; and (a) each [Xaa]$_w$ is HDWTK (SEQ ID NO:50), each [Xaa]$_x$ is ITD, and each [Xaa]$_y$ is INQIIHDFVNK (SEQ ID NO:51);

(b) each [Xaa]$_w$ is HDWT (SEQ ID NO:49), each [Xaa]$_x$ is NIT, and each [Xaa]$_y$ is KINQIIHDFVNK (SEQ ID NO:48);

(c) each [Xaa]$_w$ is absent, each [Xaa]$_x$ is DWT, and each [Xaa]$_y$ is NITDKIDQIIHDFVDK (SEQ ID NO:43);

(d) each [Xaa]$_w$ is absent, each [Xaa]$_x$ is DWT, and each [Xaa]$_y$ is NITDKINQIIHDFVNK (SEQ ID NO:44);

(e) each [Xaa]$_w$ is absent, each [Xaa]$_x$ is NWT, and each [Xaa]$_y$ is NITDKINQIIHDFVNK (SEQ ID NO:44);

(f) each [Xaa]$_w$ is H, each [Xaa]$_x$ is WTK, and each [Xaa]$_y$ is ITDKIDQIIHDFVDK (SEQ ID NO:45);

(g) each [Xaa]$_w$ is H, each [Xaa]$_x$ is WTK, and each [Xaa]$_y$ is ITDKINQIIHDFVNK (SEQ ID NO:46);

(h) each [Xaa]$_w$ is HNWT (SEQ ID NO:47), each [Xaa]$_x$ is NIT, and each [Xaa]$_y$ is KINQIIHDFVNK (SEQ ID NO:48);

(i) each [Xaa]$_w$ is HNWTK (SEQ ID NO:52), each [Xaa]$_x$ is ITN, and each [Xaa]$_y$ is INQIIHDFVNK (SEQ ID NO:51);

(j) each [Xaa]$_w$ is HDWTKNIT (SEQ ID NO:53), each [Xaa]$_x$ is KID, and each [Xaa]$_y$ is IIHDFVDK (SEQ ID NO: 54);

(k) each [Xaa]$_w$ is HDWTKNITDKI (SEQ ID NO:55), each [Xaa]$_x$ is QII, and each [Xaa]$_y$ is DFVDK (SEQ ID NO:56);

(l) each [Xaa]$_w$ is HDWTKNITDKID (SEQ ID NO:57), each [Xaa]$_x$ is IIH, and each [Xaa]$_y$ is FVDK (SEQ ID NO:58);

(m) each [Xaa]$_w$ is absent, each [Xaa]$_x$ is DWTKNI (SEQ ID NO:59), and each [Xaa]$_y$ is DKIDQIIHDFVDK (SEQ ID NO:60);

(n) each [Xaa]$_w$ is H, each [Xaa]$_x$ is WTKNIT (SEQ ID NO:61), and each [Xaa]$_y$ is KIDQIIHDFVNK (SEQ ID NO:62);

(o) each [Xaa]$_w$ is H, each [Xaa]$_x$ is WTKNIT (SEQ ID NO:61), and each [Xaa]$_y$ is KINQIIHDFVNK (SEQ ID NO:48);

(p) each [Xaa]$_w$ is HDWTK (SEQ ID NO:63), each [Xaa]$_x$ is ITDKID (SEQ ID NO:64), and each [Xaa]$_y$ is IIHDFVDK (SEQ ID NO:65); or (q) each [Xaa]$_w$ is HDWTKNIT (SEQ ID NO:53), each [Xaa]$_x$ is KIDQII (SEQ ID NO:66), and each [Xaa]$_y$ is DFVDK (SEQ ID NO:56);

wherein the structurally stabilized EBOV GP2 CHR peptide binds to a polypeptide comprising the amino acid sequence set forth in SEQ ID NO: 1. In some instances, wherein $R_1$ is an alkyl. In some instances, $R_1$ is a methyl group. In some instances, $R_2$ is an alkyl. In some instances, $R_2$ is a methyl group. In some instances, $R_3$ is an alkenyl. In some instances, $R_3$ is 4-octenyl. In some instances, $R_1$ is a methyl group, $R_3$ is 4-octenyl, and $R_2$ is a methyl group. In some instances, z is 1.

In another aspect of Formula (I), the two alpha, alpha disubstituted stereocenters are both in the R configuration or S configuration (e.g., i, i+4 cross-link), or one stereocenter is R and the other is S (e.g., i, i+7 cross-link). Thus, where Formula (I) is depicted as:

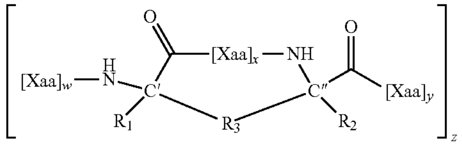

the C' and C" disubstituted stereocenters can both be in the R configuration or they can both be in the S configuration, e.g., when x is 3. When x is 6 in Formula (I), the C' disubstituted stereocenter is in the R configuration and the C" disubstituted stereocenter is in the S configuration. The $R_3$ double bond of Formula (I) can be in the E or Z stereochemical configuration.

In some instances of Formula (I), $R_3$ is $[R_4—K—R_4]n$; and $R_4$ is a straight chain alkyl, alkenyl, or alkynyl.

In one aspect, a structurally stabilized EBOV GP2 CHR peptide comprises Formula (II):

Formula (II)

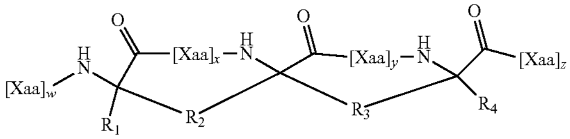

or a pharmaceutically acceptable salt thereof, wherein:

each $R_1$ and $R_4$ is independently H or a $C_{1-10}$ alkyl, alkenyl, alkynyl, arylalkyl, cycloalkylalkyl, heteroarylalkyl, or heterocyclylalkyl, any of which is substituted or unsubstituted;

each of $R_2$ and $R_3$ is independently a $C_{5-20}$ alkyl, alkenyl, alkynyl; $[R_4—K—R_4]n$; each of which is substituted with 0-6 $R_5$;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

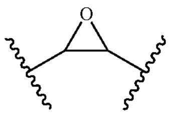

;

$R_6$ is H, alkyl, or a therapeutic agent;

n is an integer from 1-4;

(SEQ ID NO: 49)
$[Xaa]_w$ is HDWT;

$[Xaa]_x$ is NI;

$[Xaa]_y$ is DKI;
and (SEQ ID NO: 67)
$[Xaa]_z$ is QIIHDFVDK.

In some instances of Formula (II), $R_1$ and $R_4$ are each independently H or $C_1$-$C_6$ alkyl. In some instances of Formula (II), $R_1$ and $R_4$ are each independently $C_1$-$C_3$ alkyl. In some instances of Formula (II), at least one of $R_1$ and $R_4$ are methyl. For example, $R_1$ and $R_4$ can both be methyl. In some instances of Formula (II), $R_2$ and $R_3$ are each independently alkyl (e.g., $C_{12}$ alkyl). In some instances of Formula (II), $R_2$ and $R_3$ are each independently a $C_{12}$ alkyl. In some instances of Formula (II), $R_2$ and $R_3$ are each independently a straight chain alkyl, alkenyl, or alkynyl (e.g., a straight chain $C_{12}$ alkyl, alkenyl, or alkynyl. In some instances of Formula (II), $R_2$ is $—CH_2—CH_2—CH_2—CH_2—CH_2—CH_2—CH{=}CH—CH_2—CH_2—CH_2—CH_2—$. In some instances of Formula (II), $R_3$ is $—CH_2—CH_2—CH_2—CH_2—CH{=}CH—CH_2—CH_2—CH_2—CH_2—CH_2—CH_2—$.

In some instances, the structurally stabilized EBOV GP2 CHR peptide comprises Formula (II), or a pharmaceutically acceptable salt thereof, wherein:

(SEQ ID NO: 49)
$[Xaa]_w$ is HDWT;

$[Xaa]_x$ is NI;

$[Xaa]_y$ is DKI;
and (SEQ ID NO: 67)
$[Xaa]_z$ is QIIHDFVDK;

each $R_1$ and $R_4$ is independently H, alkyl, alkenyl, alkynyl, arylalkyl, cycloalkylalkyl, heteroarylalkyl, or heterocyclylalkyl, any of which is substituted or unsubstituted;

each $R_2$ and $R_3$ is independently alkylene, alkenylene, or alkynylene, any of which is substituted or unsubstituted; and wherein the structurally stabilized EBOV GP2 CHR peptide binds to a polypeptide comprising the amino acid sequence set forth in SEQ ID NO:1. In some instances, $R_1$ is an alkyl. In some instances, $R_1$ is a methyl group. In some instances, $R_4$ is an alkyl. In some instances, $R_4$ is a methyl group. In some instances, $R_2$ is an alkenyl. In some instances, $R_2$ is 4-octenyl. In some instances, $R_3$ is an alkenyl. In some instances, $R_3$ is 4-octenyl. In some instances, $R_1$ is a methyl group, $R_2$ is 4-octenyl, $R_3$ is 4-octenyl, and $R_4$ is a methyl group.

TABLE 4

| [Xaa]$_w$, [Xaa]$_x$, and [Xaa]$_y$ sequences for Formula (II) construct 18. | | | | |
|---|---|---|---|---|
| Construct | [Xaa]$_w$ | [Xaa]$_x$ | [Xaa]$_y$ | [Xaa]$_z$ |
| 18 | HDWT (SEQ ID NO: 49) | NI | DKI | QIIHDFVDK (SEQ ID NO: 67) |

In another aspect of Formula (II), of the three alpha, alpha disubstituted stereocenters: (i) two stereocenters are in the R configuration and one stereocenter is in the S configuration; or (ii) two stereocenters are in the S configuration and one stereocenter is in the R configuration. Thus, where Formula (II) is depicted as:

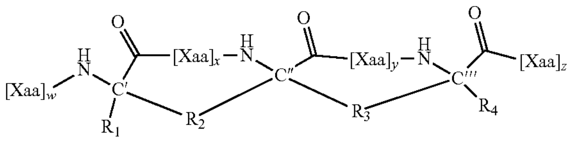

the C' and C''' disubstituted stereocenters can both be in the R configuration or they can both be in the S configuration. When both C' and C''' are in the R configuration, C'' is in the S configuration. When both C' and C''' are in the S configuration, C'' is in the R configuration. The double bond in each of $R_2$ and $R_3$ of Formula (II) can be in the E or Z stereochemical configuration.

In some instances of Formula (II), $R_3$ is $[R_4—K—R_4]n$; and $R_4$ is a straight chain alkyl, alkenyl, or alkynyl.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some instances, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some instances, the alkyl group is methyl, ethyl, or propyl. The term "alkylene" refers to a linking alkyl group.

As used herein, "alkenyl," employed alone or in combination with other terms, refers to an alkyl group having one or more carbon-carbon double bonds. In some instances, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to an alkyl group having one or more carbon-carbon triple bonds. Example alkynyl groups include, but are not limited to, ethynyl, propyn-1-yl, propyn-2-yl, and the like. In some instances, the alkynyl moiety contains 2 to 6 or 2 to 4 carbon atoms.

As used herein, "alkynyl," employed alone or in combination with other terms, refers to an alkyl group having one or more carbon-carbon triple bonds. Example alkynyl groups include, but are not limited to, ethynyl, propyn-1-yl, propyn-2-yl, and the like. In some instances, the alkynyl moiety contains 2 to 6 or 2 to 4 carbon atoms.

As used herein, the term "cycloalkylalkyl," employed alone or in combination with other terms, refers to a group of formula cycloalkyl-alkyl-. In some instances, the alkyl portion has 1 to 4, 1 to 3, 1 to 2, or 1 carbon atom(s). In some instances, the alkyl portion is methylene. In some instances, the cycloalkyl portion has 3 to 10 ring members or 3 to 7 ring members. In some instances, the cycloalkyl group is monocyclic or bicyclic. In some instances, the cycloalkyl portion is monocyclic. In some instances, the cycloalkyl portion is a $C_3$-7 monocyclic cycloalkyl group.

As used herein, the term "heteroarylalkyl," employed alone or in combination with other terms, refers to a group of formula heteroaryl-alkyl-. In some instances, the alkyl portion has 1 to 4, 1 to 3, 1 to 2, or 1 carbon atom(s). In some instances, the alkyl portion is methylene. In some instances, the heteroaryl portion is a monocyclic or bicyclic group having 1, 2, 3, or 4 heteroatoms independently selected from nitrogen, sulfur and oxygen. In some instances, the heteroaryl portion has 5 to 10 carbon atoms.

As used herein, the term "substituted" means that a hydrogen atom is replaced by a non-hydrogen group. It is to be understood that substitution at a given atom is limited by valency.

As used herein, "halo" or "halogen", employed alone or in combination with other terms, includes fluoro, chloro, bromo, and iodo. In some instances, halo is F or Cl.

In some instances, the disclosure features structurally stabilized (e.g., stapled or stitched) peptides comprising the amino acid sequence of any one of SEQ ID NOs:2-6 (or a modified version thereof), wherein: the side chains of two amino acids separated by two, three, or six amino acids are replaced by an internal staple, the side chains of three amino acids are replaced by an internal stitch, the side chains of four amino acids are replaced by two internal staples, or the side chains of five amino acids are replaced by the combination of an internal staple and an internal stitch. In some instances, the disclosure features structurally stabilized (e.g., stapled or stitched) peptides comprising the amino acid sequence of any one of SEQ ID NOs:2-6 (or a modified version thereof), wherein the side chains of two amino acids separated by two, three, or six amino acids are replaced by an internal staple. In some instances, the disclosure features structurally stabilized (e.g., stapled or stitched) peptides comprising the amino acid sequence of any one of SEQ ID NOs:2-6 (or a modified version thereof), wherein the side chains of two amino acids separated by three amino acids are replaced by an internal staple. In some instances, the disclosure features structurally stabilized (e.g., stapled or stitched) peptides comprising the amino acid sequence of any one of SEQ ID NOs:2-6 (or a modified version thereof), wherein the side chains of two amino acids separated by six amino acids are replaced by an internal staple. In some instances, the disclosure features structurally stabilized (e.g., stapled or stitched) peptides comprising the amino acid sequence of any one of SEQ ID NOs:2-6 (or a modified version thereof), wherein the side chains of three amino acids are replaced by an internal stitch. In certain instances, the amino acids corresponding to one or more of positions Trp3, Thr4, Ile7, Ile11, Ile14, Ile15, and Phe18 of SEQ ID NO:2 are not replaced with a staple or stitch. The stapled or stitched peptide can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In a specific instance, the stapled or stitched peptide is 5-21 amino acids (i.e., 5, 6, 7, 8, 9, 10, 11, 12, 13, 14, 15, 16, 17, 18, 19, 20, 21) in length. In a specific instance, the stapled or stitched peptide is 10-21 amino acids (i.e., 10, 11, 12, 13, 14, 15, 16, 17, 18, 19, 20, 21) amino acids in length. In a specific instance, the stapled or stitched peptide is 15-21 amino acids (i.e., 15, 16, 17, 18, 19, 20, 21) amino acids in length. In a specific instance, the stapled or stitched peptide is 21 amino acids in length. In a specific instance, the stapled or stitched peptide is 5-30 amino acids (i.e., 5, 6, 7, 8, 9, 10, 11, 12, 13, 14, 15, 16, 17, 18, 19, 20, 21, 22, 23, 24, 25, 26, 27, 28, 29, 30) in length. In a specific instance, the stapled or stitched peptide is 10-30 amino acids (i.e., 10, 11, 12, 13, 14, 15, 16, 17, 18, 19, 20, 21, 22, 23, 24, 25, 26, 27, 28, 29, 30) amino acids in length. In a specific instance, the stapled or stitched peptide is 15-30 amino acids (i.e., 15, 16, 17, 18, 19, 20, 21, 22, 23, 24, 25, 26, 27, 28, 29, 30) amino acids in length. In a specific instance, the stapled or stitched peptide is 13 amino acids in length. Exemplary EBOV GP2 CHR stapled or stitched peptides are shown in Table 2 and described in Formula (I) and Table 3. In one instance, the EBOV GP2 CHR stapled or stitched peptide comprises or consists of a stapled or stitched version of the amino acid sequence of any one of SEQ ID NOs: 7-42 (e.g., the product of a ring-closing metathesis reaction performed on a peptide comprising the amino acid sequence of any one of SEQ ID NOs:7-42, respectively). In one instance, the EBOV GP2 CHR stapled or stitched peptide comprises or consists of a stapled or stitched version of the amino acid sequence of SEQ ID NO: 15 (e.g., the product of a ring-closing metathesis reaction performed on a peptide comprising the amino acid sequence of SEQ ID NO:15). In one instance, the EBOV GP2 CHR stapled or stitched peptide comprises or consists of a stapled or stitched version of the amino acid sequence of SEQ ID NO: 14 (e.g., the product of a ring-closing metathesis reaction performed on a peptide comprising the amino acid sequence of SEQ ID NO:14).

EBOV GP2 CHR stapled and stitched peptides are shown in Tables 2 to Tables 4. In one instance, the EBOV GP2 CHR stapled peptide comprises or consists of the amino acid sequence of SEQ ID NO:7. In one instance, the EBOV GP2 CHR stapled peptide comprises or consists of the amino acid sequence of SEQ ID NO:25. In one instance, the EBOV GP2 CHR stapled peptide comprises or consists of the amino acid sequence of SEQ ID NO:8. In one instance, the EBOV GP2 CHR stapled peptide comprises or consists of the amino acid sequence of SEQ ID NO:26. In one instance, the EBOV GP2 CHR stapled peptide comprises or consists of the amino acid sequence of SEQ ID NO:9. In one instance, the EBOV GP2 CHR stapled peptide comprises or consists of the amino acid sequence of SEQ ID NO:27. In one instance, the EBOV GP2 CHR stapled peptide comprises or consists of the amino acid sequence of SEQ ID NO:10. In one instance, the EBOV GP2 CHR stapled peptide comprises or consists of the amino acid sequence of SEQ ID NO:28. In one instance, the EBOV GP2 CHR stapled peptide comprises or consists of the amino acid sequence of SEQ ID NO:11. In one instance, the EBOV GP2 CHR stapled peptide comprises or consists of the amino acid sequence of SEQ ID NO:29. In one instance, the EBOV GP2 CHR stapled peptide comprises or consists of the amino acid sequence of SEQ ID NO:12. In one instance, the EBOV GP2 CHR stapled peptide comprises or consists of the amino acid sequence of SEQ ID NO:30. In one instance, the EBOV GP2 CHR stapled peptide comprises or consists of the amino acid sequence of SEQ ID NO:13. In one instance, the EBOV GP2 CHR stapled peptide comprises or consists of the amino acid sequence of SEQ ID NO:31. In one instance, the EBOV GP2 CHR stapled peptide comprises the amino acid sequence of SEQ ID NO:14. In one instance, the EBOV GP2 CHR stapled peptide consists of the amino acid sequence of SEQ ID NO:14. In one instance, the EBOV GP2 CHR stapled peptide comprises the amino acid sequence of SEQ ID NO:32. In one instance, the EBOV GP2 CHR stapled peptide consists of the amino acid sequence of SEQ ID NO:32. In one instance, the EBOV GP2 CHR stapled peptide comprises the amino acid sequence of SEQ ID NO:15. In one instance, the EBOV GP2 CHR stapled peptide consists of the amino acid sequence of SEQ ID NO:15. In one instance, the EBOV GP2 CHR stapled peptide comprises the amino acid sequence of SEQ ID NO:33. In one instance, the EBOV GP2 CHR stapled peptide consists of the amino acid sequence of SEQ ID NO:33. In one instance, the EBOV GP2 CHR stapled peptide comprises or consists of the amino acid sequence of SEQ ID NO:16. In one instance, the EBOV GP2 CHR stapled peptide comprises or consists of the amino acid sequence of SEQ ID NO:34. In one instance, the EBOV GP2 CHR stapled peptide comprises or consists of the amino acid sequence of SEQ ID NO:17. In one instance, the EBOV GP2 CHR stapled peptide comprises or consists of the amino acid sequence of SEQ ID NO:35. In one instance, the EBOV GP2 CHR stapled peptide comprises or consists of the amino acid sequence of SEQ ID NO:18. In one instance, the EBOV GP2 CHR stapled peptide comprises or consists of the amino acid sequence of SEQ ID NO:36. In one instance, the EBOV GP2 CHR stapled peptide comprises or consists of the amino acid sequence of SEQ ID NO:19. In one instance, the EBOV GP2 CHR stapled peptide comprises or consists of the amino acid sequence of SEQ ID NO:37. In one instance, the EBOV GP2 CHR stapled peptide comprises or consists of the amino acid sequence of SEQ ID NO:20. In one instance, the EBOV GP2 CHR stapled peptide comprises or consists of the amino acid sequence of SEQ ID NO:38. In one instance, the EBOV GP2 CHR stapled peptide comprises or consists of the amino acid sequence of SEQ ID NO:21. In one instance, the EBOV GP2 CHR stapled peptide comprises or consists of the amino acid sequence of SEQ ID NO:39. In one instance, the EBOV GP2 CHR stapled peptide comprises or consists of the amino acid sequence of SEQ ID NO:22. In one instance, the EBOV GP2 CHR stapled peptide comprises or consists of the amino acid sequence of SEQ ID NO:40. In one instance, the EBOV GP2 CHR stapled peptide comprises or consists of the amino acid sequence of SEQ ID NO:23. In one instance, the EBOV GP2 CHR stapled peptide comprises or consists of the amino acid sequence of SEQ ID NO:41. In one instance, the EBOV GP2 CHR stitched peptide comprises or consists of the amino acid sequence of SEQ ID NO:24. In one instance, the EBOV GP2 CHR stitched peptide comprises or consists of the amino acid sequence of SEQ ID NO:42.

In certain instances, the stapled peptide comprises or consists of a variant of the amino acid sequence set forth in any one of SEQ ID NOs:2-6, wherein two amino acids each separated by 3 amino acids (i.e., positions i and i+4) are modified to structurally stabilize the peptide (e.g., by substituting them with non-natural amino acids to permit hydrocarbon stitching, i.e., stapling amino acids). In certain instances, the two amino acids each separated by three amino acids are at the amino acid positions in the EBOV GP2 CHR peptide corresponding to positions 1 and 5 of SEQ ID NO:2. In certain instances, the two amino acids each separated by three amino acids are at the amino acid positions in the EBOV GP2 CHR peptide corresponding to positions 2 and 6 of SEQ ID NO:2. In certain instances, the two amino acids each separated by three amino acids are at the amino acid positions in the EBOV GP2 CHR peptide corresponding to positions 5 and 9 of SEQ ID NO:2. In certain instances, the two amino acids each separated by three amino acids are at the amino acid positions in the EBOV GP2 CHR peptide corresponding to positions 6 and 10 of SEQ ID NO:2. In certain instances, the two amino acids each separated by three amino acids are at the amino acid positions in the EBOV GP2 CHR peptide corresponding to positions 9 and 13 of SEQ ID NO:2. In certain instances, the two amino acids each separated by three amino acids are at the amino acid positions in the EBOV GP2 CHR peptide corresponding to positions 12 and 16 of SEQ ID NO:2. In certain instances, the two amino acids each separated by three amino acids are at the amino acid positions in the EBOV GP2 CHR peptide corresponding to positions 13 and 17 of SEQ ID NO:2.

In certain instances, the stapled peptide comprises or consists of a variant of the amino acid sequence set forth in any one of SEQ ID NOs:2-6, wherein two amino acids each separated by 6 amino acids (i.e., positions i and i+7) are modified to structurally stabilize the peptide (e.g., by substituting them with non-natural amino acids to permit hydrocarbon stapling, i.e., with stapling amino acids). In certain instances, the two amino acids each separated by six amino acids are at the amino acid positions in the EBOV GP2 CHR peptide corresponding to positions 1 and 8 of SEQ ID NO:2. In certain instances, the two amino acids each separated by six amino acids are at the amino acid positions in the EBOV GP2 CHR peptide corresponding to positions 2 and 9 of SEQ ID NO:2. In certain instances, the two amino acids each separated by six amino acids are at the amino acid positions in the EBOV GP2 CHR peptide corresponding to positions 6 and 13 of SEQ ID NO:2. In certain instances, the two amino acids each separated by six amino acids are at the amino acid positions in the EBOV GP2 CHR peptide corresponding to positions 9 and 16 of SEQ ID NO:2.

In certain instances, the stitched peptide comprises or consists of a variant of the amino acid sequence set forth in any one of SEQ ID NOs:2-6, wherein three amino, at positions i, i+3, and i+7, are modified to structurally stabilize the peptide (e.g., by substituting them with non-natural amino acids to permit hydrocarbon stitching, i.e., with stitching amino acids). In certain instances, the three amino acids at positions i, i+3, and i+7 are at the amino acid positions in the EBOV GP2 CHR peptide corresponding to positions 5, 8, and 12 of SEQ ID NO:2.

While hydrocarbon tethers are common, other tethers can also be employed in the structurally stabilized EBOV GP2 CHR peptides described herein. For example, the tether can include one or more of an ether, thioether, ester, amine, or amide, or triazole moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid. Triazole-containing (e.g., 1, 4 triazole or 1, 5 triazole) crosslinks can be used (see, e.g., Kawamoto et al. 2012 *Journal of Medicinal Chemistry* 55:1137; WO 2010/060112). In addition, other methods of performing different types of stapling are well known in the art and can be employed with the EBOV GP2 CHR peptides described herein (see, e.g., Lactam stapling: Shepherd et al., *J Am. Chem. Soc.,* 127:2974-2983 (2005); UV-cycloaddition stapling: Madden et al., *Bioorg. Med. Chem. Lett.,* 21:1472-1475 (2011); Disulfide stapling: Jackson et al., *Am. Chem. Soc.,* 113:9391-9392 (1991); Oxime stapling: Haney et al., *Chem. Commun.,* 47:10915-10917 (2011); Thioether stapling: Brunel and Dawson, *Chem. Commun.,* 552-2554 (2005); Photoswitchable stapling: J. R. Kumita et al., *Proc. Natl. Acad. Sci. U.S.A.,* 97:3803-3808 (2000); Double-click stapling: Lau et al., *Chem. Sci.,* 5:1804-1809 (2014); Bis-lactam stapling: J. C. Phelan et al., *J. Am. Chem. Soc.,* 119:455-460 (1997); and Bis-arylation stapling: A. M. Spokoyny et al., *J. Am. Chem. Soc.,* 135:5946-5949 (2013)).

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while tethers spanning from amino acids i to i+3, i to i+4, and i to i+7 are common in order to provide a tether that is primarily on a single face of the alpha helix, the tethers can be synthesized to span any combinations of numbers of amino acids and also used in combination to install multiple tethers.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation, aminohydroxylation or dihydroxylation) to provide one of compounds below.

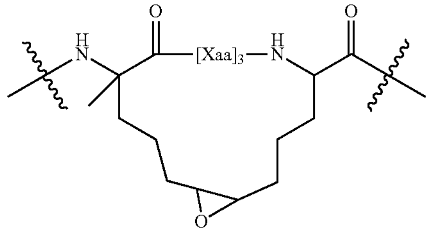

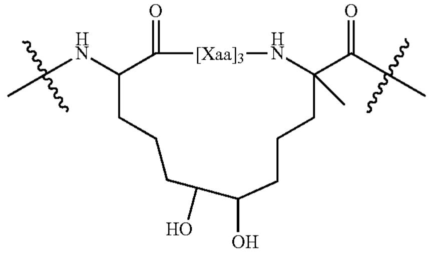

Either the epoxide moiety or one of the free hydroxyl moieties can be further functionalized. For example, the epoxide can be treated with a nucleophile, which provides additional functionality that can be used, for example, to attach a therapeutic agent. Such derivatization can alternatively be achieved by synthetic manipulation of the amino or carboxy-terminus of the peptide or via the amino acid side chain. Other agents can be attached to the functionalized tether, e.g., an agent that facilitates entry of the peptide into cells.

In some instances, alpha disubstituted amino acids are used in the peptide to improve the stability of the alpha helical secondary structure. However, alpha disubstituted amino acids are not required, and instances using mono-alpha substituents (e.g., in the tethered amino acids) are also envisioned.

The structurally stabilized (e.g., stapled or stitched) peptides can include a drug, a toxin, a derivative of polyethylene glycol; a second peptide; a carbohydrate, etc. Where a polymer or other agent is linked to the structurally stabilized (e.g., stapled or stitched) peptide, it can be desirable for the composition to be substantially homogeneous.

The addition of polyethelene glycol (PEG) molecules can improve the pharmacokinetic and pharmacodynamic properties of the peptide. For example, PEGylation can reduce renal clearance and can result in a more stable plasma concentration. PEG is a water soluble polymer and can be represented as linked to the peptide as formula:

$XO—(CH_2CH_2O)_n—CH_2CH_2—Y$ where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the peptide. Y may also be a maleimide linkage to a thiol group (including but not limited to, the thiol group of cysteine). Other methods for linking PEG to a peptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain instances, macromolecular polymer (e.g., PEG) is attached to a structurally stabilized (e.g., stapled or stitched) peptide described herein through an intermediate linker. In certain instances, the linker is made up of from 1 to 20 amino acids linked by peptide bonds, wherein the amino acids are selected from the 20 naturally occurring amino acids. Some of these amino acids may be glycosylated, as is well understood by those in the art. In other instances, the 1 to 20 amino acids are selected from glycine, alanine, proline, asparagine, glutamine, and lysine. In other instances, a linker is made up of a majority of amino acids that are sterically unhindered, such as glycine and alanine. Non-peptide linkers are also possible. For example, alkyl linkers such as $—NH(CH_2)_nC(O)—$, wherein n=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The structurally stabilized (e.g., stapled or stitched) peptides can also be modified, e.g., to further facilitate cellular uptake or increase in vivo stability, in some instances. For example, acylating or PEGylating a structurally stabilized peptide facilitates cellular uptake, increases bioavailability, increases blood circulation, alters pharmacokinetics, decreases immunogenicity and/or decreases the needed frequency of administration.

In some instances, the structurally stabilized (e.g., stapled or stitched) peptides disclosed herein have an enhanced ability to penetrate cell membranes (e.g., relative to non-stabilized peptides). See, e.g., International Publication No. WO 2017/147283, which is incorporated by reference herein in its entirety.

In some instances, the pharmaceutically acceptable salt is an acetate, a sulfate, or a chloride. Lists of other suitable salts are found in Remington's Pharmaceutical Sciences, 17th Ed., (Mack Publishing Company, Easton, 1985), p. 1418, Berge et al., J. Pharm. Sci., 1977, 66(1), 1-19 and in Stahl et al., Handbook of Pharmaceutical Salts: Properties, Selection, and Use, (Wiley, 2002).

In certain instances, each of the stabilized EBOV GP2 CHR peptides described above bind to a 5 helix bundle of EBOV GP2 or fusion bundle intermediate of EBOV GP2. In some instances, each of the stabilized EBOV GP2 CHR peptides described above bind to a 5 helix bundle of EBOV GP2 and prevents or blocks fusion of an Ebola virus membrane and a host membrane.

Properties of the stabilized (e.g., stapled or stitched) peptides of the invention can be assayed, for example, using the methods described below and in the Examples.

Assays to Determine α-Helicity:

Compounds are dissolved in an aqueous solution (e.g., 5 mM potassium phosphate solution at pH 7, or distilled $H_2O$, to concentrations of 25-50 μM). Circular dichroism (CD) spectra are obtained on a spectropolarimeter (e.g., Jasco J-710, Aviv) using standard measurement parameters (e.g., temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., Methods Enzymol. 130:208 (1986)).

Assays to Determine Melting Temperature (Tm):

Cross-linked or the unmodified template peptides are dissolved in distilled $H_2O$ or other buffer or solvent (e.g., at a final concentration of 50 μM) and Tm is determined by measuring the change in ellipticity over a temperature range (e.g., 4 to 95° C.) on a spectropolarimeter (e.g., Jasco J-710, Aviv) using standard parameters (e.g., wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays:

The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone and therefore may prevent or substantially retard proteolytic cleavage. The stabilized peptides of the present invention may be subjected to in vitro enzymatic proteolysis (e.g., trypsin, chymotrypsin, pepsin) to assess for any change in degradation rate compared to a corresponding unstabilized or alternatively stapled or stitched peptide. For example, the stabilized peptide and a corresponding unstabilized peptide are incubated with trypsin agarose and the reactions quenched at various time points by centrifugation and subsequent HPLC injection to quantitate the residual substrate by ultraviolet absorption at 280 nm. Briefly, the stabilized peptide and its precursor (5 mcg) are incubated with trypsin agarose (Pierce) (S/E ~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time.

Stabilized peptides and/or a corresponding unstabilized peptide can be each incubated with fresh mouse, rat and/or human serum (e.g., 1-2 mL) at 37° C. for, e.g., 0, 1, 2, 4, 8, and 24 hours. Samples of differing stabilized peptide concentration may be prepared by serial dilution with serum. To determine the level of intact compound, the following procedure may be used: The samples are extracted, for example, by transferring 100 μL of sera to 2 ml centrifuge tubes followed by the addition of 10 μL of 50% formic acid and 500 μL acetonitrile and centrifugation at 14,000 RPM for 10 min at 4+/−2° C. The supernatants are then transferred to fresh 2 ml tubes and evaporated on Turbovap under N2<10 psi, 37° C. The samples are reconstituted in 100 μL of 50:50 acetonitrile:water and submitted to LC-MS/MS analysis. Equivalent or similar procedures for testing ex vivo stability are known and may be used to determine stability of stabilized peptides in serum.

In Vivo Protease Resistance Assays:

A key benefit of peptide stapling or stitching is the translation of in vitro protease resistance into markedly improved pharmacokinetics in vivo.

In Vitro Binding Assays:

To assess the binding and affinity of stabilized peptides and their precursors to acceptor proteins, a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g., FITC-labeled peptides bound to a large protein) emit higher levels of polarized fluorescence due to their slower rates of rotation as compared to fluorescent tracers attached to smaller molecules (e.g., FITC-labeled peptides that are free in solution).

In some instances, structurally stabilized (e.g., stapled or stitched) peptides can be made by modifying (e.g., by amino acid substitution) a peptide of any one of SEQ ID NOs:2-6 or a modified version thereof. In some instances, an internal staple replaces the side chains of 2 amino acids, i.e., each staple is between two amino acids separated by, for example, 2, 3, or 6 amino acids. In some instances, an internal stitch replaces the side chains of 3 amino acids, i.e., the stitch is a pair of crosslinks between three amino acids separated by, for example, 2, 3, or 6 amino acids. In some instances, the internal stitch replaces the side chain of a first amino acid and a second and a third amino acid thereby cross-linking the first amino acid (which lies between the second and third amino acids) to the second and third amino acid via an internal cross-link, wherein the first and second amino acid are separated by two, three, or six amino acids, the first and the third amino acids are separated by three or six amino acids, and the second and third amino acids are distinct amino acids.

The structurally stabilized (e.g., stapled or stitched) peptide comprises at least two modified amino acids (relative to an EBOV GP2 CHR peptide) joined by an internal intramolecular cross-link (or "staple"), wherein the at least two amino acids are separated by 2, 3, or 6 amino acids. Structurally stabilized peptides herein include stapled peptides, including peptides having two staples and/or stitched peptides. The at least two modified amino acids can be non-natural alpha-amino acids (including, but not limited to α,α-disubstituted and N-alkylated amino acids). There are many known non-natural amino acids that may be used as stapling amino acids or stitching amino acids, any of which may be included in the peptides of the present invention. Some examples of non-natural amino acids that may be used as stapling amino acids or stitching amino acids are: (R)-2-(7'-octenyl)Alanine, (S)-2-(7'-octenyl)Alanine, (S)-2-(4'-pentenyl)Alanine, (R)-2-(4'-pentenyl)Alanine, bis-S5/R5, 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(═O)$C_6H_5$; —$CF_3$; —CN; -halo; —$NO_2$; $CH_3$), disubstituted phenylalanines, substituted tyrosines (e.g., further substituted with -Q=O) $C_6H_5$; —$CF_3$; —CN; -halo; —$NO_2$; $CH_3$), and statine. In some instances, the amino acids forming the staple or stitch (also referred to as the "stapling amino acids" or the "stitching amino acids" are (S)-2-(4'-pentenyl)Alanine at each of positions i and i+4. In some instances, the amino acids forming the staple or stitch are (R)-2-(4'-pentenyl)Alanine at each of positions i and i+4. In some instances, the amino acids forming the staple or stitch are (R)-2-(7'-octenyl) Alanine and (S)-2-(4'-pentenyl)Alanine at positions i and i+7, respectively. In some instances, the amino acids forming the staple or stitch are (S)-2-(4'-pentenyl)Alanine, 2,2-bis(4-pentenyl)glycine, and (S)-α-(7'-octenyl)alanine at positions i, i+4, and i+11, respectively, of the stitch. In some instances, the amino acids forming the staple or stitch are (R)-α-(4'-pentenyl)alanine, 2,2-bis(4-pentenyl)glycine, and (R)-α-(7'-octenyl)alanine at positions i, i+4, and i+11, respectively, of the stitch. In some instances, the amino acids forming the staple or stitch are (R)-2-(4'-pentenyl)Alanine, 2,2-bis(4-pentenyl)glycine, and (R)-2-(4'-pentenyl)alanine at positions i, i+3, and i+7, respectively, of the stitch. In some instances, the amino acids forming the staple or stitch are (S)-2-(4'-pentenyl)alanine, 2,2-bis(4-pentenyl)glycine, and (S)-2-(4'-pentenyl)alanine at positions i, i+3, and i+7, respectively, of the stitch. In some instances, the amino acids forming the staple or stitch are (R)-α-(propenyl)alanine, 2,2-bis(4-pentenyl)glycine, and (R)-2-(4'-pentenyl)alanine at positions i, i+3, and i+7, respectively, of the stitch. In some instances, the amino acids forming the staple or stitch are (R)-2-(4'-pentenyl)Alanine, 2,2-bis(4-pentenyl)glycine, and (S)-2-(4'-pentenyl)Alanine at positions i, i+4, and i+8, respectively, of the stitch. The skilled artisan will appreciate that other combinations for staples and stitches are permitted, such as, e.g., i, i+4 and i, i+4; i, i+4 and i, i+7; i, i+7 and i, i+4; and i, i+7 and i, i+7. See, e.g., Bird et al., ACS Chemical Biology, 2020, 15:1340-1348; Bird et al., PNAS, 2010, 107(32):14093-14098; Hilinski et al., JACS, 2014, 136:12314-12322; Bird et al., Nature Structure & Molecular Biology, 2014, 21(12):1058-1067; Kim et al., Organic Letters, 2010, 12(13):3046-3049; Schafmeister et al., J. Am Chem. Soc., 2000, 122:5891-5892; Shim et al., 2013, Chem Biol Drug Des, 2013, 82:635-642 (each of which is incorporated by reference herein in its entirety) for exemplary staples and stitches.

In some instances, structurally stabilized (e.g., stapled or stitched) EBOV GP2 CHR peptide variants of the disclosure are prepared from a peptide of any one of SEQ ID NOs:2-6 and having e.g., 1, 2, 3, 4, 5, 6, 7, 8, or 9 amino acid substitutions (e.g., 1, 2, 3, 4, 5, 6, 7, 8, or 9 amino acids are conservatively or non-conservatively substituted) and/or having, e.g., 1, 2, 3, 4, 5, 6, 7, 8, or 9 amino acid deletions from the N- and/or C-terminus (e.g., 1, 2, 3, 4, 5, 6, 7, 8, or 9 amino acids from the N- and/or C-terminus are deleted). Exemplary EBOV GP2 CHR peptides, including variants, are provided in Table 1 and in the amino acid sequence of SEQ ID NO:2. For example, in certain instances, the structurally stabilized EBOV GP2 CHR peptide variants of this disclosure can have 1, 2, 3, 4, 5, 6, 7, 8, 9, 10, 11, 12, or 13 amino acid substitutions in any one of SEQ ID NOs:2-6 (e.g., 1, 2, 3, 4, 5, 6, 7, 8, 9, 10, 11, 12, or 13 amino acids are conservatively or non-conservatively substituted). In some instances, one to three amino acids of any one of SEQ ID NOs:2-6 are substituted. The amino acid substitutions in any one of SEQ ID NOs:2-6 can be of non-NHR-interacting amino acids. Much greater variability is permitted in the non-NHR-interacting amino acids. In fact, just about every one of non-NHR-interacting amino acids can be substituted (e.g., conservative or non-conservative amino acid substitutions or substitution with alanine). In certain instances, one, two, or three NHR-interacting amino acids amino acids are substituted with another amino acid. In some instances, the substitution(s) is/are a conservative amino acid substitution. In other instances, the substitution(s) is/are a non-conservative amino acid substitution. In some instances, where there are more than one amino acid substitutions, the substitutions are both conservative and non-conservative amino acid substitutions. In some instances, where there are more than one amino acid substitutions, each of the substitutions are conservative amino acid substitutions. In some cases, where one to three amino acids (e.g., 1, 2, or 3) of any one of SEQ ID NOs:2-6 are substituted, the substitutions are all of non-NHR-interacting amino acids. In some cases, where one to three amino acids (e.g., 1, 2, or 3) of any one of SEQ ID NOs:2-6 are substituted, the substitutions are all of NHR-interacting amino acids. In some cases, where one to three amino acids (e.g., 1, 2, or 3) of any one of SEQ ID NOs:2-6 are substituted, the substitutions are of both non-NHR-interacting amino acids and NHR-interacting amino acids. In certain instances, the substituted amino acid(s) are selected from the group consisting of L-Ala, D-Ala, Aib, Sar, Ser, a substituted alanine, or a substituted glycine derivative.

In some instances, the structurally stabilized (e.g., stapled or stitched) EBOV GP2 CHR variant peptides comprise one or more (e.g., 1, 2, 3, 4, 5, 6, 7, 8, 9, 10, 11, or 12) amino acids corresponding to amino acids W615, T616, N618, I619, K622, 1623, Q625, I626, I627, D629, F630, and V631 (numbered according to SEQ ID NO:1), or conservative amino acid substitutions thereof.

In some instances, the structurally stabilized (e.g., stapled or stitched) EBOV GP2 CHR variant peptides comprise a conservative amino acid substitution at one or more (e.g., 1, 2, 3, 4, or 5) amino acids corresponding to amino acids K617, T620, D621, D624, and $H_{628}$ (numbered according to SEQ ID NO: 1). In some instances, the structurally stabilized (e.g., stapled or stitched) EBOV GP2 CHR variant peptides comprise a non-conservative amino acid substitution at one or more (e.g., 1, 2, 3, 4, or 5) amino acids corresponding to amino acids K617, T620, D621, D624, and $H_{628}$ (numbered according to SEQ ID NO:1).

In some instances, the structurally stabilized (e.g., stapled or stitched) EBOV GP2 CHR variant peptides do not comprise one or more (e.g., 1, 2, 3, or 4) of the amino acids corresponding to positions 615, 616, 630, and 631 of the amino acid sequence set forth in SEQ ID NO:1. For example, in some instances, the structurally stabilized (e.g., stapled or stitched) EBOV GP2 CHR variant peptides do not comprise the amino acids corresponding to positions 615, 616, 630, and 631 of the amino acid sequence set forth in SEQ ID NO:1. As another example, in some instances, the structurally stabilized (e.g., stapled or stitched) EBOV GP2 CHR variant peptides do not comprise the amino acids corresponding to positions 615 and 616 of the amino acid sequence set forth in SEQ ID NO:1. As another example, in some instances, the structurally stabilized (e.g., stapled or stitched) EBOV GP2 CHR variant peptides do not comprise the amino acids corresponding to positions 630 and 631 of the amino acid sequence set forth in SEQ ID NO:1.

In certain instances, the structurally stabilized (e.g., stapled or stitched) EBOV GP2 CHR variant peptides of this disclosure can have 1, 2, 3, 4, or 5, amino acids removed/deleted from the C-terminus of the sequence set forth in any one of SEQ ID NOs:2-6. In certain instances, the structurally stabilized (e.g., stapled or stitched) EBOV GP2 CHR variant peptides of this disclosure can have 1, 2, 3, 4, or 5, amino acid removed/deleted from the N-terminus of the sequence set forth in any one of SEQ ID NOs:2-6. In certain instances, these removed amino acids can be replaced with 1-6 (e.g., 1, 2, 3, 4, 5, or 6) amino acids selected from the group consisting of L-Ala, D-Ala, Aib, Sar, Ser, a substituted alanine, or a substituted glycine derivative.

The structurally stabilized (e.g., stapled or stitched) EBOV GP2 CHR peptide variants described herein can be optimized for therapeutic use. For example, if any of the above-described structurally stabilized (e.g., stapled or stitched) EBOV GP2 CHR peptide variants cause membrane disruption (cell lysis), the peptides can be optimized by lowering the overall peptide hydrophobicity. This can for example be achieved by substituting especially hydrophobic residues with an amino acid with lower hydrophobicity (e.g., alanine). Membrane disruption can also be lowered by reducing the overall positive charge of the peptide. This can be accomplished by substituting basic residues with uncharged or acidic residues. In certain instances, both the overall peptide hydrophobicity and the overall positive charge of the peptide are lowered. In some instances, the overall charge of the peptide is −2 to +2. In some instances, the overall charge of the peptide is −3 to +3. In some instances, the overall charge of the peptide is −1 to +3. In some instances, the overall charge of the peptide is 0 to +3. In some instances, the overall charge of the peptide is 0 to +2.

In certain instances, the structurally stabilized (e.g., stapled or stitched) EBOV GP2 CHR peptide variants described herein are from 5 to 50 (i.e., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50) amino acids in length, from 5 to 35 (i.e., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35) amino acids in length, from 5 to 30 (i.e., 5, 6, 7, 8, 9, 10, 11, 12, 13, 14, 15, 16, 17, 18, 19, 20, 21, 22, 23, 24, 25, 26, 27, 28, 29, 30) amino acids in length, from 5 to 25 (i.e., 5, 6, 7, 8, 9, 10, 11, 12, 13, 14, 15, 16, 17, 18, 19, 20, 21, 22, 23, 24, 25) amino acids in length, from 5 to 21 (i.e., 5, 6, 7, 8, 9, 10, 11, 12, 13, 14, 15, 16, 17, 18, 19, 20, 21) amino acids in length, from 10 to 21 (i.e., 10, 11, 12, 13, 14, 15, 16, 17, 18, 19, 20, 21) amino acids in length, from 15 to 21 (i.e., 15, 16, 17, 18, 19, 20, 21) amino acids in length, from 10 to 30 (i.e., 10, 11, 12, 13, 14, 15, 16, 17, 18, 19, 20, 21, 22, 23, 24, 25, 26, 27, 28, 29, 30) amino acids in length, or from 15 to 30 (i.e., 15, 16, 17, 18, 19, 20, 21, 22, 23, 24, 25, 26, 27, 28, 29, 30) amino acids in length. In certain instances, the structurally stabilized (e.g., stapled or stitched) EBOV GP2 CHR peptide variants described herein are 21 amino acids in length.

In certain instances, the structurally stabilized (e.g., stapled or stitched) EBOV GP2 CHR peptide variant comprises or consists of the amino acid sequence set forth in Table 2. In certain instances, the internally cross-linked (e.g., stapled or stitched) EBOV GP2 CHR peptide variant comprises or consists of any one of constructs 1-17 of Table 3 or construct 18 or Table 4.

Exemplary Structurally Stabilized EBOV GP2 CHR Peptide Variants

In a specific instance, the structurally stabilized (e.g., stapled or stitched) peptide is based on the amino acid sequence of SEQ ID NO:6. In a specific instance, the structurally stabilized (e.g., stapled or stitched) peptide comprises the amino acid sequence of SEQ ID NO:6 with: (i) two or more amino acid substitutions with stapling amino acids, and (ii) 0 to 6 (i.e., 0, 1, 2, 3, 4, 5, 6) additional amino acid substitutions, insertions, and/or deletions. In a specific instance, the structurally stabilized (e.g., stapled or stitched) peptide consists of the amino acid sequence of SEQ ID NO:6 with: (i) two or more amino acid substitutions with stapling amino acids, and (ii) 0 to 6 (i.e., 0, 1, 2, 3, 4, 5, 6) additional amino acid substitutions, insertions, and/or deletions. In certain instances, the structurally stabilized (e.g., stapled or stitched) peptide is based on the amino acid sequence of SEQ ID NO:6 with 0 to 3 amino acid deletions from the N-terminus. In certain instances, the stabilized peptide is based on the amino acid sequence of SEQ ID NO:6 with 0 to 3 amino acid deletions from the C-terminus. In a specific instance, the structurally stabilized (e.g., stapled or stitched) peptide is based on the amino acid sequence of HNWTKX$_1$ITNX$_2$INQIIHDFVNK, wherein each of $X_1$ and $X_2$ is independently a stapling amino acid (SEQ ID NO:15). In a specific instance, the structurally stabilized (e.g., stapled or stitched) peptide comprises the amino acid sequence of HNWTKX$_1$ITNX$_2$INQIIHDFVNK, wherein each of $X_1$ and $X_2$ is independently a stapling amino acid (SEQ ID NO:15), and has 0 to 6 (i.e., 0, 1, 2, 3, 4, 5, 6) amino acid substitutions, insertions, and/or deletions relative to SEQ ID NO:15 at position(s) other than $X_1$ and $X_2$. In a specific instance, the structurally stabilized (e.g., stapled or stitched) peptide consists of the amino acid sequence of HNWTKX$_1$ITNX$_2$INQIIHDFVNK, wherein each of $X_1$ and $X_2$ is independently a stapling amino acid (SEQ ID NO:15), and has 0 to 6 (i.e., 0, 1, 2, 3, 4, 5, 6) amino acid substitutions, insertions, and/or deletions relative to SEQ ID NO:15 at position(s) other than $X_1$ and $X_2$. In certain instances, the structurally stabilized (e.g., stapled or stitched) peptide is based on the amino acid sequence of SEQ ID NO:15 with 0 to 3 amino acid deletions from the N-terminus. In certain instances, the structurally stabilized (e.g., stapled or stitched) peptide is based on the amino acid sequence of SEQ ID NO:15 with 0 to 3 amino acid deletions from the C-terminus. In a specific instance, the structurally stabilized (e.g., stapled or stitched) peptide comprises the amino acid sequence of HNWTKX$_1$ITNX$_2$INQIIHDFVNK, wherein each of $X_1$ and $X_2$ is (S)-2-(4'-pentenyl)Alanine (SEQ ID NO:33), and has 0 to 6 (i.e., 0, 1, 2, 3, 4, 5, 6) amino acid substitutions, insertions, and/or deletions relative to SEQ ID NO:33 at position(s) other than $X_1$ and $X_2$. In a specific instance, the structurally stabilized (e.g., stapled or stitched) peptide consists of the amino acid sequence of HNWTKX$_1$ITNX$_2$INQIIHDFVNK, wherein each of $X_1$ and $X_2$ is (S)-2-(4'-pentenyl)Alanine (SEQ ID NO:33), and has 0 to 6 (i.e., 0, 1, 2, 3, 4, 5, 6) amino acid substitutions, insertions, and/or deletions relative to SEQ ID NO:33 at position(s) other than $X_1$ and $X_2$. In certain instances, the structurally stabilized (e.g., stapled or stitched) peptide is based on the amino acid sequence of SEQ ID NO:33 with 0 to 3 amino acid deletions from the N-terminus. In certain instances, the structurally stabilized (e.g., stapled or stitched) peptide is based on the amino acid sequence of SEQ ID NO:33 with 0 to 3 amino acid deletions from the C-terminus. In certain instances, the 1 to 3 amino acid in SEQ ID NO:6, 15, or 33 that are removed from the N-terminus are replaced with 1 to 6 amino acids from the croup consisting of alanine, D-alanine, α-aminoisobutyric acid, N-methyl glycine, serine, a substituted alanine, and a glycine derivative. In certain instances, the 1 to 3 amino acid in SEQ ID NO:6, 15, or 33 that are removed from the C-terminus are replaced with 1 to 6 amino acids from the croup consisting of alanine, D-alanine, α-aminoisobutyric acid, N-methyl glycine, serine, a substituted alanine, and a glycine derivative. In certain instances, the 1 to 6 amino acid substitutions relative to SEQ ID NO:6, 15, or 33 are of non-NHR-interacting residues. In certain instances, the 1 to 6 amino acid substitutions relative to SEQ ID NO:6, 15, or 33 are of NHR-interacting residues. In certain instances, the 1 to 6 amino acid substitutions relative to SEQ ID NO:6, 15, or 33 are of non-NHR-interacting residues and NHR-interacting residues.

In a specific instance, the structurally stabilized (e.g., stapled or stitched) peptide comprises an amino acid sequence of Formula (I), wherein $[Xaa]_w$ is HNWTK (SEQ ID NO:52), $[Xaa]_x$ is ITN, and $[Xaa]_y$ is INQIIHDFVNK (SEQ ID NO:51), $R_1$ is a methyl group, $R_2$ is a methyl group, and $R_3$ is 4-octenyl. In a specific instance, the structurally stabilized (e.g., stapled or stitched) peptide consists of an amino acid sequence of Formula (I), wherein $[Xaa]_w$ is HNWTK (SEQ ID NO:52), $[Xaa]_x$ is ITN, and $[Xaa]_y$ is INQIIHDFVNK (SEQ ID NO:51), $R_1$ is a methyl group, $R_2$ is a methyl group, and $R_3$ is 4-octenyl.

In a specific instance, the structurally stabilized (e.g., stapled or stitched) EBOV GP2 CHR peptide comprises a stapled form of the amino acid sequence of SEQ ID NO:15 (e.g., the product of a ring-closing metathesis reaction on SEQ ID NO:15). In a specific instance, the structurally stabilized (e.g., stapled or stitched) EBOV GP2 CHR peptide consists of a stapled form of the amino acid sequence of SEQ ID NO:15 (e.g., the product of a ring-closing metathesis reaction on SEQ ID NO:15).

In a specific instance, the structurally stabilized (e.g., stapled or stitched) peptide is based on the amino acid sequence of SEQ ID NO:4 with 0 to 6 (i.e., 0, 1, 2, 3, 4, 5, 6) amino acid substitutions, insertions, and/or deletions. In a specific instance, the structurally stabilized (e.g., stapled or stitched) peptide is based on the amino acid sequence of SEQ ID NO:14 with 0 to 6 (i.e., 0, 1, 2, 3, 4, 5, 6) amino acid substitutions, insertions, and/or deletions. In a specific instance, the structurally stabilized (e.g., stapled or stitched) peptide is based on the amino acid sequence of SEQ ID NO:4. In a specific instance, the structurally stabilized (e.g., stapled or stitched) peptide comprises the amino acid sequence of SEQ ID NO:4 with: (i) two or more amino acid substitutions with stapling amino acids, and (ii) 0 to 6 (i.e., 0, 1, 2, 3, 4, 5, 6) additional amino acid substitutions, insertions, and/or deletions. In a specific instance, the structurally stabilized (e.g., stapled or stitched) peptide consists of the amino acid sequence of SEQ ID NO:4 with: (i) two or more amino acid substitutions with stapling amino acids, and (ii) 0 to 6 (i.e., 0, 1, 2, 3, 4, 5, 6) additional amino acid substitutions, insertions, and/or deletions. In certain instances, the structurally stabilized (e.g., stapled or stitched) peptide is based on the amino acid sequence of SEQ ID NO:4 with 0 to 3 amino acid deletions from the N-terminus. In certain instances, the structurally stabilized (e.g., stapled or stitched) peptide is based on the amino acid sequence of SEQ ID NO:4 with 0 to 3 amino acid deletions from the C-terminus. In a specific instance, the structurally stabilized (e.g., stapled or stitched) peptide is based on the amino acid sequence of $HDWTKX_1ITDX_2INQIIHDFVNK$, wherein each of $X_1$ and $X_2$ is independently a stapling amino acid (SEQ ID NO:14). In a specific instance, the structurally stabilized (e.g., stapled or stitched) peptide comprises the amino acid sequence of $HDWTKX_1ITDX_2INQIIHDFVNK$, wherein each of $X_1$ and $X_2$ is independently a stapling amino acid (SEQ ID NO:14), and has 0 to 6 (i.e., 0, 1, 2, 3, 4, 5, 6) amino acid substitutions, insertions, and/or deletions relative to SEQ ID NO:14 at position(s) other than $X_1$ and $X_2$. In a specific instance, the structurally stabilized (e.g., stapled or stitched) peptide consists of the amino acid sequence of $HDWTKX_1ITDX_2INQIIHDFVNK$, wherein each of $X_1$ and $X_2$ is independently a stapling amino acid (SEQ ID NO:14), and has 0 to 6 (i.e., 0, 1, 2, 3, 4, 5, 6) amino acid substitutions, insertions, and/or deletions relative to SEQ ID NO:14 at position(s) other than $X_1$ and $X_2$. In certain instances, the structurally stabilized (e.g., stapled or stitched) peptide is based on the amino acid sequence of SEQ ID NO:14 with 0 to 3 amino acid deletions from the N-terminus. In certain instances, the structurally stabilized (e.g., stapled or stitched) peptide is based on the amino acid sequence of SEQ ID NO:14 with 0 to 3 amino acid deletions from the C-terminus. In a specific instance, the structurally stabilized (e.g., stapled or stitched) peptide comprises the amino acid sequence of $HDWTKX_1ITDX_2INQIIHDFVNK$, wherein each of $X_1$ and $X_2$ is (S)-2-(4'-pentenyl)Alanine (SEQ ID NO:32), and has 0 to 6 (i.e., 0, 1, 2, 3, 4, 5, 6) amino acid substitutions, insertions, and/or deletions relative to SEQ ID NO:32 at position(s) other than $X_1$ and $X_2$. In a specific instance, the structurally stabilized (e.g., stapled or stitched) peptide consists of the amino acid sequence of $HDWTKX_1ITDX_2INQIIHDFVNK$, wherein each of $X_1$ and $X_2$ is (S)-2-(4'-pentenyl)Alanine (SEQ ID NO:32), and has 0 to 6 (i.e., 0, 1, 2, 3, 4, 5, 6) amino acid substitutions, insertions, and/or deletions relative to SEQ ID NO:32 at position(s) other than $X_1$ and $X_2$. In certain instances, the structurally stabilized (e.g., stapled or stitched) peptide is based on the amino acid sequence of SEQ ID NO:32 with 0 to 3 amino acid deletions from the N-terminus. In certain instances, the structurally stabilized (e.g., stapled or stitched) peptide is based on the amino acid sequence of SEQ ID NO:32 with 0 to 3 amino acid deletions from the C-terminus. In certain instances, the 1 to 3 amino acid in SEQ ID NO:4, 14, or 32 that are removed from the N-terminus are replaced with 1 to 6 amino acids from the croup consisting of alanine, D-alanine, α-aminoisobutyric acid, N-methyl glycine, serine, a substituted alanine, and a glycine derivative. In certain instances, the 1 to 3 amino acid in SEQ ID NO: 4, 14, or 32 that are removed from the C-terminus are replaced with 1 to 6 amino acids from the croup consisting of alanine, D-alanine, α-aminoisobutyric acid, N-methyl glycine, serine, a substituted alanine, and a glycine derivative. In certain instances, the 1 to 6 amino acid substitutions relative to SEQ ID NO: 4, 14, or 32 are of non-NHR-interacting residues. In certain instances, the 1 to 6 amino acid substitutions relative to SEQ ID NO: 4, 14, or 32 are of NHR-interacting residues. In certain instances, the 1 to 6 amino acid substitutions relative to SEQ ID NO: 4, 14, or 32 are of non-NHR-interacting residues and NHR-interacting residues.

In a specific instance, the structurally stabilized (e.g., stapled or stitched) peptide comprises an amino acid sequence of Formula (I), wherein [Xaa]W is HDWTK (SEQ ID NO:50), $[Xaa]_x$ is ITD, and $[Xaa]_y$ is INQIIHDFVNK (SEQ ID NO:51), $R_1$ is a methyl group, $R_2$ is a methyl group, and $R_3$ is 4-octenyl. In a specific instance, the structurally stabilized (e.g., stapled or stitched) peptide consists of an amino acid sequence of Formula (I), wherein $[Xaa]_w$ is HDWTK (SEQ ID NO:50), $[Xaa]_x$ is ITD, and $[Xaa]_y$ is INQIIHDFVNK (SEQ ID NO:51), $R_1$ is a methyl group, $R_2$ is a methyl group, and $R_3$ is an alkenyl.

In a specific instance, the structurally stabilized (e.g., stapled or stitched) EBOV GP2 CHR peptide comprises a stapled form of the amino acid sequence of SEQ ID NO:14 (e.g., the product of a ring-closing metathesis reaction on SEQ ID NO:14). In a specific instance, the structurally stabilized (e.g., stapled or stitched) EBOV GP2 CHR peptide consists of a stapled form of the amino acid sequence of SEQ ID NO:14 (e.g., the product of a ring-closing metathesis reaction on SEQ ID NO:14).

In certain instances, each of the EBOV GP2 CHR structurally stabilized peptides described above bind to a 5 helix bundle of EBOV GP2 or fusion bundle intermediate of EBOV GP2. In some instances, the EBOV GP2 CHR structurally stabilized peptides described above prevent or block fusion of the virus and host membranes.

Therapeutic Uses

The disclosure features methods of using any of the structurally stabilized (e.g., stapled or stitched) peptides (or pharmaceutical compositions comprising said structurally stabilized peptides) described herein for the prevention and/or treatment of an Ebola virus infection or Ebola virus disease. The terms "treat" or "treating," as used herein, refers to alleviating, inhibiting, or ameliorating the disease or infection from which the subject is suffering.

The structurally stabilized (e.g., stapled or stitched) peptides (or compositions comprising the peptides) described herein can be useful for treating a subject (e.g., human, non-human primate, or fruit bat) having an Ebolavirus infection. The structurally stabilized (e.g., stapled or stitched) peptides (or compositions comprising the peptides) described herein can also be useful for treating a subject (e.g., human, non-human primate, or fruit bat) having an Ebolavirus disease. In certain instances, the Ebolavirus infection is a Zaire ebolavirus infection. In certain instances, the Ebolavirus disease is caused by a Zaire ebolavirus infection. In certain instances, the Ebolavirus infection is a Bundibugyo ebolavirus infection. In certain instances, the Ebolavirus disease is caused by a Bundibugyo ebolavirus infection. In certain instances, the Ebolavirus infection is a Sudan ebolavirus infection. In certain instances, the Ebolavirus disease is caused by a Sudan ebolavirus infection. In certain instances, the Ebolavirus infection is a Tai Forest ebolavirus infection. In certain instances, the Ebolavirus disease is caused by a Tai Forest ebolavirus infection.

The structurally stabilized (e.g., stapled or stitched) peptides (or compositions comprising the peptides) described herein can be useful for preventing an Ebola virus infection in a subject. The peptides (or compositions comprising the peptides) described herein can also be useful for preventing an Ebola virus disease in a subject. In certain instances, the Ebola virus infection is a Zaire ebolavirus infection. In certain instances, the Ebola virus disease is caused by a Zaire ebolavirus infection. In some instances, the subject is a human. In some instances, the subject is a non-human primate. In some instances, the subject is a fruit bat.

In certain instances, the subject in need thereof is administered a peptide described in Table 2 (i.e., any one of SEQ ID NOs: 7-42). In certain instances, the subject in need thereof is administered a stapled EBOV GP2 CHR peptide comprising or consisting of SEQ ID NO:15 or a modified version thereof. In certain instances, the subject in need thereof is administered a stapled EBOV GP2 CHR peptide comprising or consisting of SEQ ID NO:14 or a modified version thereof. In some instances, the subject is a human. In some instances, the subject is anon-human primate. In some instances, the subject is a fruit bat.

In certain instances, the subject in need thereof is administered any one of constructs 1-17 described in Table 3 or construct 18 described in Table 4. In certain instances, the subject in need thereof is administered construct 9 described in Table 3. In certain instances, the subject in need thereof is administered construct 8 described in Table 3. In some instances, the subject is a human. In some instances, the subject is a non-human primate. In some instances, the subject is a fruit bat.

In certain instances, the subject in need thereof is administered a peptide described in Table 4 (i.e., any one of SEQ ID NOs: 2, 25, 28, 37, 42, 40, 34, 41, 35, and 36). In certain instances, the subject in need thereof is administered a peptide having SEQ ID NO:28. In certain instances, the subject in need thereof is administered a peptide having SEQ ID NO:37. In certain instances, the subject in need thereof is administered a peptide having SEQ ID NO:42. In certain instances, the subject in need thereof is administered a peptide having SEQ ID NO:35. In some instances, the subject is infected with an Ebola virus. In some instances, the subject is at risk of being infected with an Ebola virus. In some instances, the subject is at risk of developing an Ebola virus disease. In some instances, a subject is at risk of being infected with an Ebola virus or at risk of developing an Ebola virus disease if he or she lives in an area (e.g., city, state, country) subject to an active Ebola virus outbreak (e.g., an area where at least 1, at least 2, at least 3, at least 4, at least 5, at least 6, at least 7, at least 8, at least 9, at least 10, at least 20, at least 30, at least 40, or more people have been diagnosed as infected with Ebola virus). In some instances, a subject is at risk of being infected with an Ebola virus or developing an Ebola virus disease if he or she lives in an area near (e.g., a bordering city, state, country) a second area (e.g., city, state, country) subject to an active Ebola virus outbreak (e.g., an area near (e.g., bordering) a second area where at least 1, at least 2, at least 3, at least 4, at least 5, at least 6, at least 7, at least 8, at least 9, at least 10, at least 20, at least 30, at least 40, or more people have been diagnosed as infected with Ebola virus). In some instances, the Ebola virus is Zaire ebolavirus. In some instances, the subject is a human. In some instances, the subject is a non-human primate. In some instances, the subject is a fruit bat.

In general, methods include selecting a subject and administering to the subject an effective amount of one or more of the structurally stabilized (e.g., stapled or stitched) peptides herein, e.g., in or as a pharmaceutical composition, and optionally repeating administration as required for the prevention or treatment of an Ebola virus infection or Ebola virus disease and can be administered orally, intravenously or topically. A subject can be selected for treatment based on, e.g., determining that the subject has an Ebola virus infection. The peptides of this disclosure can be used to determine if a subject's is infected with an Ebola virus.

The structurally stabilized (e.g., stapled or stitched) peptides (or compositions comprising the peptides) described herein can be useful for preventing transmission of an Ebolavirus infection from a first subject to a second subject, the method comprising administering to the first subject a therapeutically-effective amount of a structurally stabilized peptide described herein, wherein the first subject is a human or a non-human primate or a fruit bat. In some instances, the second subject is a human.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected.

The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. For example, effective amounts can be administered at least once.

Pharmaceutical Compositions

One or more of any of the structurally stabilized (e.g., stapled or stitched) peptides described herein can be formulated for use as or in pharmaceutical compositions. The pharmaceutical compositions may be used in the methods of treatment or prevention described herein (see above). In certain instances, the pharmaceutical composition comprises a structurally stabilized (e.g., stapled or stitched) peptide comprising or consisting of an amino acid sequence that is identical to an amino acid sequence set forth in Table 2, except for 1 to 10, 1 to 9, 1 to 8, 1 to 7, 1 to 6, 1 to 5, 1 to 4, 1 to 3, 1 to 2, or 1 amino acid substitution, insertion, or deletion. These changes to the amino acid sequences can be made on the non-NHR-interacting alpha-helical face of these peptides (i.e., to the amino acids that do not interact with the EBOV GP2 NHR) and/or on the NHR-interacting alpha-helical face (i.e., to the amino acids that interact with the EBOV GP2 NHR). Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions).

In some instances, pharmaceutical compositions can include an effective amount of one or more structurally stabilized (e.g., stapled or stitched) peptides. The terms "effective amount" and "effective to treat," as used herein, refer to an amount or a concentration of one or more structurally stabilized (e.g., stapled or stitched) peptides or a pharmaceutical composition described herein utilized for a period of time (including acute or chronic administration and periodic or continuous administration) that is effective within the context of its administration for causing an intended effect or physiological outcome (e.g., treatment of infection).

Pharmaceutical compositions of this invention can include one or more structurally stabilized (e.g., stapled or stitched) peptides described herein and any pharmaceutically acceptable carrier and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

In some instances, one or more structurally stabilized (e.g., stapled or stitched) peptides disclosed herein can be conjugated, for example, to a carrier protein. Such conjugated compositions can be monovalent or multivalent. For example, conjugated compositions can include one structurally stabilized (e.g., stapled or stitched) peptide disclosed herein conjugated to a carrier protein. Alternatively, conjugated compositions can include two or more structurally stabilized (e.g., stapled or stitched) peptides disclosed herein conjugated to a carrier.

As used herein, when two entities are "conjugated" to one another they are linked by a direct or indirect covalent or non-covalent interaction. In certain instances, the association is covalent. In other instances, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., *Infect. Immun.,* 58:2309-2312, 1990; Devi et al., *Proc. Natl. Acad. Sci. USA* 88:7175-7179, 1991; Li et al., *Infect. Immun.* 57:3823-3827, 1989; Szu et al., *Infect. Immun.* 59:4555-4561, 1991; Szu et al., *J Exp. Med.* 166:1510-1524, 1987; and Szu et al., *Infect. Immun.* 62:4440-4444, 1994). Polymeric carriers can be a natural or a synthetic material containing one or more primary and/or secondary amino groups, azido groups, or carboxyl groups. Carriers can be water soluble.

Methods of Making Structurally-Stabilized Peptides

Also provided herein are methods of making structurally-stabilized peptides (e.g., a structurally-stabilized peptide described herein). In some instances, the method comprises (a) providing a peptide described herein, wherein the peptide comprises two or more stapling amino acids (e.g., a peptide comprising an amino acid sequence set forth in any one of SEQ ID NOs: 7-42) or a variant thereof, and (b) performing a ring-closing metathesis reaction. In some instances, the method further comprises repeating step (b) one to four additional times (i.e., performing a total of 3 to 5 ring-closing metathesis reactions. In some instances, the method comprises: (a) providing a peptide having the sequence set forth in any one of SEQ ID NOs: 2-6 or a variant thereof, and (b) cross-linking the peptide. In some instances, the method further comprises formulating the structurally-stabilized peptide as a pharmaceutical composition.

In some instances, the peptides produced by the methods of making the structurally-stabilized peptides are the structurally stabilized peptides such as those set forth in SEQ ID NOs: 7-42, as well as variants thereof.

Fmoc-based solid-phase peptide synthesis may be used to synthesize the structurally stabilized peptides described herein (e.g., in accordance with reported methods for generating all-hydrocarbon stapled peptides, e.g., Bird, G. H., Crannell, W. C. & Walensky, L. D. Chemical synthesis of hydrocarbon-stapled peptides for protein interaction research and therapeutic targeting. Curr. Protoc. Chem. Biol. 3, 99-117 (2011)). For example, to achieve the various staple lengths, α-methyl, α-alkenyl amino acids may be installed at i, i+4 positions using two (S)-pentenyl alanine residues (S5) and at i, i+7 positions by inserting (R)-octenyl alanine (R8) at the i position and S5 at the i+7 position, or by inserting (R)-pentenyl alanine (R5) at the i position and (S)-octenyl alanine (S8) at the i+7 position. For the stapling reaction, Grubbs first-generation ruthenium catalyst dissolved in dichloroethane is added to the resin-bound peptides. To ensure maximal conversion, 3-5 rounds of stapling may be performed. The peptides are then cleaved off of the resin using, e.g., trifluoroacetic acid, precipitated using, e.g., a hexane:ether (1:1) mixture, air dried and purified by, e.g., LC-MS. Peptides may be quantified by amino acid analysis. TFA-HCl exchange may be performed on peptides to be used in animal studies.

Methods of synthesizing the structurally stabilized (e.g., stapled or stitched) peptides described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech. Peptide bonds can be replaced, e.g., to increase physiological stability of the peptide, by: a retro-inverso bonds (C(O)—NH); a reduced amide bond (NH—$CH_2$); a thiomethylene bond (S—CH2 or CH2-S); an oxomethylene bond (O—$CH_2$ or $CH_2$—O); an ethylene bond ($CH_2$—$CH_2$); a thioamide bond (C(S)—NH); a trans-olefin bond (CH═CH); a fluoro substituted trans-olefin bond (CF═CH); a ketomethylene bond (C(O)—CHR) or CHR—C(O) wherein R is H or $CH_3$; and a fluoro-ketomethylene bond (C(O)—CFR or CFR—C(O) wherein R is H or F or $CH_3$.

The peptides can be further modified by: cholesterolization, acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., $C_1$-$C_{20}$ straight or branched alkyl groups); fatty acid radicals; and combinations thereof. α, α-Disubstituted non-natural amino acids containing olefinic side chains of varying length can be synthesized by known methods (Williams et al. J. Am. Chem. Soc., 113: 9276, 1991; Schafmeister et al., J. Am. Chem Soc., 122: 5891, 2000; and Bird et al., Methods Enzymol., 446:369, 2008; Bird et al, Current Protocols in Chemical Biology, 2011). For peptides where an i linked to i+7 staple is used (two turns of the helix stabilized) either: a) one (S)-2-(4'-pentenyl)Alanine amino acid and one (R)-2-(7'-octenyl) Alanine is used; or b) one (S)-2-(7'-octenyl)Alanine amino acid and one (R)-2-(4'-pentenyl)Alanine amino acid is used. (R)-2-(7'-octenyl)Alanine is synthesized using the same route, except that the starting chiral auxiliary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-(S)-2-(4'-pentenyl)Alanine-OH, Fmoc-(R)-2-(7'-octenyl)Alanine-OH, Fmoc-(S)-2-(7'-octenyl)Alanine-OH, and Fmoc-(R)-2-(4'-pentenyl)Alanine-OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, CA). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., Org. Synth., 80:31, 2003).

Again, methods suitable for obtaining (e.g., synthesizing), stapling or stitching, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafmeister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety).

In some instances, the structurally stabilized (e.g., stapled or stitched) peptides are substantially free of non-stabilized peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific instance, a 50%/50% DMSO/NMP solution is used. The solution may be incubated for a period of 1, 6, 12 or 24 hours, following which the resin may be washed, for example with dichloromethane or NMP. In one instance, the resin is washed with NMP. Shaking and bubbling an inert gas into the solution may be performed.

Also provided herein is a method of producing a structurally stabilized (e.g., stapled or stitched) peptide comprising: (a) stapling or stitching an EBOV GP2 CHR peptide (or variant thereof); and (b) isolating the stapled or stitched peptide. The method may further involve formulating the stapled or stitched peptide into a pharmaceutical composition.

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

EXAMPLES

Example 1. Design and Synthesis of Stapled Ebola Virus Peptides (SEboV)

Figure 2:
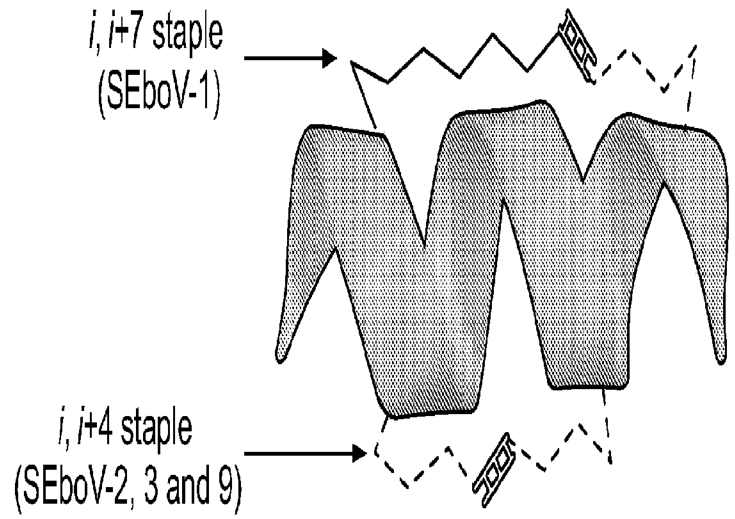
FIG. 2 shows designs of stapled Ebola virus peptides based on amino acids 613-633 of EBOV GP2 (SEQ ID NO:1). Top: schematic of stapled Ebola virus (SEboV) peptide; Bottom: amino acid sequences of SEboV peptides and unstapled precursor peptide (WT EboV); the charge of each of the peptides is indicated on the right. SEQ ID NOs: 2, 39, 29, 32, and 33 (from top to bottom, respectively). First (from N-terminal) *: (R)-2-(7'-octenyl) alanine; second *: (S)-2-(4'-pentenyl)Alanine.

In designing compounds that could block the formation of the hemifusion complex, a helical wheel analysis was performed of residues 613-630 within the 613-633 amino acid sequence of EBOV GP2 (SEQ ID NO: 1) (FIG. 1). This analysis determined which residues would be amenable to substitution for hydrocarbon cross-linking amino acids for peptide stapling. The helical analysis clearly revealed the confluence of multiple C-terminal helical heptad repeat (CHR) hydrophobic residues at the binding interface with N-terminal helical heptad repeat (NHR) (FIG. 1) that are likely to provide the driving force for the cooperative formation of the six-helix bundle. Thus, these residues were left intact and the stapling elements were placed on the opposite face of the helix. One additional consideration in the design involved ensuring that the compounds retain the ability to enter eukaryotic cells. There are multiple physicochemical properties that can modulate the cell permeability (e.g., the ability to be taken up by endosomes) of stapled peptides and, among these, are overall hydrophobic content, peptide helicity, and overall charge in solution (depending on the context, excess negative charge can impair membrane interaction and uptake). The parent peptide WT EboV (SEQ ID NO: 2), which is based entirely on the unmodified sequence of EBOV613-633 (FIG. 2) has a charge of −2 at physiological pH. Stapled Ebola virus (SEboV) peptides were designed to control peptide charge by placing the crosslinking amino acids at a location that contains aspartic acid residues, by replacing them for their isosteric asparagine counterparts, or by a combination of both. These changes yielded a family of four SEboV peptides (SEQ ID NOs: 39, 29, 32, and 33) with different staple locations, sizes, and charges (FIG. 2).

Example 2. SEboV Peptides were Helical and Bound to a Truncated Mimetic of EBOV GP2

Figure 3:
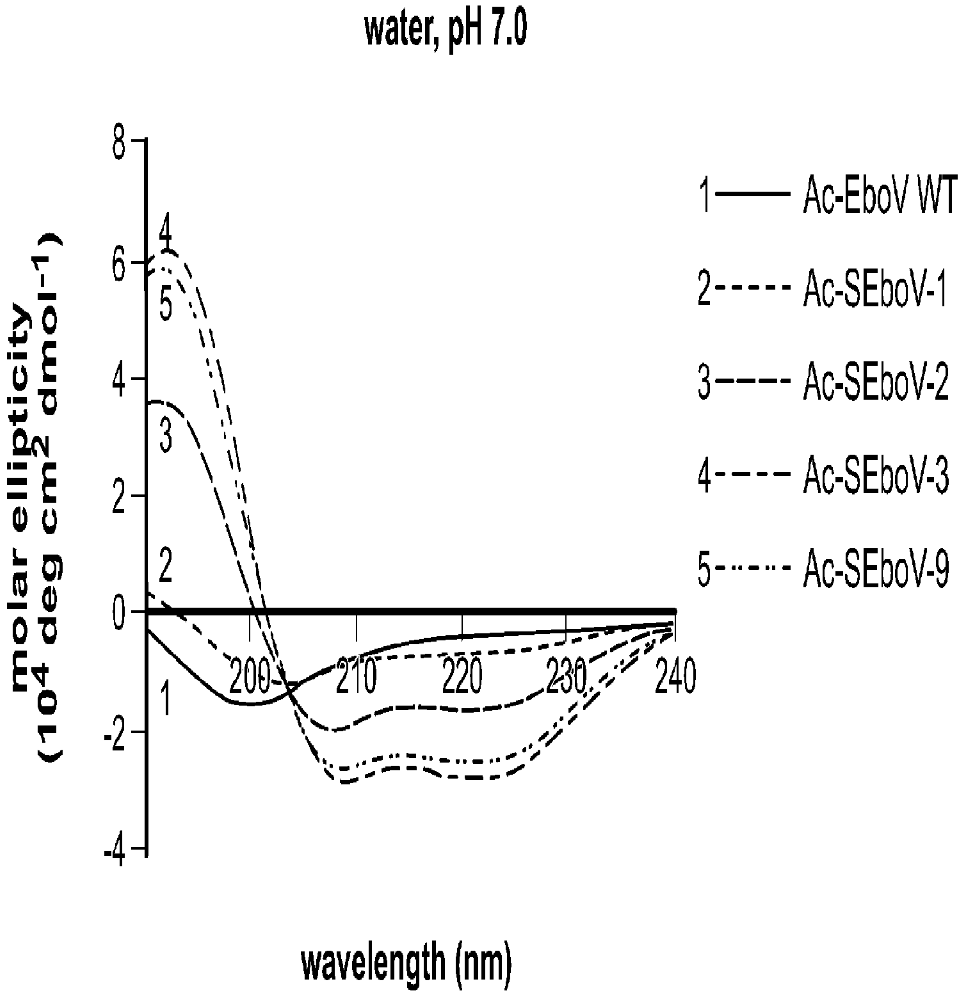
FIG. 3 shows a circular dichroism spectra of N-terminal acetylated (Ac) SEboV peptides in water at pH 7.0.
Figure 4:
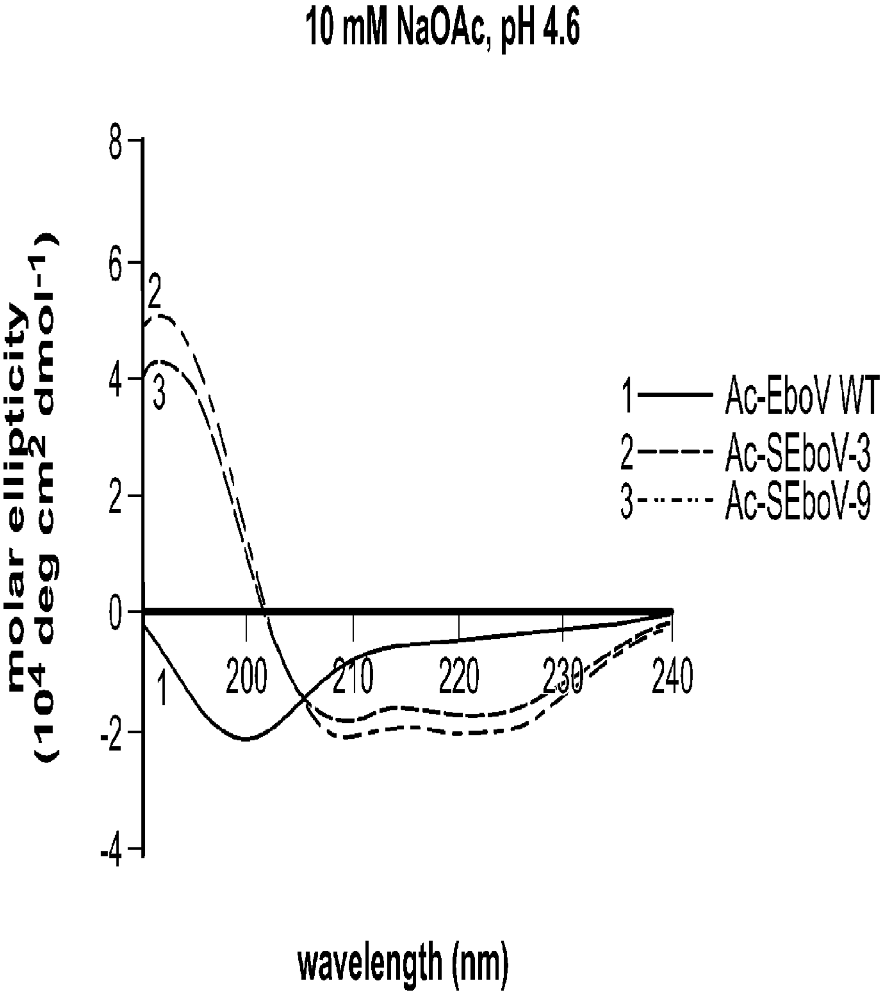
FIG. 4 shows a circular dichroism spectra of N-terminal acetylated (Ac) SEboV peptides at an endosomal pH in acetate buffer (pH 4.6).
Figure 5:
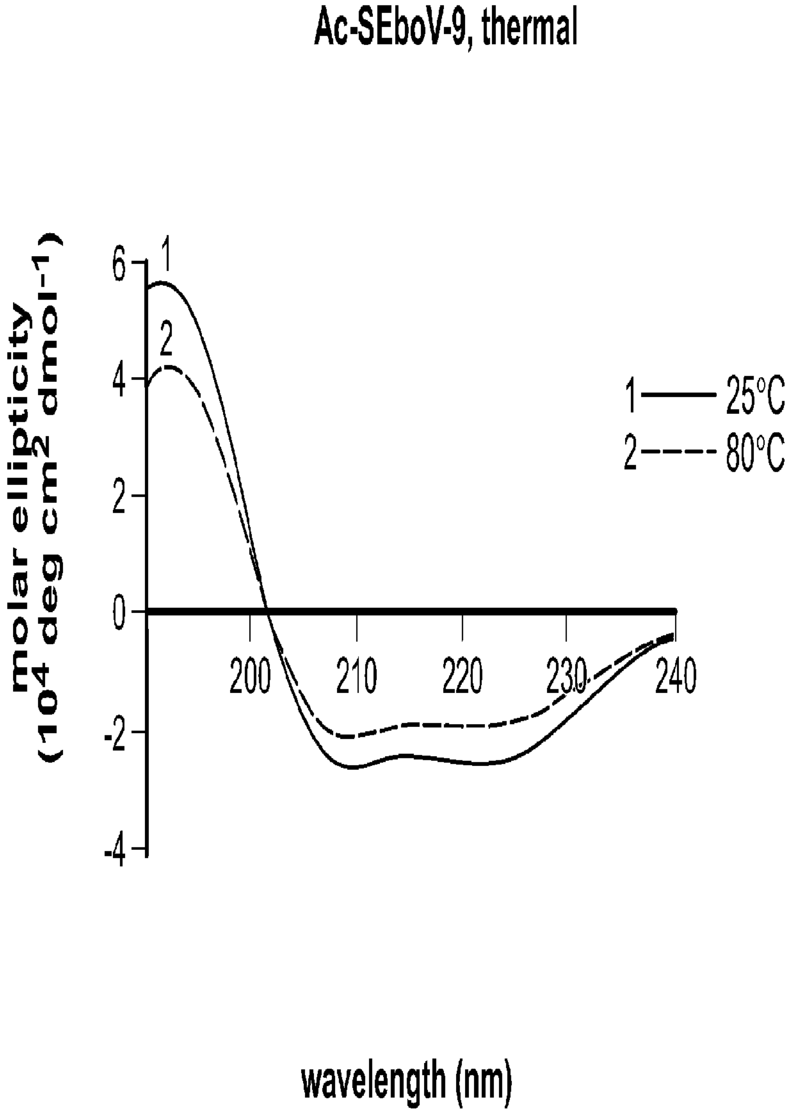
FIG. 5 shows thermal denaturation of Ac-SEboV-9. The peptide was dissolved in 10 mM pH 4.6 acetate buffer, and spectra were acquired at 25° C. and 80° C.
Figure 6:
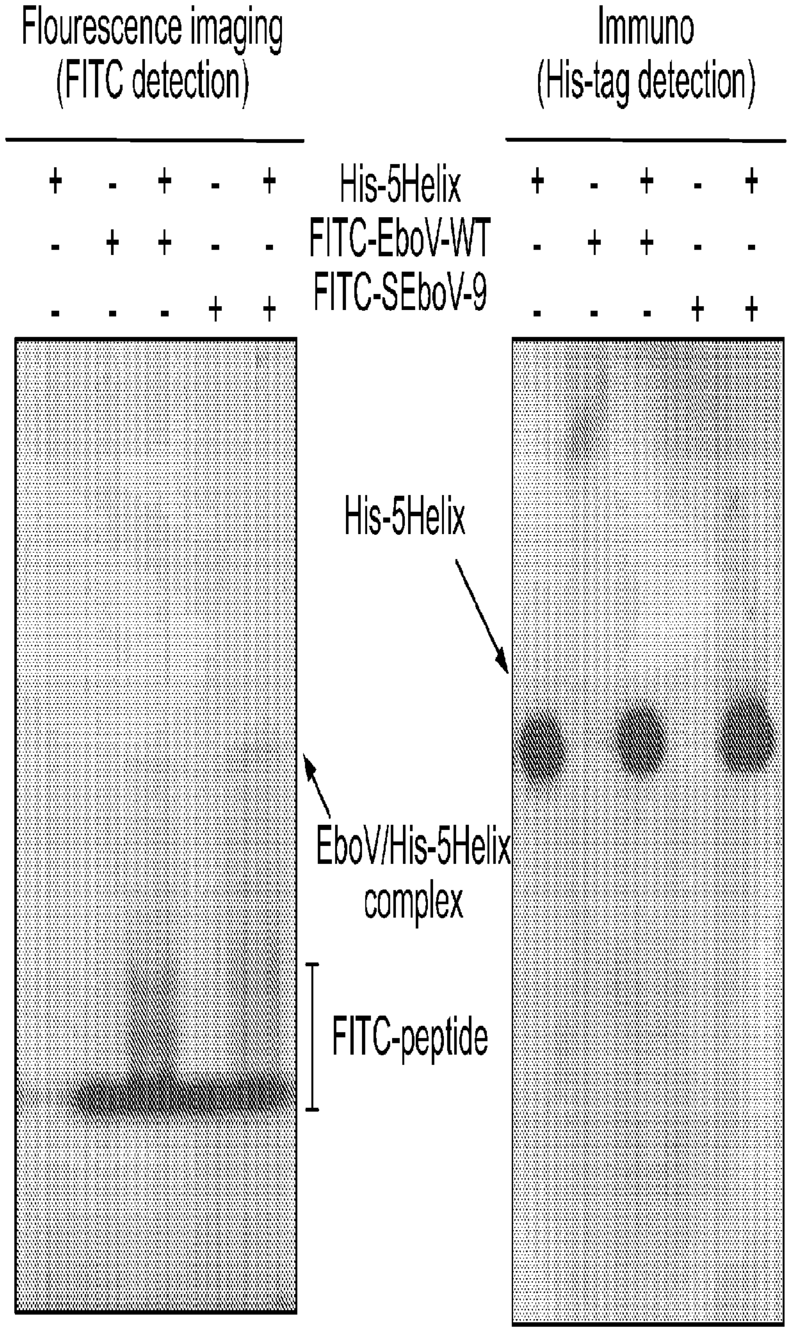
FIG. 6 shows a high resolution clear native electrophoresis of FITC Ebola virus peptides in the presence of histidine-tagged 5Helix. The gel was imaged on a fluorescence imager to detect FITC-peptides (left) and then immunoblotted against a His-tag antibody to detect His-5Helix (right).
Figure 7:
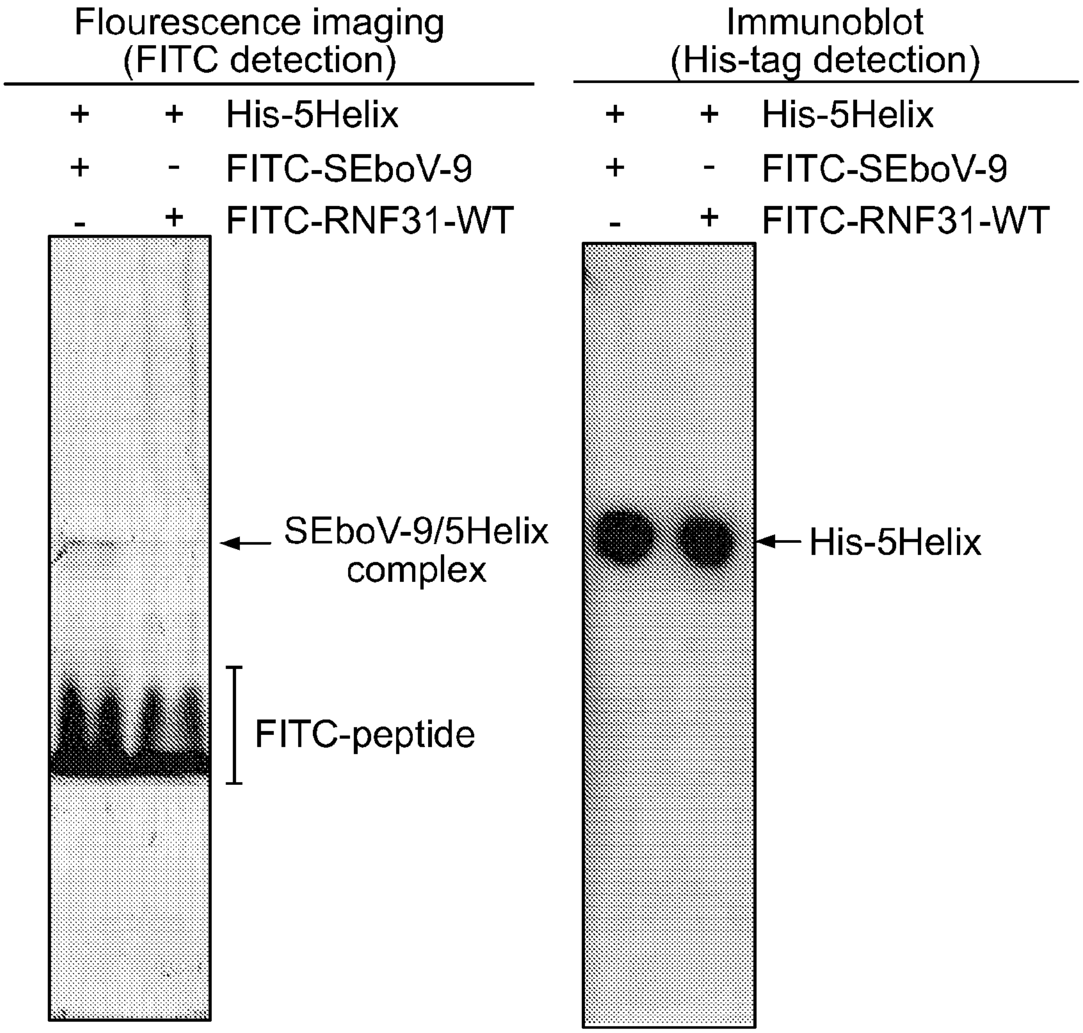
FIG. 7 shows a high resolution clear native electrophoresis of FITC-SEboV-9 (SEQ ID NO:33) and FITC-RNF31-WT (control; SEQ ID NO:68) peptides in the presence SEboV-9 of histidine-tagged 5Helix. The gel was imaged on a fluorescence imager to detect FITC-peptides (left) and then immunoblotted against a His-tag antibody to detect His-5Helix (right).
Figure 8:
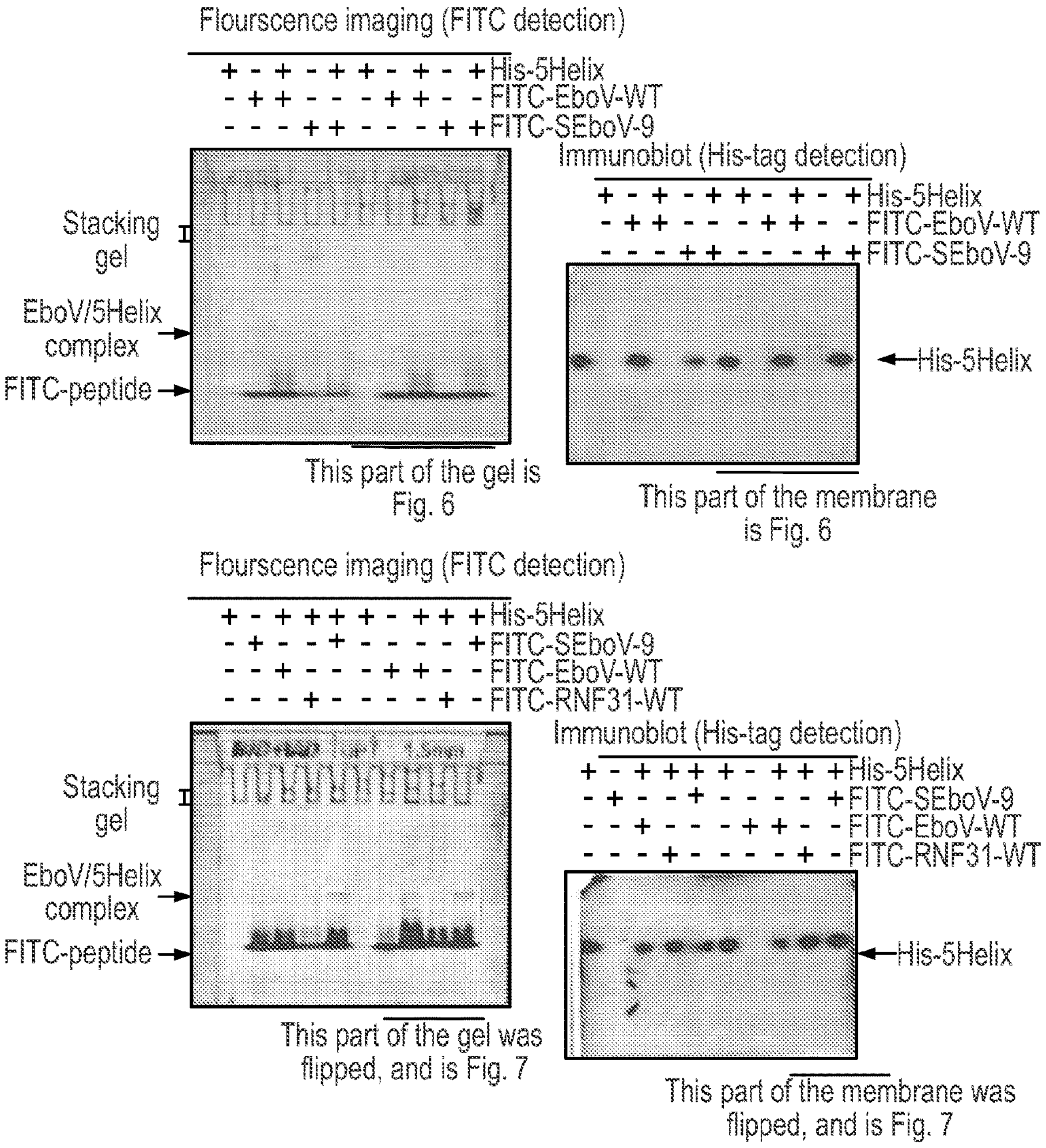
FIG. 8 shows the complete gels and blots from FIG. 6 and FIG. 7.

The helical propensity of the designed compounds was evaluated by circular dichroism (CD) spectroscopy in water (FIG. 3). The spectra revealed that the WT EboV parent peptide is unstructured in water, whereas all SEboV peptides displayed a CD spectrum characteristic of an α-helix. Changes in the protonation state of a peptide could have an impact on its structure. Since the site of action of SEboV peptides is a late endosome in which the pH is 4.5-5.0, the helical propensity of the compounds was tested at pH 4.6 (FIG. 4). SEboV peptides remained structured despite the pH change. The thermal stability of the compounds was evaluated under denaturing conditions, and no appreciable changes in their CD spectrum were observed (FIG. 5). To determine whether SEboV peptides interfered with the assembly of the six-helix bundle post-fusion complex, high resolution clear native electrophoresis (hrCNE) was conducted. A histidine-tagged EBOV GP2 ectodomain construct that lacks one of the CHR helices in the post-fusion complex (His-5Helix) was expressed and incubated with either FITC-labeled WT EboV peptide or FITC-SEboV-9, both of which were based on the sequence of the deleted CHR. After electrophoresis, the gel was imaged in a fluorescence scanner to detect the migration of the FITC-labeled species (FIG. 6, left) and then immunoblotted to reveal the location of the His-5Helix (FIG. 6, right). The results showed that both FITC WT EboV and, to a greater extent, FITC-SEboV-9, co-migrated with His-5Helix, suggesting that the CHR-derived peptides could easily occupy the space left by the missing helix in this construct. The specificity of the interaction was confirmed by combining His-5Helix with FITC-RNF31-WT (SEQ ID NO:68), an unrelated stapled peptide, and seeing no co-migration of the species, which was indicative of no binding (FIG. 7 and FIG. 8). Taken together, these data demonstrated that SEboV peptides retained helical stabilization under a wide array of conditions and could potentially block the assembly of the post-fusion complex.

Example 3. SEboV Peptides Colocalized with Endosomes

Figure 9:
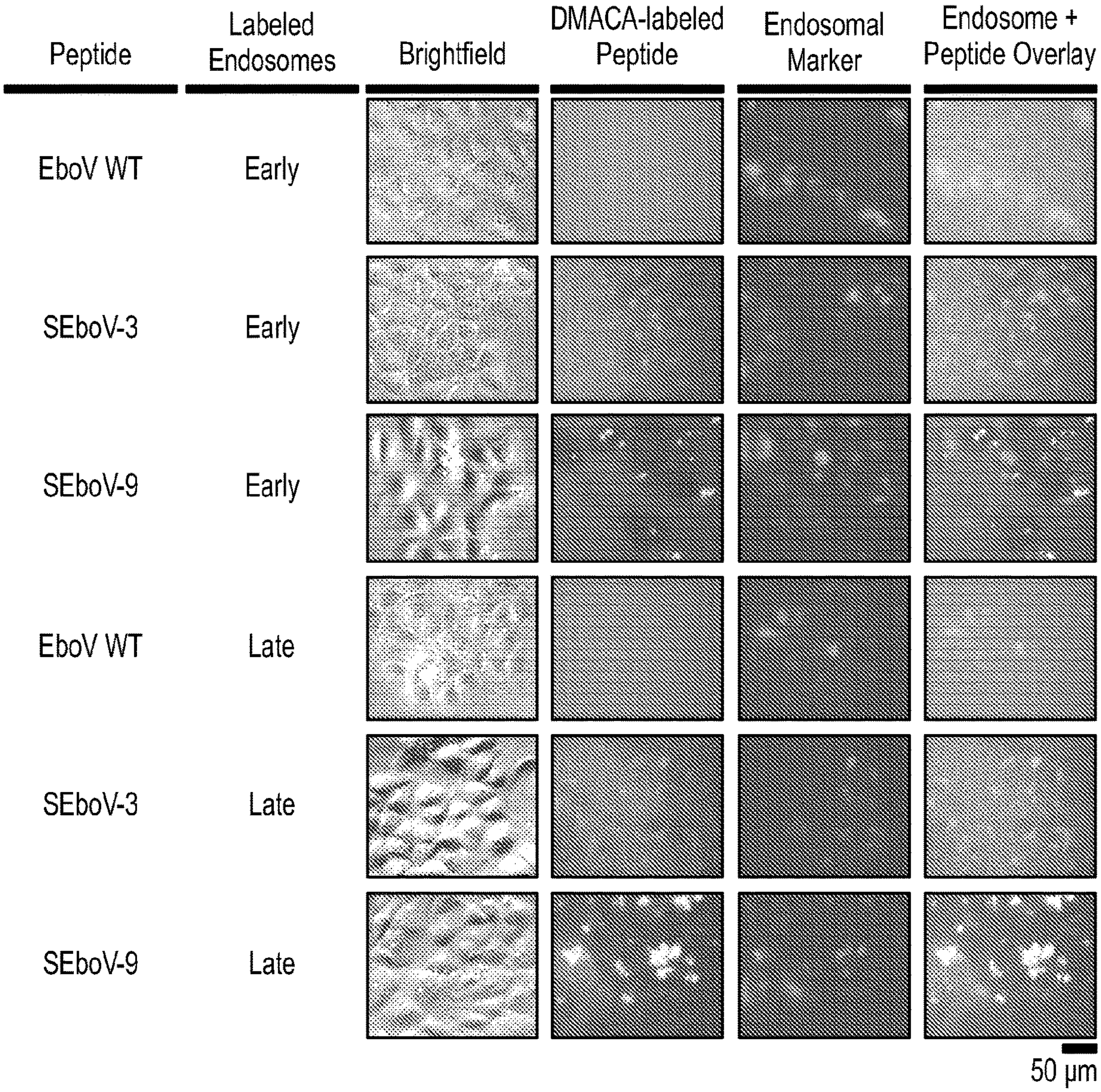
FIG. 9. Live cell fluorescence microscopy of Huh-7 hepatocellular carcinoma cells treated with DMACA-labelled-WT EboV, -SEboV-3, or -SEboV-9 (third column of images from right) in the presence of either late or early endosomal markers (second column of images from right).

Having demonstrated the pH and thermal stability of SEboV peptides as well as their ability to assemble with GP2, the ability of these peptides to enter cells was examined. To ascertain the endosomal localization of SEboV peptides upon uptake, live cell fluorescence microscopy was performed. Due to the acidic nature of the endosomal compartment, compounds with N,N-dimethylaminocoumarin (DMACA), a pH-insensitive fluorescent dye were tagged. Huh-7 hepatocellular carcinoma cells were exposed to DMACA-labeled WT EboV, SEboV-3, and SEboV-9 peptides and to either an early or late endosomal marker (FIG. 9). Live cell fluorescence microscopy images showed that, whereas WT EboV was not cell permeable and SEboV-3 was marginally so, SEboV-9 readily penetrated cells and colocalized with late endosomes. These results suggested that SEboV, in particular, SEboV-9, could effectively target EBOV infection.

Example 4. SEboV Peptides Prevented EBOV Infection

Figure 10:
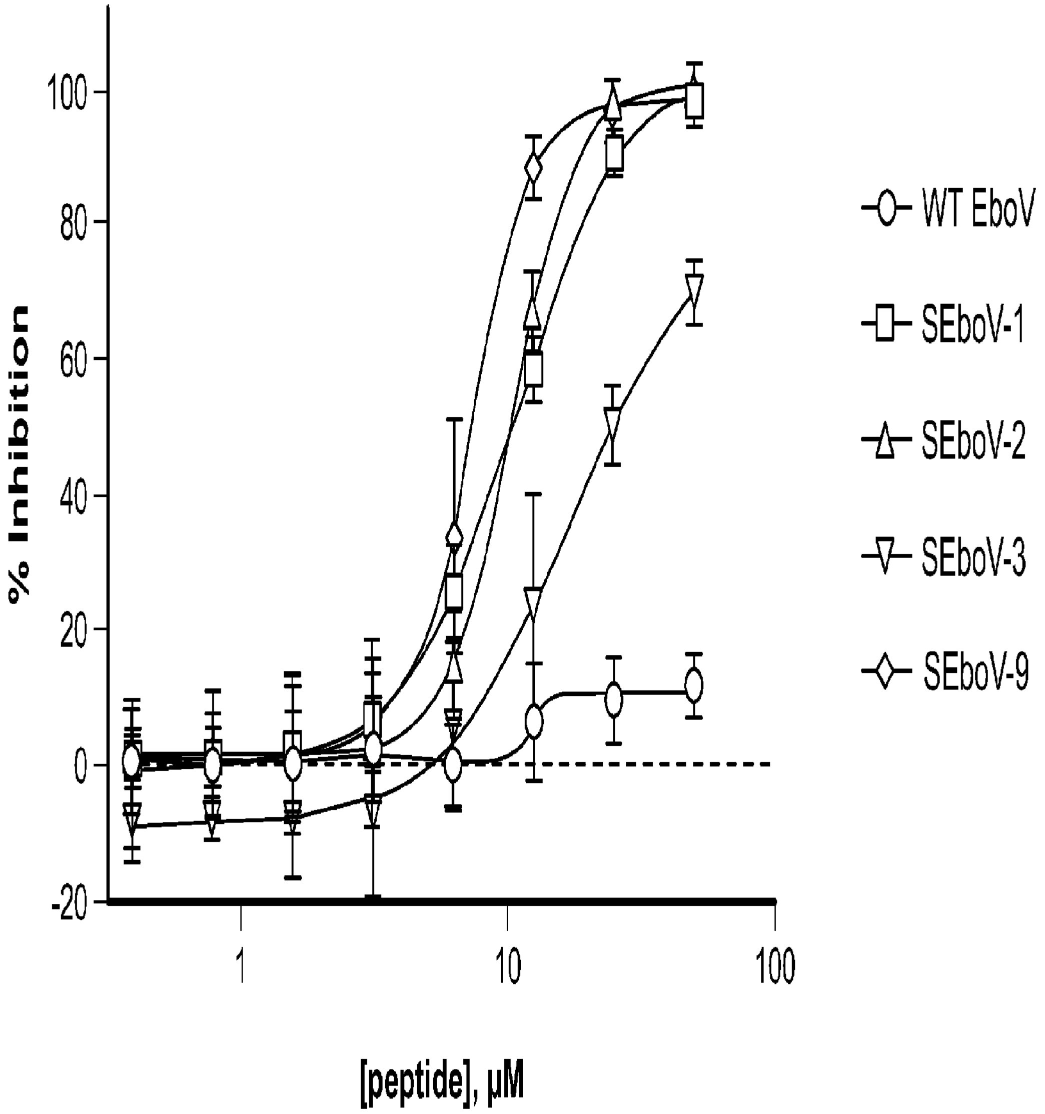
FIG. 10 shows percent inhibition of infectivity (assessed by ELISA) of Makona variant of EBOV in Huh-7 cells exposed to WT EboV peptide, or SEboV-1, SEboV-2, SEboV-3, or SEboV-9 stapled peptides.
Figure 11:
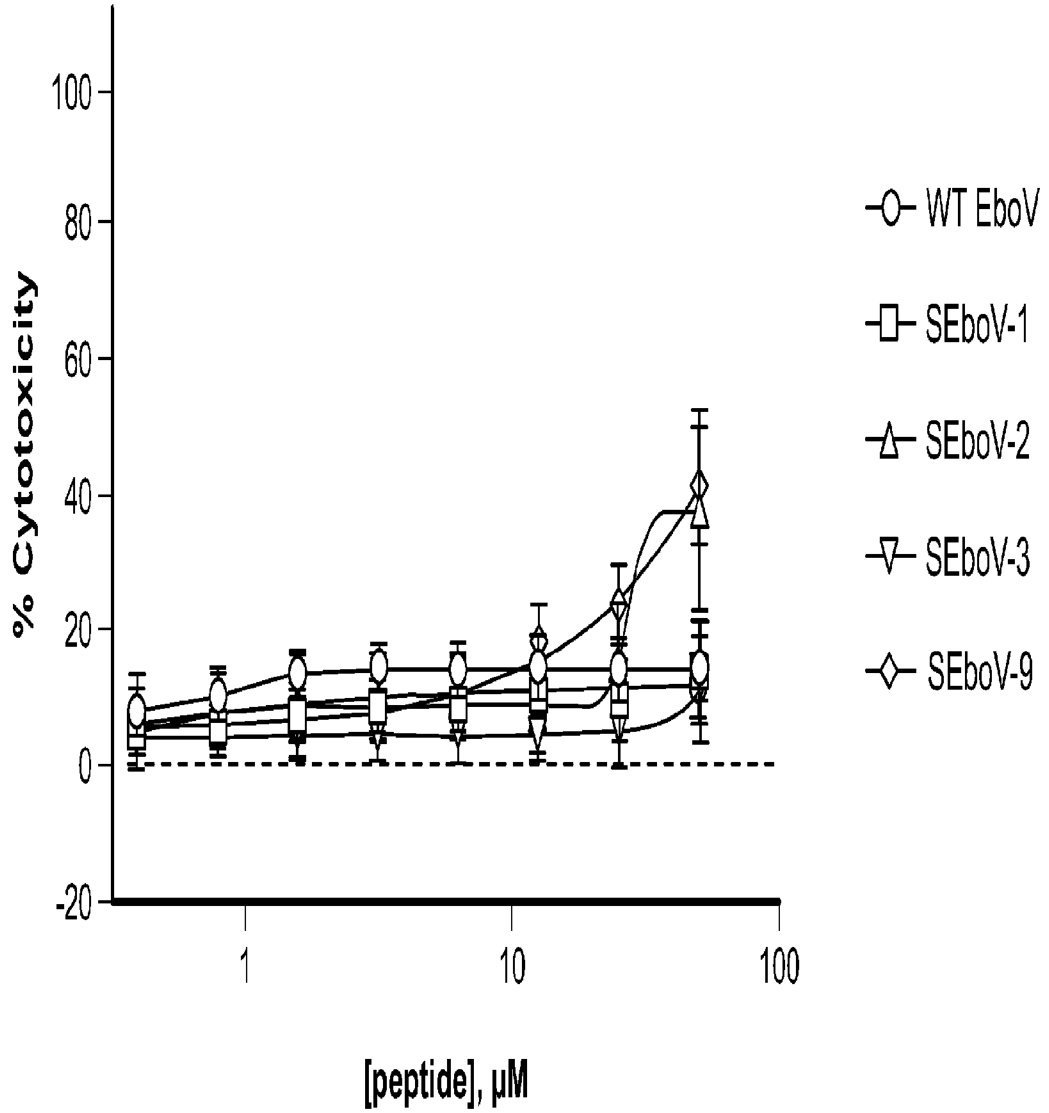
FIG. 11 shows cytotoxicity profile of SEboV-1, SEboV-2, SEboV-3, or SEboV-9 stapled peptides compared to WT EboV.

Once it was determined that SEboV peptides enter cells by endosomal uptake in a similar manner as EBOV, the ability of the compounds to block viral infection was evaluated. To examine the efficacy of the compounds, Huh-7 hepatocellular carcinoma cells were pretreated with Ac-SEboV peptides and were then exposed to the Makona variant of EBOV. After exposure, the cells were incubated for 48 hours, fixed, and analyzed for drug efficacy and cell toxicity. The WT EboV parent peptide was ineffective at preventing infection; however, compounds SEboV-1, 2, and 9 all displayed antiviral activity (FIG. 10). SEboV-3 had marginal antiviral activity, presumably due to its limited ability to enter cells (FIG. 9). Importantly the compounds displayed little cytotoxicity at the dose range tested (FIG. 11) indicating good separation of antiviral activity from toxic effects in cell culture.

Figure 12:
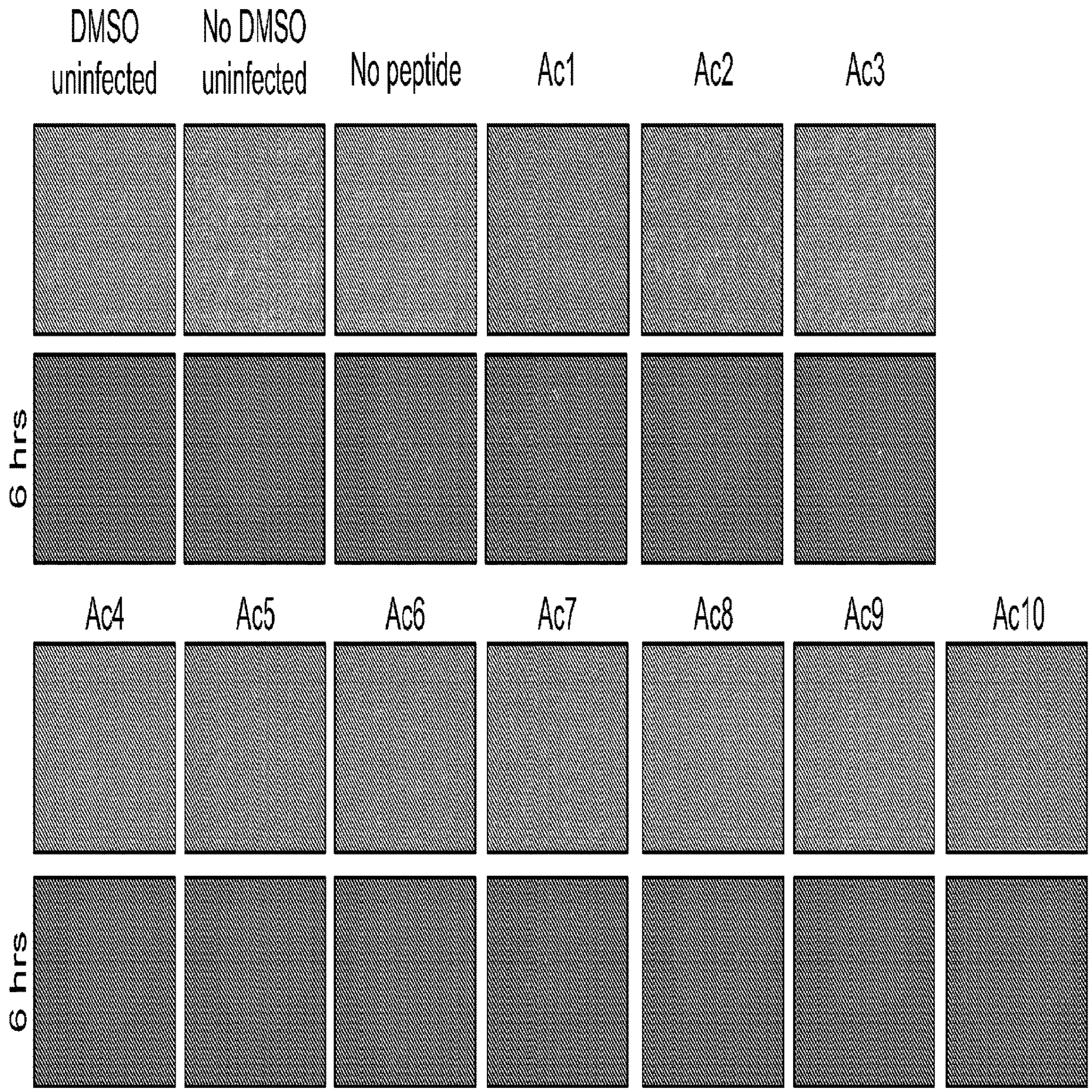
FIG. 12 shows immunofluorescence at 6 hours post-infection of Vero cells infected with Ebola virus after preincubation of the virus with the indicated peptides. Ac1-Ac10 are N-terminally acetylated versions of peptides having the amino acid sequence set forth in SEQ ID NOs: 2, 25, 28, 37, 42, 40, 34, 41, 35, and 36, respectively. The top row for each sample depicts the nuclei at 6 hours post-infection.
Figure 13:
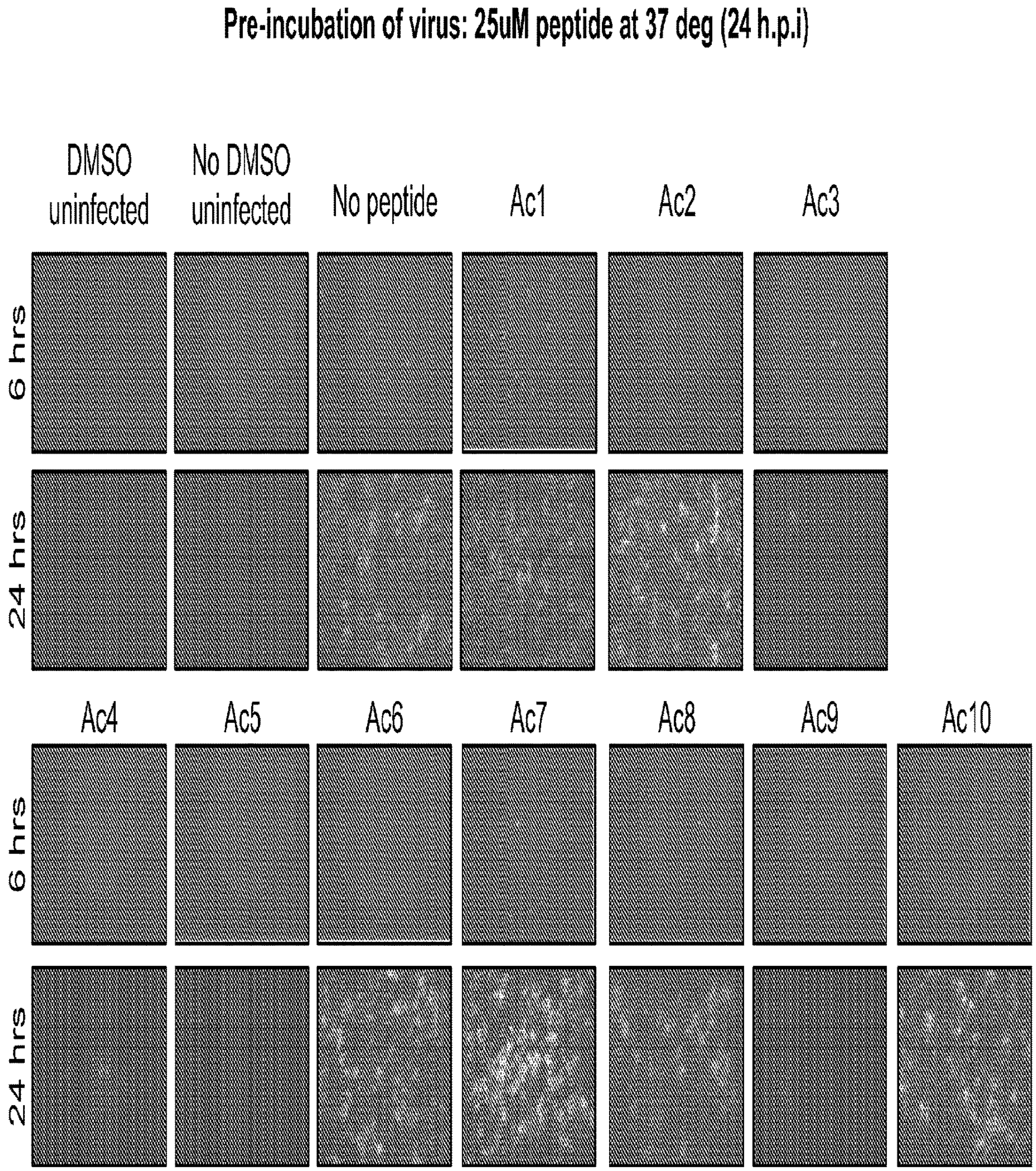
FIG. 13 shows immunofluorescence at 6 and 24 hours post-infection of Vero cells infected with Ebola virus after preincubation of the virus with the indicated peptides.

Similar experiments were performed with peptides Ac1-Ac10, which are N-terminally acetylated versions of peptides comprising the amino acid sequence set forth in SEQ ID NO: 2, 25, 28, 37, 42, 40, 34, 41, 35, and 36, respectively (see Table 5, below). Zaire Ebola virus was pretreated with 25 μM of Ac1, Ac2, Ac3, Ac4, Ac5, Ac5, Ac6, Ac7, Ac8, Ac9, or Ac10 for 30 minutes. Vero cells were then infected with the peptide/virus mixture at a multiplicity of infection of 1. The infected cells were evaluated at six and 24 hours post-infection by immunofluorescence to determine the level of virus infection. At six hours post-infection, many of the peptides, especially Ac3, Ac4, Ac5, and Ac9, inhibited the virus (FIG. 12 and FIG. 13). This inhibition was even more prevalent after 24 hours of infection (FIG. 13), at which point there were almost no infected cells in the Ac3-, Ac4-, Ac5-, and Ac9-treatment groups. These data indicate the EBOV GP2 CHR stapled peptides are effective at inhibiting EBOV infection.

TABLE 5

Peptides Ac1-Ac10

| SEQ ID NO. | Description | Sequence |
|---|---|---|
| 2 | Ac1 (EBOV GP2 CHR) | HDWTKNITDKIDQIIHDFVDK |

TABLE 5-continued

| Peptides Ac1-Ac10 | | |
|---|---|---|
| SEQ ID NO. | Description | Sequence |
| 25 | Ac2 (EBOV GP2 CHR [1, 5]) | **X**$_1$DWT**X**$_2$NITDKIDQIIHDFVDK, wherein each of $X_1$ and $X_2$ is (S)-2-(4'-pentenyl) Alanine |
| 28 | Ac3 (EBOV GP2 CHR 2, 6]) | H**X**$_1$WTK**X**$_2$ITDKIDQIIHDFVDK, wherein each of $X_1$ and $X_2$ is (S)-2-(4'-pentenyl) Alanine |
| 37 | Ac4 (EBOV GP2 CHR [1, 8]) | **X**$_1$DWTKNI**X**$_2$DKIDQIIHDFVDK, wherein $X_1$ is (R)-2-(7'-octenyl) alanine and $X_2$ is (S)-2-(4'-pentenyl) Alanine |
| 42 | Ac5 (EBOV GP2 CHR [5, 8, 12]) | HDWT**X**$_1$NI**X**$_2$DKI**X**$_3$QIIHDFVDK, wherein $X_1$ is (S)-2-(4'-pentenyl)Alanine, $X_2$ is 2,2-bis(4-pentenyl) glycine, and $X_3$ is (S)-2-(4'-pentenyl)Alanine |
| 40 | Ac6 (EBOV GP2 CHR [6, 13]) | HDWTK**X**$_1$ITDKID**X**$_2$IIHDFVDK, wherein $X_1$ is (R)-2-(7'-octenyl) alanine and $X_2$ is (S)-2-(4'-pentenyl)Alanine |
| 34 | Ac7 (EBOV GP2 CHR [9, 13]) | HDWTKNIT**X**$_1$KID**X**$_2$IIHDFVDK, wherein each of $X_1$ and $X_2$ is (S)-2-(4'-pentenyl) Alanine |
| 41 | Ac8 (EBOV GP2 CHR [9, 16]) | HDWTKNIT**X**$_1$KIDQII**X**$_2$DFVDK, wherein $X_1$ is (R)-2-(7'-octenyl) alanine and $X_2$ is (S)-2-(4'-pentenyl)Alanine |
| 35 | Ac9 (EBOV GP2 CHR [12, 16]) | HDWTKNITDKI**X**$_1$QII**X**$_2$DFVDK, wherein each of $X_1$ and $X_2$ is (S)-2-(4'-pentenyl) Alanine |
| 36 | Ac10 (EBOV GP2 CHR [13, 17]) | HDWTKNITDKID**X**$_1$IIH**X**$_2$FVDK, wherein each of $X_1$ and $X_2$ is (S)-2-(4'-pentenyl) Alanine |

Materials and Methods

SEboV Peptide Synthesis: Peptides were synthesized on a Tetras Peptide Synthesizer (Advanced ChemTech, Louisville, KY) using Fmoc-based solid phase peptide chemistry on Rink amide resin (30 μmol peptide per reaction). In brief, the synthesis protocol consisted of removal of the Fmoc protective group with 25% piperidine in NMP, washing with NMP, and subsequent amino acid coupling using 10 equiv. amino acid (1 mL, 0.3 M), HCTU (0-(1H-6-Chlorobenzotriazole-1-yl)-1,1,3,3-tetramethyluronium hexafluorophosphate) (0.99 mL, 0.3 M) and DIPEA (N,N-Diisopropylethylamine) (2.0 mL, 0.3 M) in NMP (N-methyl-2-pyrrolidone) for 60 minutes before draining and washing. All peptide sequences included an N-terminal β-alanine spacing residue. Stapled peptides underwent a further ring-closing metathesis reaction on the resin-bound N-terminal Fmoc-protected peptide. After washing with NMP and 1,2-dichloroethane, the resin was exposed to three 6-hour cycles of bis(tricyclohexylphosphine)benzylidine ruthenium (IV) dichloride (Grubbs' I catalyst, 3 mL, 1 mM) at room temperature in 1,2-dichloroethane. Peptides were primarily N-terminal acetylated for use in biochemical and cell-based assays. The acetylation reaction consisted of deprotection of the Fmoc group as outlined above, followed by reaction with neat acetic anhydride (1 mL) and DIPEA (2 mL, 0.3 M in NMP) for 1 hour. Other experiments made use of N-terminal peptides with fluorescent tags. For peptides tagged with fluorescein (FITC), Fmoc-deprotected peptides were exposed to fluorescein isothiocyanate (2.8 mL, 25 mM) and DIPEA (0.2 mL, 0.3 M) in DMF for 12 hours. For peptides tagged with N,N-dimethylaminocoumarin (DMACA), Fmoc-deprotected peptides were exposed to N-hydroxysuccinimidyl-7-dimethylaminocoumarin-4-acetate (2.8 mL, 25 mM) and DIPEA (0.2 mL, 0.3 M) in DMF for 12 hours. Final peptides were cleaved from the resin and fully deprotected by exposure to a solution containing 95% TFA (trifluoroacetic acid), 2.5% water, and 2.5% triisopropyl silane for 2.5-3 hours. The cleaved peptides were precipitated into ice-cold 1:1 methyl-tert-butyl ether (MTBE), re-suspended in water and lyophilized as crude peptides overnight. The lyophilized peptides were purified by C-18 reverse phase high performance liquid chromatography (HPLC) on an Agilent 1200 HPLC system (Santa Clara, CA).

Circular Dichroism (CD) Spectroscopy:

Acetylated compounds were dissolved in water or pH 4.6 acetate buffer to concentrations ranging from 60 to 75 μM. Final compound concentrations were determined by measuring sample absorbance at 205 nm using a NanoDrop2000 spectrophotometer (ThermoScientific, Wilmington, DE). Spectra were obtained on an Aviv Circular Dichroism Spectrometer, Model 420 (Aviv Biomedical, Inc, Lakewood, New Jersey) at 25° C. or at 80° C. for thermal denaturation study. The spectra were collected using a 0.1 cm path length quartz cuvette (Hellma Analytics, Germany) with the following measurement parameters: wavelength, 240-190 nm; step resolution, 0.50 nm; averaging time, 5.0 sec per step. Spectra were processed using Aviv CDS Program software and converted to mean residue molar ellipticity using the cuvette path length (0.1 cm), the measured concentration, and the number of amino acids in the peptide (cross-linking amino acids and β-alanine cap were included as amino acids in this count).

High Resolution Clear Native Electrophoresis (hrCNE):

hrCNE was performed as previously described (see, e.g., Bird et al., 2014, JCI, 124(5):2113-2124, Bird et al., 2010, PNAS, 107(32):14093-14098, and Harrison et al., 2011, Protein Sci., 20(9):1587-1596, each of which is incorporated by reference herein in its entirety). Briefly, 2.5 μM of either FITC WT EboV or FITC-SEboV-9 were incubated in the presence or absence of 50 μg/mL of histidine-tagged 5Helix protein (SEQ ID NO:74) in 1× ubiquitylation buffer (Enzo life sciences, BML-KW9885-0001). Binding reactions were incubated at 37° C. for 2 hours, and then loaded onto an 8.0% hrCNE acrylamide resolving gel. Proteins were resolved at 80 mV for 7 hours at 4° C. Fluorescent peptide bands were visualized using a Typhoon FLA 7000 imager (GE Healthcare Life Sciences). After imaging of the FITC channel, proteins were transferred to FL-PVDF (Millipore) membranes. The membranes were blocked and incubated overnight with a His-Tag antibody (Santa Cruz Biotechnology, sc-8036). His Tag-5Helix protein bands were visualized using IRDye mouse (LI-COR) secondary antibodies on a Li-Cor Odyssey 9120 Imaging System (LI-COR).

Fluorescence Microscopy:

Huh-7 hepatocyte carcinoma cells were plated in wells ($1\times10^5$ cells/well) of a 12-well glass bottom plate (Mattek P12G-1.5-14-F) in DMEM (Dulbecco's Modified Eagle Medium) medium containing 10% fetal bovine serum, 100 U/mL penicillin G, 100 μg/mL streptomycin sulfate, and 250 ng/mL amphotericin B. The following day, cells were transfected with CellLight Early Endosome-RFP (ThermoFisher, C10587) or CellLight Late Endosome-RFP (ThermoFisher, C10589) following the manufacturer's protocol. After 24 hours, to minimize autofluorescence, the medium was changed to transparent DMEM lacking phenol red (Lonza 12-917F), supplemented with 2% fetal bovine serum, 100 U/mL penicillin G, 100 μg/mL streptomycin sulfate, and 250 ng/mL amphotericin B. Cells were then treated with 1 μM SEboV-WT, 2 μM SEboV-3, or 1 μM SEboV-9 peptides labeled with DMACA. Images were taken every 20 minutes for a total of 24 hours using a Nikon TiE inverted fluorescence microscope (Nikon) with a custom incubation chamber to maintain constant 37° C. temperature, elevated humidity, and 5% $CO_2$ levels. Images were taken using a 20× Plan Apochromat 0.75 NA objective (Nikon MRD30205), a red filter set with a 560/40-nm excitation filter, 585-nm dichroic filter, and a 630/75-nm emission filter (Chroma Technologies 49008), a blue filter set with a 436/20-nm excitation filter, 455-nm dichroic, and a 480/40-nm emission filter (Chroma 49001), and an iXon Ultra 888 electron multiplying charged coupled device camera (Andor). Images were analyzed using NIS-Elements v 4.13.00 (Nikon).

Virus:

The C05 isolate of the Makona variant of EBOV (Ebola virus/*H.sapiens*-tc/GIN/2014/Makona-C05; GenBank: KX000398) was propagated in Vero E6 cells (BEI NR-596) and used after one or two passages. All procedures using infectious EBOV/Mak were performed under biosafety level 4 (BSL-4) conditions at the National Institute of Allergy and Infectious Diseases (NIAID) Integrated Research Facility at Fort Detrick (IRF-Frederick).

Cells:

Huh-7 (human hepatocellular carcinoma) cells were obtained from Dr. Hideki Ebihara (NIAID), Rocky Mountain Laboratories, Hamilton, MT.

Cell-Based Efficacy and Cytotoxicity Assays:

The hydrocarbon-stapled α-helical GP2 heptad repeat peptides were tested in Huh-7 cells seeded for 24 hours at a density of $3\times10^4$ in 96 well Operetta plates. The peptides were diluted 2-fold starting at a concentration of 50 μM and continuing for 8 dilutions to obtain a dose-response curve. The cells were treated with the peptides for 1 hour prior to infection with EBOV/Mak variant at a multiplicity of infection (MOI) of 0.2. After 48 hours, cells were fixed with 10% neutral-buffered formalin and analyzed using a chemiluminescent assay for efficacy. A mouse primary antibody against EBOV VP40 matrix protein (B-MD04-BD07-AE11, prepared by US Army Medical Research Institute of Infectious Diseases, Frederick, MD under Centers for Disease Control and Prevention contract) was used to detect EBOV. Peroxidase labeled anti-mouse IgG (Cat #074-1802, KPL Inc., Gaithersburg, MD) was used as a secondary antibody. Luminescence was detected with the SuperSignal® ELISA Pico Chemiluminescent Substrate (Thermo Scientific, Rockford, IL) kit and a Tecan Infinite M1000 Pro plate reader (Tecan, Morrisville, NC).

To analyze toxicity, Huh-7 cells were seeded in 96-well black opaque plates and treated with the peptides in the same manner as the efficacy plates. After 48 hours, the CellTiter-Glo® Luminescent Cell Viability Assay kit (Promega, Madison, WI) was used to quantify metabolically active cells. Luminescence was read on the Tecan Infinite M1000 Pro plate reader.

Inhibition was determined as percent relative to untreated infected cells, after subtracting background. IC50 and CC50 values were interpolated from the nonlinear regression analysis performed on the data points. GraphPad Software (La Jolla, CA) was used for fitted curves (log [agonist] vs response [variable slope] with constraint to remain above 0). Duplicate efficacy plates and one toxicity plate with triplicate wells per dose were run. The experiment was performed on two separate days. Error bars of dose-response curves represent the standard deviation of 12 replicates for efficacy and 6 replicates for cytotoxicity.

OTHER INSTANCES

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A structurally stabilized peptide comprising the amino acid sequence:

(a) HNWTKX$_1$ITNX$_2$INQIIHDFVNK, wherein each of X$_1$ and X$_2$ is independently a stapling amino acid (SEQ ID NO:15), and wherein the sidechains of X$_1$ and X$_2$ are cross-linked to each other;

(b) HDWTKX$_1$ITDX$_2$INQIIHDFVNK, wherein each of X$_1$ and X$_2$ is independently a stapling amino acid (SEQ ID NO:14), and wherein the sidechains of X$_1$ and X$_2$ are cross-linked to each other;

(c) X$_1$DWTX$_2$NITDKINQIIHDFVNK, wherein each of X$_1$ and X$_2$ is independently a stapling amino acid (SEQ ID NO:8), and wherein the sidechains of X$_1$ and X$_2$ are cross-linked to each other;

(d) X$_1$NWTX$_2$NITDKINQIIHDFVNK, wherein each of X$_1$ and X$_2$ is independently a stapling amino acid (SEQ ID NO:9), and wherein the sidechains of X$_1$ and X$_2$ are cross-linked to each other;

(e) HX$_1$WTKX$_2$ITDKINQIIHDFVNK, wherein each of X$_1$ and X$_2$ is independently a stapling amino acid (SEQ ID NO:11), and wherein the sidechains of X$_1$ and X$_2$ are cross-linked to each other;

(f) HNWTX$_1$NITX$_2$KINQIIHDFVNK, wherein each of X$_1$ and X$_2$ is independently a stapling amino acid (SEQ ID NO:12), and wherein the sidechains of X$_1$ and X$_2$ are cross-linked to each other;

(g) HDWTX$_1$NITX$_2$KINQIIHDFVNK, wherein each of X$_1$ and X$_2$ is independently a stapling amino acid (SEQ ID NO:13), and wherein the sidechains of X$_1$ and X$_2$ are cross-linked to each other;

(h) HX$_1$WTKNITX$_2$KIDQIIHDFVNK, wherein each of X$_1$ and X$_2$ is independently a stapling amino acid (SEQ ID NO:20), and wherein the sidechains of X$_1$ and X$_2$ are cross-linked to each other; or (i) HX$_1$WTKNITX$_2$KINQIIHDFVNK, wherein each of X$_1$ and X$_2$ is independently a stapling amino acid (SEQ ID NO:21), and wherein the sidechains of X$_1$ and X$_2$ are cross-linked to each other;

or a pharmaceutically acceptable salt thereof;

and wherein the structurally stabilized peptide is 21-50 amino acids in length.

2. The structurally stabilized peptide of claim 1, wherein the structurally stabilized peptide comprises:

a structure of Formula (I):

Formula (I)

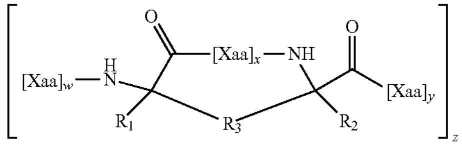
, or a pharmaceutically acceptable salt thereof, wherein:

each R$_1$ and R$_2$ is H or a C$_1$ to C$_{10}$ alkyl, alkenyl, alkynyl, arylalkyl, cycloalkylalkyl, heteroarylalkyl, or heterocyclylalkyl, any of which is substituted or unsubstituted;

each R$_3$ is independently alkylene, alkenylene, or alkynylene, any of which is substituted or unsubstituted;

z is 1; and (a) each [Xaa]$_w$ is HDWTK (SEQ ID NO:50), each [Xaa]$_x$ is ITD, and each [Xaa]$_y$ is INQIIHDFVNK (SEQ ID NO:51);

(b) each $[Xaa]_w$ is HDWT (SEQ ID NO:49), each $[Xaa]_x$ is NIT, and each $[Xaa]_y$ is KINQIIHDFVNK (SEQ ID NO:48);

(d) each $[Xaa]_w$ is absent, each $[Xaa]_x$ is DWT, and each $[Xaa]_y$ is NITDKINQIIHDFVNK (SEQ ID NO:44);

(e) each $[Xaa]_w$ is absent, each $[Xaa]_x$ is NWT, and each $[Xaa]_y$ is NITDKINQIIHDFVNK (SEQ ID NO:44);

(g) each $[Xaa]_w$ is H, each $[Xaa]_x$ is WTK, and each $[Xaa]_y$ is ITDKINQIIHDFVNK (SEQ ID NO:46);

(h) each $[Xaa]_w$ is HNWT (SEQ ID NO:47), each $[Xaa]_x$ is NIT, and each $[Xaa]_y$ is KINQIIHDFVNK (SEQ ID NO:48);

(i) each $[Xaa]_w$ is HNWTK (SEQ ID NO:52), each $[Xaa]_x$ is ITN, and each $[Xaa]_y$ is INQIIHDFVNK (SEQ ID NO:51);

(n) each $[Xaa]_w$ is H, each $[Xaa]_x$ is WTKNIT (SEQ ID NO:61), and each $[Xaa]_y$ is KIDQIIHDFVNK (SEQ ID NO:62);

(o) each $[Xaa]_w$ is H, each $[Xaa]_x$ is WTKNIT (SEQ ID NO:61), and each $[Xaa]_y$ is KINQIIHDFVNK (SEQ ID NO:48).

3. The structurally stabilized peptide or the pharmaceutically acceptable salt thereof of claim 2, wherein: $R_1$ is $C_1$ to $C_{10}$ alkyl, $R_2$ is $C_1$ to $C_{10}$ alkyl, and $R_3$ is alkenylene.

4. The structurally stabilized peptide or the pharmaceutically acceptable salt thereof of claim 2, wherein: $R_1$ is a methyl group, $R_3$ is 4-octenyl, and $R_2$ is a methyl group.

5. A structurally stabilized peptide comprising:

(a) an amino acid sequence set forth in SEQ ID NO:2 except with 3 to 12 amino acid substitutions and 0 to 5 deletions from the N-terminus, the C-terminus, or a combination thereof, of the amino acid sequence set forth in SEQ ID NO:2, or a pharmaceutically acceptable salt thereof;

wherein the structurally stabilized peptide comprises amino acid substitutions at the following positions (relative to SEQ ID NO:2) with non-natural amino acids with olefinic side chains:

(i) 2 and 6;

(ii) 2 and 9;

(iii) 6 and 10;

(iv) 1 and 8; or (v) 12 and 16;

wherein one or more aspartic acid at positions 2, 9, 12, 17 and 20 in SEQ ID NO: 2 is substituted by asparagine, wherein the structurally stabilized peptide binds to a 5 helix bundle or fusion bundle intermediate of EBOV GP2, wherein the structural stabilization comprises a hydrocarbon staple or stitch, and wherein the structurally stabilized is 16-50 amino acids in length; or (b) an amino acid sequence set forth in any one of SEQ ID NOs: 2-6 except with 2 to 13 amino acid substitutions and 0 to 5 deletions from the N-terminus, the C-terminus, or a combination thereof, of the amino acid sequence set forth in any one of SEQ ID NOs: 2-6, or a pharmaceutically acceptable salt thereof;

wherein the structurally stabilized peptide comprises amino acid substitutions at the following positions (relative to SEQ ID NO:2) with non-natural amino acids with olefinic side chains cross-linked to each other:

(i) 2 and 6;

(ii) 2 and 9;

(iii) 6 and 10;

(iv) 1 and 8; or (vi) 12 and 16;

wherein the structurally stabilized peptide does not comprise the amino acids corresponding to positions 610-612 of SEQ ID NO: 1, wherein at least one of the amino acids at positions 2, 9, 12, 17 and 20 (numbering with respect to SEQ ID NO:2) is asparagine, wherein the structurally stabilized peptide binds to a 5 helix bundle or fusion bundle intermediate of EBOV GP2; and wherein the structurally stabilized is 16-50 amino acids in length.

6. The structurally stabilized peptide of claim 5, wherein the structurally stabilized peptide comprises:

a structure of Formula (I):

Formula (I)

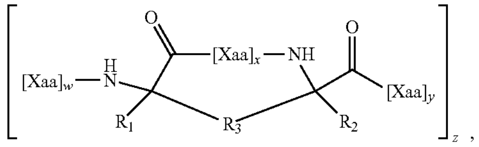

or a pharmaceutically acceptable salt thereof, wherein:

each $R_1$ and $R_2$ is H or a $C_1$ to $C_{10}$ alkyl, alkenyl, alkynyl, arylalkyl, cycloalkylalkyl, heteroarylalkyl, or heterocyclylalkyl, any of which is substituted or unsubstituted;

each $R_3$ is independently alkylene, alkenylene, or alkynylene, any of which is substituted or unsubstituted;

z is 1; and w+y is 12, 13, 14, 15, 16, 17, 18, 19, or 20; and each [Xaa] is an amino acid.

7. A peptide comprising an amino acid sequence:

(a) $HNWTKX_1ITNX_2INQIIHDFVNK$, wherein each of $X_1$ and $X_2$ is independently a stapling amino acid (SEQ ID NO:15);

(b) $HDWTKX_1ITDX_2INQIIHDFVNK$, wherein each of $X_1$ and $X_2$ is independently a stapling amino acid (SEQ ID NO:14);

(c) $X_1DWTX_2NITDKINQIIHDFVNK$, wherein each of $X_1$ and $X_2$ is independently a stapling amino acid (SEQ ID NO:8);

(d) $X_1NWTX_2NITDKINQIIHDFVNK$, wherein each of $X_1$ and $X_2$ is independently a stapling amino acid (SEQ ID NO:9);

(e) $HX_1WTKX_2ITDKINQIIHDFVNK$, wherein each of $X_1$ and $X_2$ is independently a stapling amino acid (SEQ ID NO:11);

(f) $HNWTX_1NITX_2KINQIIHDFVNK$, wherein each of $X_1$ and $X_2$ is independently a stapling amino acid (SEQ ID NO:12);

(g) $HDWTX_1NITX_2KINQIIHDFVNK$, wherein each of $X_1$ and $X_2$ is independently a stapling amino acid (SEQ ID NO:13);

(h) $HX_1WTKNITX_2KIDQIIHDFVNK$, wherein each of $X_1$ and $X_2$ is independently a stapling amino acid (SEQ ID NO:20); or (i) $HX_1WTKNITX_2KINQIIHDFVNK$, wherein each of $X_1$ and $X_2$ is independently a stapling amino acid (SEQ ID NO:21); and wherein the peptide binds a 5 helix bundle or fusion bundle intermediate of EBOV GP2, wherein the peptide is 21 to 50 amino acids in length.

8. A pharmaceutical composition comprising the structurally stabilized peptide of claim 1, and a pharmaceutically acceptable carrier.

9. A pharmaceutical composition comprising the structurally stabilized peptide of claim 5, and a pharmaceutically acceptable carrier.

10. The structurally stabilized peptide of claim 1, wherein the peptide comprises the amino acid sequence of HNWTKX$_1$ITNX$_2$INQIIHDFVNK, wherein each of X$_1$ and X$_2$ is(S)-2-(4'-pentenyl) Alanine (SEQ ID NO:33) and the sidechains of X$_1$ and X$_2$ are cross-linked to each other.

11. The structurally stabilized peptide of claim 5, wherein the peptide comprises the amino acid sequence of HNWTKX$_1$ITNX$_2$INQIIHDFVNK, wherein each of X$_1$ and X$_2$ is(S)-2-(4'-pentenyl) Alanine (SEQ ID NO:33) and the sidechains of X$_1$ and X$_2$ are cross-linked to each other.

12. The structurally stabilized peptide of claim 1, wherein the peptide comprises the amino acid sequence of:

(a) HNWTKX$_1$ITNX$_2$INQIIHDFVNK, wherein each of X$_1$ and X$_2$ is(S)-2-(4'-pentenyl) Alanine (SEQ ID NO:33), and wherein the sidechains of X$_1$ and X$_2$ are cross-linked to each other;

(b) HDWTKX$_1$ITDX$_2$INQIIHDFVNK, wherein each of X$_1$ and X$_2$ is(S)-2-(4'-pentenyl) Alanine (SEQ ID NO:32), and wherein the sidechains of X$_1$ and X$_2$ are cross-linked to each other;

(c) X$_1$DWTX$_2$NITDKINQIIHDFVNK, wherein each of X$_1$ and X$_2$ is(S)-2-(4'-pentenyl) Alanine (SEQ ID NO:26), and wherein the sidechains of X$_1$ and X$_2$ are cross-linked to each other;

(d) X$_1$NWTX$_2$NITDKINQIIHDFVNK, wherein each of X$_1$ and X$_2$ is(S)-2-(4'-pentenyl) Alanine (SEQ ID NO:27), and wherein the sidechains of X$_1$ and X$_2$ are cross-linked to each other;

(e) HX$_1$WTKX$_2$ITDKINQIIHDFVNK, wherein each of X$_1$ and X$_2$ is(S)-2-(4'-pentenyl) Alanine (SEQ ID NO:29), and wherein the sidechains of X$_1$ and X$_2$ are cross-linked to each other;

(f) HNWTX$_1$NITX$_2$KINQIIHDFVNK, wherein each of X$_1$ and X$_2$ is(S)-2-(4'-pentenyl) Alanine (SEQ ID NO:30), and wherein the sidechains of X$_1$ and X$_2$ are cross-linked to each other;

(g) HDWTX$_1$NITX$_2$KINQIIHDFVNK, wherein each of X$_1$ and X$_2$ is(S)-2-(4'-pentenyl) Alanine (SEQ ID NO:31), and wherein the sidechains of X$_1$ and X$_2$ are cross-linked to each other;

(h) HX$_1$WTKNITX$_2$KIDQIIHDFVNK, wherein X$_1$ is (R)-2-(7'-octenyl) alanine and X$_2$ is (S)-2-(4'-pentenyl) Alanine (SEQ ID NO:38), and wherein the sidechains of X$_1$ and X$_2$ are cross-linked to each other; or (i) HX$_1$WTKNITX$_2$KINQIIHDFVNK, wherein X$_1$ is (R)-2-(7'-octenyl) alanine and X$_2$ is (S)-2-(4'-pentenyl) Alanine (SEQ ID NO:39), and wherein the sidechains of X$_1$ and X$_2$ are cross-linked to each other.

13. A pharmaceutical composition comprising the structurally stabilized peptide of claim 12, and a pharmaceutically acceptable carrier.

14. A method of treating or preventing an Ebolavirus infection or disease in a subject in need thereof, the method comprising administering to the subject a therapeutically-effective amount of the structurally stabilized peptide of claim 1.

15. A method of treating or preventing an Ebolavirus infection or disease in a subject in need thereof, the method comprising administering to the subject a therapeutically-effective amount of the structurally stabilized peptide of claim 5.

16. A method of preventing transmission of an Ebolavirus infection from a first subject to a second subject, the method comprising administering to the first subject a therapeutically-effective amount of the structurally stabilized peptide of claim 1, wherein the first subject is a first human or a non-human primate or a fruit bat.

17. A method of preventing transmission of an Ebolavirus infection from a first subject to a second subject, the method comprising administering to the first subject a therapeutically-effective amount of the structurally stabilized peptide of claim 5, wherein the first subject is a first human or a non-human primate or a fruit bat.

18. The method of claim 14, wherein the peptide comprises the amino acid sequence of HNWTKX$_1$ITNX$_2$INQIIHDFVNK, wherein each of X$_1$ and X$_2$ is(S)-2-(4'-pentenyl) Alanine (SEQ ID NO:33) and the sidechains of X$_1$ and X$_2$ are cross-linked to each other.

19. A method of making a structurally stabilized peptide, the method comprising: (a) providing a peptide having comprising the amino acid sequence set forth in any one of SEQ ID NOs: 8, 9, 11-15, 20, 21, 26, 27, 29-33, 38, and 39, and (b) cross-linking the peptide to make a structurally stabilized peptide.

20. The method of claim 19, wherein the peptide comprises the amino acid sequence of HNWTKX$_1$ITNX$_2$INQIIHDFVNK, wherein each of X$_1$ and X$_2$ is(S)-2-(4'-pentenyl) Alanine (SEQ ID NO:33).

* * * * *